United States Patent
Theunissen et al.

(10) Patent No.: US 12,371,667 B2
(45) Date of Patent: Jul. 29, 2025

(54) ENHANCED METHODS FOR INDUCING AND MAINTAINING NAIVE HUMAN PLURIPOTENT STEM CELLS

(71) Applicants: Washington University, St. Louis, MO (US); Whitehead Institute for Biomedical Research, Cambridge, MA (US)

(72) Inventors: Thorold Theunissen, St. Louis, MO (US); Shafqat Khan, St. Louis, MO (US); Rudolf Jaenisch, St. Louis, MO (US)

(73) Assignees: Washington University, St. Louis, MO (US); Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 17/744,266

(22) Filed: May 13, 2022

(65) Prior Publication Data

US 2022/0364060 A1    Nov. 17, 2022

Related U.S. Application Data

(60) Provisional application No. 63/188,308, filed on May 13, 2021.

(51) Int. Cl.
*C12N 5/074* (2010.01)
*C12N 5/0735* (2010.01)

(52) U.S. Cl.
CPC ......... *C12N 5/0696* (2013.01); *C12N 5/0606* (2013.01); *C12N 2501/999* (2013.01)

(58) Field of Classification Search
CPC ................ C12N 5/0696; C12N 5/0606; C12N 2501/999
See application file for complete search history.

(56) References Cited

U.S. PATENT DOCUMENTS

| | | | |
|---|---|---|---|
| 874,817 A | 12/1907 | York | |
| 6,057,117 A | 5/2000 | Harrison et al. | |
| 6,153,618 A | 11/2000 | Schultz et al. | |
| 6,417,185 B1 | 7/2002 | Goff et al. | |
| 6,489,344 B1 | 12/2002 | Nuss et al. | |
| 6,608,063 B2 | 8/2003 | Nuss et al. | |
| 6,784,336 B2 | 8/2004 | Eggan et al. | |
| 7,482,367 B2 | 1/2009 | Aikawa et al. | |
| 7,491,829 B2 | 2/2009 | Laird et al. | |
| 8,709,718 B1 | 4/2014 | Thomas et al. | |
| 2001/0034051 A1 | 10/2001 | Nuss et al. | |
| 2002/0156087 A1 | 10/2002 | Nuss et al. | |
| 2004/0077707 A1 | 4/2004 | Desai et al. | |
| 2004/0092535 A1 | 5/2004 | Barsanti et al. | |
| 2004/0138273 A1 | 7/2004 | Wagman et al. | |
| 2004/0209878 A1 | 10/2004 | Guzi et al. | |
| 2005/0054663 A1 | 3/2005 | Bennett et al. | |
| 2006/0089369 A1 | 4/2006 | Nuss et al. | |
| 2006/0258686 A1 | 11/2006 | Cheresh et al. | |
| 2008/0058340 A1 | 3/2008 | Maderna et al. | |
| 2008/0255133 A1 | 10/2008 | Vernier et al. | |
| 2009/0227608 A1 | 9/2009 | Donato et al. | |
| 2009/0246198 A1 | 10/2009 | Dong et al. | |
| 2009/0275606 A1 | 11/2009 | Chikkanna et al. | |
| 2010/0249152 A1 | 9/2010 | Schenone et al. | |
| 2013/0040972 A1 | 2/2013 | Manley | |
| 2013/0059385 A1 | 3/2013 | Li et al. | |
| 2013/0196437 A1 | 8/2013 | Stankewicz et al. | |
| 2013/0273651 A1 | 10/2013 | Gold et al. | |
| 2021/0363495 A1* | 11/2021 | Hanna .................. | C12N 5/0606 |
| 2022/0364060 A1 | 11/2022 | Theunissen et al. | |

FOREIGN PATENT DOCUMENTS

| | | |
|---|---|---|
| WO | 2002085909 A1 | 10/2002 |
| WO | 2003011287 A1 | 2/2003 |
| WO | 2003049739 A1 | 6/2003 |
| WO | 2003073843 A2 | 9/2003 |
| WO | 2005035506 A1 | 4/2005 |
| WO | 2005039485 A2 | 5/2005 |
| WO | 2006091737 A1 | 8/2006 |
| WO | 2006137368 A1 | 12/2006 |
| WO | 2007002325 A1 | 1/2007 |
| WO | 2007002433 A1 | 1/2007 |
| WO | 2007096259 A1 | 8/2007 |
| WO | 2008020206 A2 | 2/2008 |
| WO | 2008021389 A2 | 2/2008 |
| WO | 2008024724 A1 | 2/2008 |
| WO | 2008024725 A1 | 2/2008 |
| WO | 2008055236 A2 | 5/2008 |
| WO | 2008067481 A1 | 6/2008 |
| WO | 2008076415 A1 | 6/2008 |
| WO | 2008078086 A1 | 7/2008 |
| WO | 2008089459 A1 | 7/2008 |
| WO | 2008101840 A1 | 8/2008 |
| WO | 2008120004 A1 | 10/2008 |
| WO | 2008124085 A2 | 10/2008 |
| WO | 2008125820 A1 | 10/2008 |
| WO | 2009013462 A1 | 1/2009 |
| WO | 2009018233 A1 | 2/2009 |
| WO | 2009018238 A1 | 2/2009 |
| WO | 2009021887 A1 | 2/2009 |
| WO | 2009074827 A2 | 6/2009 |
| WO | 2009093008 A1 | 7/2009 |

(Continued)

OTHER PUBLICATIONS

Jeon et al. Clinical Pharmacology & Therapeutics. 2017; 102(5): p. 726-730. (Year: 2017).*

(Continued)

*Primary Examiner* — Laura Schuberg
*Assistant Examiner* — Jianjian Zhu
(74) *Attorney, Agent, or Firm* — Polsinelli PC

(57) ABSTRACT

The present disclosure provides methods and compositions for inducing, maintaining and/or passaging naïve pluripotent stem cell. In some embodiments, the methods are performed in the absence of MEK inhibition which has been shown to result in genomic instability of naïve pluripotent stem cells.

1 Claim, 25 Drawing Sheets

(25 of 25 Drawing Sheet(s) Filed in Color)

(56) References Cited

FOREIGN PATENT DOCUMENTS

| | | |
|---|---|---|
| WO | 2009093009 A1 | 7/2009 |
| WO | 2009093013 A1 | 7/2009 |
| WO | 2009111278 A2 | 9/2009 |
| WO | 2009111279 A1 | 9/2009 |
| WO | 2009111280 A1 | 9/2009 |
| WO | 2009129246 A2 | 10/2009 |
| WO | 2009129938 A1 | 10/2009 |
| WO | 2009111277 A9 | 12/2009 |
| WO | 2009153554 A1 | 12/2009 |
| WO | 2010003022 A1 | 1/2010 |
| WO | 2010003025 A1 | 1/2010 |
| WO | 2010051933 A2 | 5/2010 |
| WO | 2010051935 A2 | 5/2010 |
| WO | 2010105082 A1 | 9/2010 |
| WO | 2010105110 A1 | 9/2010 |
| WO | 2010108652 A1 | 9/2010 |
| WO | 2010124290 A2 | 10/2010 |
| WO | 2010138377 A1 | 12/2010 |
| WO | 2010145197 A1 | 12/2010 |
| WO | 2011025927 A1 | 3/2011 |
| WO | 2011107608 A1 | 9/2011 |
| WO | 2012146724 A2 | 11/2012 |
| WO | 2013030216 A1 | 3/2013 |
| WO | 2013030365 A1 | 3/2013 |
| WO | 2013030366 A1 | 3/2013 |
| WO | 2013030367 A1 | 3/2013 |
| WO | 2013159103 A1 | 10/2013 |
| WO | 2013177133 A2 | 11/2013 |
| WO | 2014068035 A1 | 5/2014 |
| WO | 2015196072 A2 | 12/2015 |

OTHER PUBLICATIONS

Dutta et al. Stem Cells. 2011;29:618-628. (Year: 2011).*
Di Stefano et al. Nature Methods. 2018; 15: 732-740. (Year: 2018).*
Theunissen et al. Cell Stem Cell. 2014; 15: 471-487. (Year: 2014).*
Mandal P.K., et al., "Reprogramming Human Fibroblasts to Pluripotency Using Modified mRNA," Nature Protocols, 2013, vol. 8, No. 3, pp. 568-582.
Khan, et al., "Probing the signaling requirements for naive human pluripotency by high-throughput chemical screening," Cell Reports 35, 109233, Jun. 15, 2021.

* cited by examiner

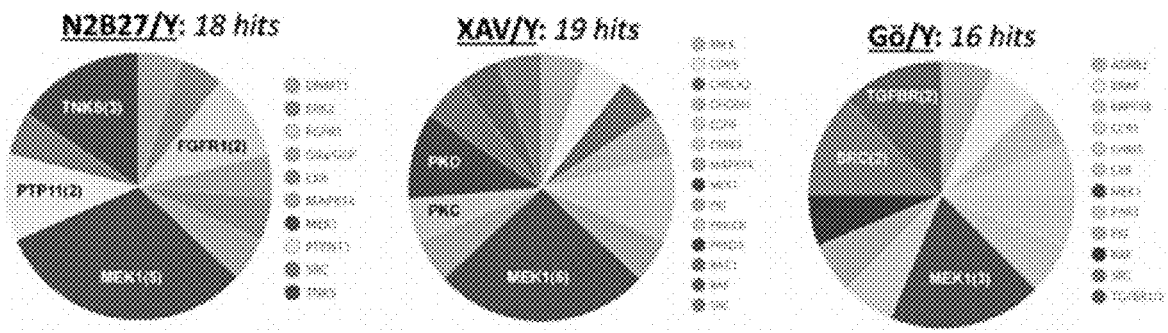
FIG. 1C
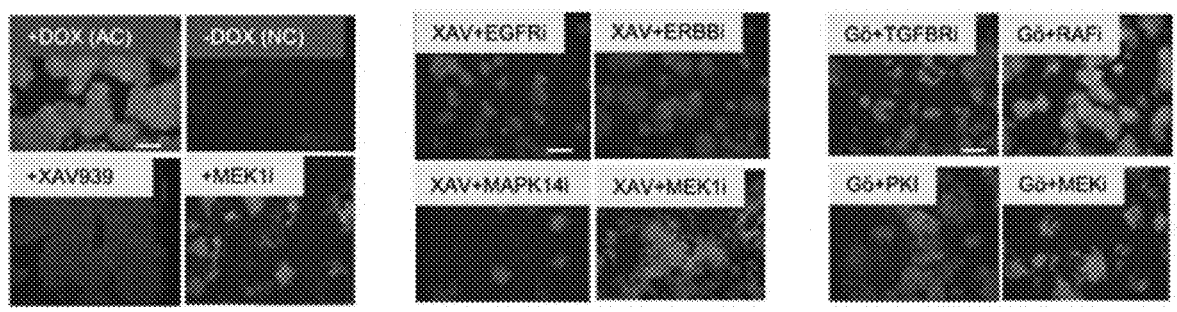
FIG. 1D
FIG. 1E

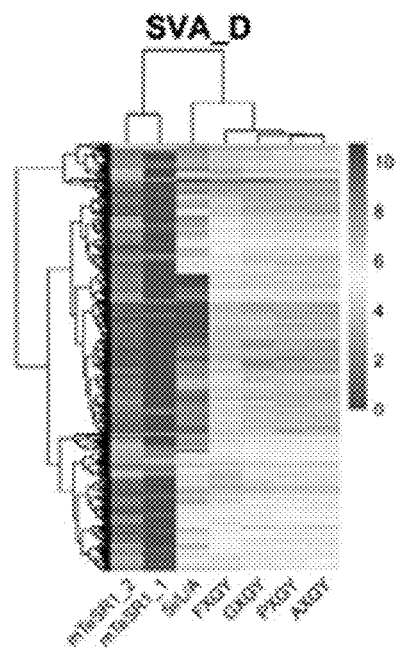
FIG. 4H
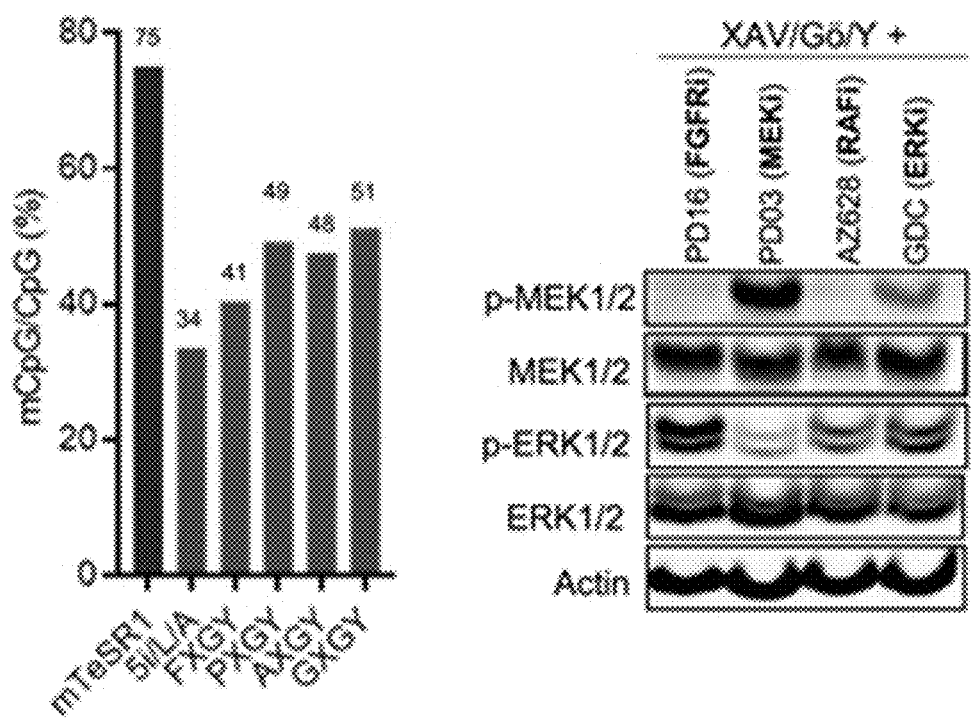
FIG. 4I
FIG. 4J

ENHANCED METHODS FOR INDUCING AND MAINTAINING NAIVE HUMAN PLURIPOTENT STEM CELLS

CROSS REFERENCE TO RELATED APPLICATIONS

This application claims the benefit of U.S. Provisional Application 63/188,308, filed May 13, 2021 the disclosure of which is hereby incorporated by reference in its entirety.

GOVERNMENT SUPPORT

This invention was made with government support under GM137418 awarded by the National Institutes of Health. The government has certain rights in the invention.

FIELD OF THE TECHNOLOGY

This disclosure generally relates to compositions and methods for inducing and maintaining naïve pluripotent stem cells.

BACKGROUND

Human pluripotent stem cells, including embryonic stem cells (ESCs) and induced pluripotent stem cells (iPSCs), hold great promise for regenerative medicine and disease modeling. Full realization of their potential is currently constrained by laborious culture requirements and inconsistencies in developmental potential between lines. Researchers have had a relatively easy time genetically manipulating and preventing differentiation in mouse ES and iPS cells. However, human ES cells can be more technically demanding to culture and exhibit properties such as slow growth and poor tolerance to passaging as single cells.

Thus, there is a need for more effective techniques to isolate and culture human pluripotent stem cells.

SUMMARY

Among the various aspects of the present disclosure are provided compositions and methods for inducing, maintaining, and/or passaging naïve pluripotent stem cells.

One aspect of the present disclosure encompasses methods of inducing, maintaining, or passaging at least one pluripotent stem cell in the absence of a mitogen-activated protein kinase kinase (MEK) inhibitor. In some embodiments, the methods generally comprise culturing the at least one pluripotent stem cell in the presence of at least one Tankyrase (TNKS) inhibitor, at least one Protein Kinase C (PKC) inhibitor, at least one Rho-Associated Protein kinase (ROCK) inhibitor, and at least one additional inhibitor selected from the group consisting of a Rapidly Accelerated Fibrosarcoma kinase (RAF) inhibitor, a Fibroblast Growth Factor Receptor 1 (FGFR1) inhibitor, an Extracellular Signal-Regulated Kinase (ERK) inhibitor, and any combination thereof. In some embodiments, the at least one pluripotent stem cells is an induced pluripotent stem cell (iPS) or embryonic stem cell.

In a certain embodiment, the at least one pluripotent stem cell is cultured in the presence of at least one TNKS inhibitor, at least one PKC inhibitor, at least one ROCK inhibitor, and at least one RAF inhibitor.

In another certain embodiment, the at least one pluripotent stem cell is cultured in the presence of at least one TNKS inhibitor, at least one PKC inhibitor, at least one ROCK inhibitor, and at least one FGFR1 inhibitor.

In still another certain embodiment, the at least one pluripotent stem cell is cultured in the presence of at least one TNKS inhibitor, at least one PKC inhibitor, at least one ROCK inhibitor, and at least one ERK inhibitor.

In yet another certain embodiment, the at least one pluripotent stem cell is cultured in the presence of at least one TNKS inhibitor, at least one PKC inhibitor, at least one ROCK inhibitor, FGFR1 inhibitor, and at least one ERK inhibitor.

In another certain embodiment, the at least one pluripotent stem cell is cultured in the presence of at least one TNKS inhibitor, at least one PKC inhibitor, at least one ROCK inhibitor, FGFR1 inhibitor, and at least one RAF inhibitor.

In still another certain embodiment, the at least one pluripotent stem cell is cultured in the presence of at least one TNKS inhibitor, at least one PKC inhibitor, at least one ROCK inhibitor, ERK inhibitor, and at least one RAF inhibitor.

In some embodiments, the TNKS inhibitor is PD0325901, the PKC inhibitor is Gö6983, the ROCK inhibitor is Y-27632, the ERK inhibitor is GDC-0994, the FGFR1 inhibitor is PD166866, and/or the RAF inhibitor is AZ628.

In some embodiments, the at least one pluripotent stem cell has elevated DNA methylation and/or HERVH transcription relative to at least one pluripotent stem cell cultured in the presence of a MEK inhibitor.

Another aspect of the present disclosure encompasses methods of inducing primed-to-naïve resetting of at least one primed pluripotent stem cell. In some embodiments, the methods generally comprise culturing the at least one primed pluripotent stem cell in the presence of at least one MEK inhibitor, at least one TNKS inhibitor, at least one PKC inhibitor, at least one ERK inhibitor, at least one ROCK inhibitor, and optionally Activin A. In some embodiments, the at least one primed pluripotent stem cell is an induced pluripotent stem cell (iPS) or embryonic stem cell.

In some embodiments, the MEK inhibitor is PD0325901, the TNKS inhibitor is PD0325901, the PKC inhibitor is Gö6983, the ERK inhibitor is GDC-0994, and/or the ROCK inhibitor is Y-27632.

In some embodiments, the naïve pluripotent stem cell has reduced phosphorylated ERK, reduced DNA methylation, and/or reduced HERVH transcription relative to a primed pluripotent stem cell.

In some embodiments, the pluripotent stem cells express naïve-specific cell surface markers after about 10 days of culture.

In some embodiments, the primed to naïve resetting is accelerated relative to at least one primed pluripotent stem cell cultured in the presence of 5i/L/A.

Another aspect of the present disclosure encompasses cell culture medium, the cell culture medium comprising at least one Tankyrase (TNKS) inhibitor, at least one Protein Kinase C (PKC) inhibitor, at least one Rho-Associated Protein kinase (ROCK) inhibitor, and at least one additional inhibitor selected from the group consisting of a Rapidly Accelerated Fibrosarcoma kinase (RAF) inhibitor, a Fibroblast Growth Factor Receptor 1 (FGFR1) inhibitor, an Extracellular Signal-Regulated Kinase (ERK) inhibitor, any combination thereof, and a basal medium.

Another aspect of the present disclosure encompasses cell culture medium, the cell culture medium comprising at least one MEK inhibitor, at least one TNKS inhibitor, at least one PKC inhibitor, at least one ERK inhibitor, at least one ROCK inhibitor, optionally Activin A and a basal medium.

Another aspect of the present disclosure encompasses kits for preparing the cell culture medium of the disclosure wherein the kits include individually packaged inhibitors, basal medium, and instructions for preparing the cell culture medium.

BRIEF DESCRIPTION OF THE FIGURES

The patent or application file contains at least one drawing executed in color. Copies of this patent or application publication with color drawing(s) will be provided by the Office upon request and payment of the necessary fee.

FIG. 1A-1E show high-throughput chemical screening for modulators of naïve human pluripotency in minimal conditions. FIG. 1A shows the experimental strategy for identifying compounds that maintain naïve human pluripotency in the presence or absence of MEK1/2 and GSK3 inhibitors (2i) using WIBR3 OCT4-ΔPE-GFP+naïve hESCs. FIG. 1B shows multi-parametric data analysis (MPDA) from a representative 384-well plate analyzed in two biological replicates showing the activity of small molecules with respect to active controls (AC, +DOX) and negative controls (NC, -DOX) based on high-content imaging. FIG. 1C shows pie charts summarizing the target classes of validated hit compounds in N2B27 medium supplemented with Y-27632 alone (N2B27/Y) (left), XAV939 and Y-27632 (XAV/Y) (middle), and G66983 and Y-27632 (GOP( )(right). Hit compounds were validated in two biological replicates. The scale bar depicts 260 μm. FIG. 1D shows fluorescent images of active control (+DOX), negative control (-DOX), and selected hit compounds in N2B27/Y (left), XAV/Y (middle), and GOP((right). Hit compounds were validated in two biological replicates. FIG. 1E shows structures and CIDs of 13 commercially available hit compounds that displayed validated activity in maintaining naïve human pluripotency in the three examined basal media in the absence of 2i (Y, Gö/Y, and XAV/Y). Source: PubChem. A full list of validated hit compounds in the absence of 2i is included in Table 2.

FIG. 2A shows the experimental scheme for extended maintenance assays to evaluate the efficacy of hit compounds using WIBR3 OCT4-ΔPE-GFP+ naïve hESCs derived in 5i/L/A. FIG. 2B shows quantitative gene-expression analysis for GFP in naïve hESCs that were switched from 5i/L/A to the indicated culture conditions for two passages. In this experiment, compounds were applied at 2.5 μM concentration. Error bars indicate mean±SD of three technical replicates. Data are representative of two biological replicates. FIG. 2C shows phase-contrast images (top) and flow-cytometry analyses using naïve-specific CD75 and SUSD2 antibodies (bottom) in H9-naïve hESCs that were switched from 5i/L/A to the indicated culture conditions for two passages. The scale bar depicts 250 μm. FIG. 2D shows Quantitative gene-expression analysis for the naïve-specific transcription factor KLF17 in samples shown in (FIG. 2C). Error bars indicate mean±SD of three technical replicates. FIG. 2E shows phase-contrast images (top), alkaline phosphatase (AP) staining (middle), and flow-cytometry analyses using naïve-specific CD75 and SUSD2 antibodies (bottom) in H9-naïve hESCs that were switched from 5i/L/A and maintained in four different naïve conditions for two passages. Data are representative of two biological replicates. The scale bar depicts 250 μm. FIG. 2F shows experimental scheme for evaluating the capacity of alternative naïve maintenance conditions to maintain biallelic X-linked reporter activity using WIBR3 MECP2-GFP/tdTomato reporter hESCs. FIG. 2G shows flow-cytometry analysis for GFP and tdTomato in naïve WIBR3 MECP2-GFP/tdTomato reporter hESCs that were derived from the primed state in 5i/L/A and thereafter maintained in a5i/L/A, AXGY, or AXGYU for two passages. FIG. 2H shows western blot analysis for p-ERK, total ERK, and β-actin in H9-naïve hESCs derived from the primed state in 5i/L/A and switched to PXGLY, a5i/L/A, AXGY, or AXGYU.

FIG. 3A shows a heatmap of RNA-seq data from primed hESCs maintained in mTeSR1 and naïve hESCs that were derived in 5i/L/A and subsequently maintained in 5i/L/A or three alternative naïve media (a5i/L/A, AXGY, or AXGYU) for two passages. Hierarchical clustering of Spearman's rank correlation coefficients between samples was performed considering significantly differentially expressed genes (DEGs) (abs (log2FC)>1.5, adj p<0.05). Data are shown for two independent genetic backgrounds (H9 and WIBR3 hESC lines). FIG. 3B shows an expression heatmap of selected naïve and primed-specific markers in the samples described in (FIG. 3A). FIG. 3C shows an expression heatmap of selected ERK-responsive target genes in the samples described in (FIG. 3A). FIG. 3D shows UMAP dimension reduction analysis of single cell RNA-seq data representing ICM, Pre-EPI, and Post-EPI from 3D-cultured human embryos compared to the naïve and primed samples described in (FIG. 3A). Clusters are drawn to indicate in vivo samples. FIG. 3E shows TE families upregulated in 5i/L/A (p-ERKLOW UP) versus three alternative naïve maintenance conditions (p-ERKHIGH UP). Histograms indicate the percentages of TE copies that are upregulated by logFC>2 in either sample group. FIG. 3F shows a heatmap indicating differentially expressed TE families between naïve H9 and WIBR3 hESCs maintained in 5i/L/A or three alternative naïve maintenance conditions. FIG. 3G shows a heatmap indicating expression of individual HERVH integrants in primed H9 and WIBR3 hESCs and naïve hESCs maintained in 5i/L/A or three alternative naïve maintenance conditions. FIG. 3H shows genome-wide CpG methylation level of all H9 samples described in (FIG. 3A) based on WGBS five passages after switching from 5i/L/A to the alternative naïve media. An accompanying tile-based measure of global DNA methylation.

FIG. 4A-4J show inhibition of other enzymes in the FGFR-RAF-MEK-ERK pathway also maintains naïve human pluripotency. FIG. 4A shows the experimental scheme for extended maintenance assays to evaluate the efficacy of FGFR1, RAF, MEK, and ERK inhibitors in the presence of TN KS, PKC, and ROCK inhibition (XAV/Gö/Y). FIG. 4B shows quantitative gene-expression analysis for the naïve-specific transcripts KLF17 and DNMT3L in the titration experiment shown in FIG. S4C. PXGY (PD03-XGY) and AXGY (AZ628-XGY) are included as controls. Error bars indicate mean±SD of three technical replicates. FIG. 4C shows phase-contrast images (top) and flow-cytometry analyses using naïve-specific CD75 and SUSD2 antibodies (bottom) in H9-naïve hESCs that were switched from 5i/L/A to the four alternative naïve maintenance media for two additional passages. Data are representative of two biological replicates. The scale bar depicts 250 μm. FIG. 4D shows phase-contrast images (top) and flow-cytometry analyses (bottom) of naïve WIBR3 MECP2-GFP/tdTomato reporter hESCs that were derived from the primed state in 5i/L/A and thereafter maintained in the four alternative naïve maintenance media for two passages. The scale bar depicts 250 µm. FIG. 4E shows an expression heatmap of selected naïve and primed-specific markers in H9 hESCs for the alternative naïve maintenance conditions described in (C). Gene expression was compared to H9 mTeSR1 and 5i/L/A samples previously analyzed in FIG. 3 and an additional H9 mTeSR1 sample (mTeSR1_2). FIG. 4F shows UMAP dimension reduction analysis of scRNA-seq data representing the ICM, Pre-EPI, and Post-EPI from 3D-cultured human embryos compared to the naïve and primed samples described in (FIG. 4E). Clusters are drawn to indicate in vivo samples. A time-course RNA-seq analysis of naïve hESCs undergoing capacitation into a formative pluripotent state was also integrated into this UMAP. FIG. 4G shows a heatmap indicating expression of individual HERVH integrants in primed H9 hESCs and naïve hESCs maintained in 5i/L/A or four alternative naïve maintenance conditions as described in (FIG. 4E). FIG. 4H shows a heatmap indicating expression of individual SVA_D integrants in H9 primed hESCs and naïve hESCs maintained in 5i/L/A or four alternative naïve conditions as described in (FIG. 4E). FIG. 4I shows genome-wide CpG methylation level of all H9 samples described in (C) based on whole-genome bisulfite sequencing five passages after switching from 5i/L/A to the four alternative naïve maintenance conditions. Data were compared to the H9 mTeSR1 sample previously analyzed in FIG. 3H. FIG. 4J shows western blot analysis for p-MEK1/2, total MEK1/2, p-ERK1/2, total ERK1/2, and β-actin (loading control) protein levels in H9-naïve hESCs derived from the primed state in 5i/L/A and switched to four alternative naïve conditions.

FIG. 5A shows an experimental scheme for evaluating the efficacy of alternative naïve maintenance media to induce naïve pluripotency in primed hESCs. Successful induction of naïve pluripotency was assessed by flow cytometry for the naïve-specific cell-surface markers CD75 and SUSD2 at the end of P1. FIG. 5B shows flow-cytometry analyses for naïve-specific cell-surface markers CD75 and SUSD2 at the end of P1 of primed-to-naïve conversion using H9 hESCs in 5i/L/A and four alternative naïve maintenance conditions. Data are representative of two biological replicates. FIG. 5C shows phase-contrast images (top) and flow-cytometry analysis for naïve-specific cell-surface markers CD75 and SUSD2 (bottom) in H9 primed hESCs upon treatment with XAV939, Gö6983, and Y-27632 (XAV/Gö/Y) together with the MEK inhibitor PD0325901 and the ERK inhibitor GDC-0994 (PXGGY) at the end of P1. Data are representative of two biological replicates. The scale bar depicts 250 µm. FIG. 5D shows UMAP dimension reduction analysis of single cell RNA-seq data representing the ICM, Pre-EPI, and Post-EPI from 3D-cultured human embryos compared to naïve hESCs that were derived in PXGGY at P1 and P8 or PXGGY+activin A(PXGGY/A) at P2. Expression data were compared to H9 mTeSR1 and 5i/L/A samples previously analyzed in FIG. 3. Clusters are drawn to indicate in vivo samples. A time-course RNA-seq analysis of naïve hESCs undergoing capacitation into a formative pluripotent state was also integrated into this UMAP. FIG. 5E shows an expression heatmap of selected naïve and primed-specific markers in H9 hESCs for the primed-to-naïve conversion conditions described in FIG. 5C and FIG. 5F. Naïve hESCs derived in PXGGY were examined at the end of P1 and P8. Naïve hESCs that were derived in PXGGY/A were also examined and subsequently maintained in the presence or absence of activin A for two passages (PXGGY-A) in two biological replicates each. Expression data were compared to H9 mTeSR1 and 5i/L/A samples previously analyzed in FIG. 3. FIG. 5F shows flow-cytometry analysis using antibodies for the naïve-specific cell-surface markers CD75 and SUSD2 in H9 primed hESCs upon treatment with 5i/L/A, PXGGY, and PXGGY/A at day 10 (top) and at the end of P1 (bottom) of primed-to-naïve resetting. Data are representative of two biological replicates. FIG. 5G shows alkaline phosphatase (AP) staining of H9 hESCs after two passages of primed-to-naïve conversion in 5i/L/A and PXGGY/A. Data are representative of two biological replicates. FIG. 5H shows genome-wide CpG DNA methylation level of H9-naïve hESCs that were converted in 5i/L/A or PXGGY/A at P5. Naïve hESCs that were derived in PXGGY/A were also examined and maintained for four additional passages in the absence of activin A. Data were compared to the H9 mTeSR1 and 5i/L/A samples previously analyzed in FIG. 4I. FIG. 5I shows western blot analysis for p-ERK1/2, total ERK1/2, and β-actin (loading control) protein levels in H9 primed hESCs treated with indicated media. FIG. 5J shows flow-cytometry analysis using antibodies for the naïve-specific cell-surface markers CD75 and SUSD2 to assess the effect of MEK inhibitor PD0325901 titration during primed-to-naïve resetting of H9 primed hESCs in PXGGY/A medium at the end of P1. FIG. 5K shows flow-cytometry analysis using antibodies for the naïve-specific cell-surface markers CD75 and SUSD2 during primed-to-naïve resetting of H9 primed hESCs by various combinations of FGF pathway inhibitors at the end of P1. Data are representative of two biological replicates.

FIG. 9A shows a schematic representation of ROCK inhibitor titration on H9 hESCs during primed-to-naïve reprogramming using the PXGGY/A cocktail. FIG. 9B shows images and CD75/SUSD2 FACS analysis at passage 1 (P1) of primed-to-naïve reprogramming of H9 hESC in PXGGY/A with titration of ROCKi. FIG. 9C shows representative images showing the effect of LIF, IM12, and WH-04 on the morphology of H9 cells at P2 of primed-to-naïve reprogramming in PXGGY/A. FIG. 9D shows images (top), AP staining (middle) and CD75/SUSD2 FACS analysis of H9 hESCs at P2 of primed-to-naïve reprogramming in PXGGY/A and PXGGY/A/LIW media. FIG. 9E shows representative images showing the effect of transient and permanent 10 μM ROCKi used during primed-to-naïve reprogramming of H9 hESCs at P2. FIG. 9F shows schematic representation of using WIBR3 MECP2-GFP/tdTomato reporter hESCs to assess XCR during primed-to-naïve reprogramming and maintenance. FIG. 9G shows FACS analysis for WIBR3 MECP2-GFP/tdTomato reporter hESCs at P3 of primed-to-naïve reprogramming in respective media. FIG. 9H shows FACS analysis for WIBR3 MECP2-GFP/tdTomato reporter hESCs at P3 of primed-to-naïve reprogramming in respective media. The ERK inhibitor GDC-0994 was withdrawn for two passages prior to FACS analysis. FIG. 9I shows schematic representation of H9 P1 naïve hESC reprogrammed in PXGGY/A/LIW and maintained in the absence of ERK inhibitor (PXGGY/A/LIW-GDC) for two passages. FIG. 9J shows images and CD75/SUSD2 FACS analysis of H9 primed hESCs reprogrammed in PXGGY/A/LIW and maintained in the absence of ERK inhibitor GDC-0994 (PXGGY/A/LIW-GDC) for two passages.

DETAILED DESCRIPTION

Figure 8:
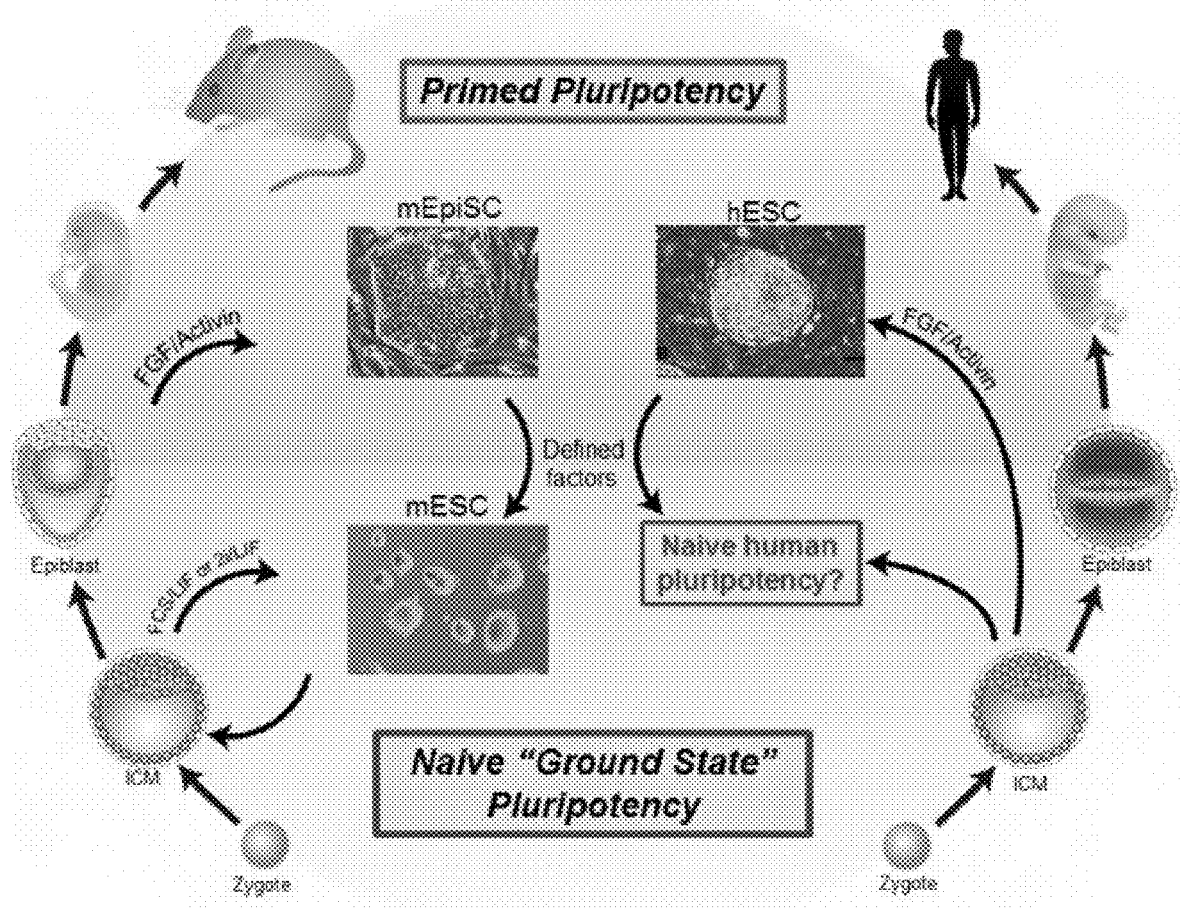
FIG. 8 shows an overview of pluripotent stem cell states in mouse and human. Two distinct pluripotent stem cell states have been stably isolated from mouse embryos: embryonic stem cells (ESCs) derived from the pre-implantation blastocyst are considered to be in a "naïve" pluripotent state, whereas epiblast stem cells (EpiSCs) derived from the post-implantation epiblast are in a "primed" pluripotent state. The naïve state has an unbiased developmental potential, while the primed state displays lineage priming and repressive chromatin. Human embryonic stem cells (ESCs) and induced pluripotent stem cells (iPSCs) most closely correspond to primate post-implantation embryos. There has been significant interest in isolating human ESCs and iPSCs in a naïve state that faithfully resembles the human pre-implantation blastocyst.

Embryonic stem cells (ESCs) have the ability to self-renew indefinitely while maintaining the capacity to differentiate into all cell types found in the body. Due to these unique properties, ESCs have become a versatile tool in wide-ranging biomedical applications, from disease modeling to toxicology testing to clinical trials. In addition, the discovery of induced pluripotent stem cells (iPSCs) provides new possibilities to model complex genetic disorders and a source of autologous cells for transplantation. However, major challenges must be overcome before human ESCs and iPSCs can be used in a realistic way in regenerative medicine. The main challenge is that current human ESCs and iPSCs do not resemble the ground state "naïve" pluripotent cells found in the blastocyst, but instead are more similar to "primed" precursors that arise after the embryo has implanted. The naïve state is signified by an unrestricted developmental potential, whereas the primed state displays repressive chromatin features and lineage priming (FIG. 8).

While naïve stem cells can be derived in rodents, their isolation has long remained elusive in the human system. The discovery of naïve human pluripotent stem cells has broad implications for biomedical research. First, naïve human cells may offer an enhanced starting point for differentiation into disease-relevant cell types, overcoming the heterogeneity frequently observed in current human ESCs and iPSCs. Second, the isolation of naïve human cells may provide a cell culture system to study epigenetic mechanisms of human pre-implantation development that cannot be investigated in primed cells. Such studies are essential to help understand the high percentage of unexplained pregnancy loss. Third, naïve induction may correct the erosion of dosage compensation prevalent in female human ESC and iPSC lines, enabling faithful in vitro modeling of X-linked diseases, such as mental retardation and autism spectrum disorders. Fourth, the injection of naïve human cells into the blastocyst of an animal host may allow the generation of interspecies chimeras, providing a novel paradigm to study functional cells derived from patient iPSCs in vivo.

The present disclosure is based, at least in part, on the discovery of essential signaling requirements for inducing and maintaining naïve human pluripotent stem cells (hPSCs). In particular, the present disclosure provides compositions and methods for culturing hPSCs which efficiently replace MEK inhibitors, an omnipresent component of naïve hPSCs protocols used to date and attributed to genetic and epigenetic instability, with inhibitors targeting either upstream (FGFR, RAF) or downstream (ERK) kinases. Furthermore, naïve hPSC self-renewal was optimally maintained by combining one of these FGF pathway inhibitors in combination with the tankyrase inhibitor XAV939, PKC inhibitor Gö6983, and ROCK inhibitor Y-27632 (XGY).

The present disclosure, in one aspect, is based on the identification of compounds (e.g., XAV939, Gö6983, Y-27362, AZ622, PD0325901, GDC-0994, PD166866 including pharmaceutically acceptable salts, solvates, hydrates, polymorphs, co-crystals, tautomers, stereoisomers, isotopically labeled derivatives, and prodrugs thereof) that support the maintenance, passage, and/or primed-to-naïve resetting of human pluripotent stem cells Additional aspects of the disclosure are described below.

In some embodiments, the in vitro or ex vivo culturing system disclosed herein may use pluripotent stem cells (e.g., human pluripotent stem cells). As used herein, "pluripotent" or "pluripotency" refers to the potential to form all types of specialized cells of the three germ layers (endoderm, mesoderm, and ectoderm); and is to be distinguished from "totipotent" or "totipotency", that is the ability to form a complete embryo capable of giving rise to offsprings. As used herein, "human pluripotent stem cells" (hPS) cells refers to human cells that have the capacity, under appropriate conditions, to self-renew as well as the ability to form any type of specialized cells of the three germ layers (endoderm, mesoderm, and ectoderm). hPS cells may have the ability to form a teratoma in 8-12 week old SCID mice and/or the ability to form identifiable cells of all three germ layers in tissue culture. Included in the definition of human pluripotent stem cells are embryonic cells of various types including human embryonic stem (hES) cells, (see, e.g., Thomson et al. (1998), Heins et. al. (2004), as well as induced pluripotent stem cells [see, e.g. Takahashi et al., (2007); Zhou et al. (2009); Yu and Thomson in Essentials of Stem Cell Biology (2nd Edition].

Embryonic stem cells (ESCs) and induced pluripotent stem cells (iPSCs) have attracted much attention because of their potential to mature into virtually any cell type in the body. However, mouse ESCs and iPSCs have different growth factor requirements and provide a more reliable vehicle for directed differentiation as compared to human ESCs and iPSCs. It was thought for many years that these differences reflected variation between species. In 2007, however, two groups reported that novel stem cell lines derived from the post-implantation epiblast of mouse embryos, called EpiSCs, have properties similar to human ESCs. These include a flat morphology, dependence on bFGF and activin signaling, and use of the OCT4 proximal enhancer element. The inner cell mass (ICM)-like state of mouse ESCs was described as "naïve," whereas EpiSCs and human ESCs were designated as "primed"; the implication is that the primed state is prone to differentiate, whereas the naïve condition corresponds to the more immature "ground state" of pluripotency.

The various methods described herein may utilize hPS cells from a variety of sources. For example, hPS cells suitable for use may have been obtained from developing embryos by use of a nondestructive technique such as by employing the single blastomere removal technique described in e.g. Chung et al (2008), further described by Mercader et al. in Essential Stem Cell Methods (First Edition, 2009). Additionally or alternatively, suitable hPS cells may be obtained from established cell lines or may be adult stem cells.

In some aspects, the pluripotent stem cells for use according to the disclosure may be human embryonic stem cells. Various techniques for obtaining hES cells are known to those skilled in the art. In some instances, the hES cells for use according to the present disclosure are ones, which have been derived (or obtained) without destruction of the human embryo, such as by employing the single blastomere removal technique known in the art. See, e.g., Chung et al., Cell Stem Cell, 2(2):113-117 (2008), Mercader et al., Essential Stem Cell Methods (First Edition, 2009). Suitable hES cell lines can also be used in the methods disclosed herein. Examples include, but are not limited to, cell lines H1, H9, SA167, SA181, SA461 (Cellartis AB, Goteborg, Sweden) which are listed in the NIH stem cell registry, the UK Stem Cell bank and the European hESC registry and are available on request. Other suitable cell lines for use include those established by Klimanskaya et al., Nature 444:481-485 (2006), such as cell lines MA01 and MA09, and Chung et al., Cell Stem Cell, 2(2):113-117 (2008), such as cell lines MA126, MA127, MA128 and MA129, which all are listed with the International Stem Cell Registry (assigned to Advanced Cell Technology, Inc. Worcester, MA, USA).

Alternatively, the pluripotent stem cells for use in the methods disclosed herein may be induced pluripotent stem cells (iPS) cells such as human iPS cells. As used herein "hiPS cells" refers to human induced pluripotent stem cells. hiPS cells are a type of pluripotent stem cells derived from non-pluripotent cells—typically adult somatic cells—by induction of the expression of genes associated with pluripotency, such as SSEA-3, SSEA-4, TRA-1-60, TRA-1-81, Oct-4, Sox2, Nanog and Lin28. Various techniques for obtaining such iPS cells have been established and all can be used in the present disclosure. See, e.g., Takahashi et al., Cell 131(5):861-872 (2007); Zhou et al., Cell Stem Cell. 4(5): 381-384 (2009); Yu and Thomson in Essentials of Stem Cell Biology (2nd Edition, Chapter 4). It is also envisaged that the hematopoietic progenitor cells may also be derived from other pluripotent stem cells such as adult stem cells, cancer stem cells or from other embryonic, fetal, juvenile or adult sources.

Current methods for maintaining and/or passaging pluripotent stem cells require the inclusion of an inhibitor of the mitogen-activated protein kinase kinase enzymes MEK1 and/or MEK2 (MEK inhibitor) (e.g., 5i/L/A). These protocols are inefficient and accompanied by widespread cell death when first applied to conventional primed hPSCs. In addition, protocols utilizing MEK inhibitors have been shown to be associated with genetic instability during extended culture and loss of parent-specific DNA methylation marks at imprinted loci. Thus, the present disclosure provides methods for maintaining and/or passaging at least one pluripotent stem cell in the absence of a MEK inhibitor. In one embodiment, the method generally comprises culturing at least one pluripotent stem cell in the presence of at least one Tankyrase (TNKS) inhibitor, at least one Protein Kinase C (PKC) inhibitor, at least one Rho-Associated Protein kinase (ROCK) inhibitor, and at least one additional inhibitor selected from the group consisting of a Rapidly Accelerated Fibrosarcoma kinase (RAF) inhibitor, a Fibroblast Growth Factor Receptor 1 (FGFR1) inhibitor, an Extracellular Signal-Regulated Kinase (ERK) inhibitor, and any combination thereof. In some embodiments, in addition to the above inhibitors, the method may include culturing the at least one pluripotent stem cell in the presence of Activin A and/or LIF cytokine.

Inhibitors useful in the context of the present disclosure include but are not limited to small molecules, antibodies/antibody fragments (e.g. targeting extracellular receptors or extracellular kinase domains), inhibitory RNA (e.g. short interfering RNA or short hairpin RNA), and/or aptamers. The inhibitor as described herein are understood to specifically inhibit their target through direct interaction unless explicitly described to the contrary.

A "small molecule," (M) as used herein, refers to an alkyl, alkenyl, alkynyl, aryl, heteroaryl, carbocyclic, or heterocyclic moiety, as defined herein, comprising carbon and hydrogen, and optionally comprising one or more heteroatoms as a part of the molecule (in the case of heteroaryl and heterocyclic groups) and/or attached to the molecule selected from oxygen, nitrogen, sulfur, phosphorus, boron, silicon, and selenium. In certain embodiments, the specificity of the inhibitors is given by the IC50 value. The IC50 value is defined as the concentration of inhibitor required to inhibit 50% of the kinase activity. In certain embodiments, an inhibitor compounds according to the disclosure may exhibit IC50 values<100 µM. In certain other embodiments, the compounds exhibit IC50 values<50 µM. In certain other embodiments, the compounds exhibit IC50 values<40 µM. In certain other embodiments, the compounds exhibit IC50 values<30 µM. In certain other embodiments, the compounds exhibit IC50 values<20 µM. In certain other embodiments, the compounds exhibit IC50 values<10 µM. In certain other embodiments, the compounds exhibit IC50 values<7.5 µM. In certain embodiments, the compounds exhibit IC50 values<5 µM. In certain other embodiments, the compounds exhibit IC50 values<2.5 µM. In certain embodiments, the compounds exhibit IC50 values<1 µM. In certain embodiments, the compounds exhibit IC50 values<0.75 µM. In certain embodiments, the compounds exhibit IC50 values<0.5 µM. In certain embodiments, the compounds exhibit IC50 values<0.25 µM. In certain embodiments, the compounds exhibit IC50 values<0.1 µM. In certain other embodiments, the compounds exhibit IC50 values<75 nM. In certain other embodiments, the compounds exhibit IC50 values<50 nM. In certain other embodiments, the compounds exhibit IC50 values<25 nM. In certain other embodiments, the compounds exhibit IC50 values<10 nM. In other embodiments, the compounds exhibit IC50 values<7.5 nM. In other embodiments, the compounds exhibit IC50 values<5 nM.

In certain embodiments, the RAF inhibitor is one or more of AZ628, BAY-439006, GDC-0879, SB590885, sorafenib, PLX4720, PLX-3603, GSK2118436, N-(3-(5-(4-chlorophenyl) -1H-pyrrolo[2;3-b]pyridine-3-carbonyl)-2;4-difluorophenyl)propane-I-sulfonamide, vemurafenib (also known as Zelobraf® and PLX-4032), GSK 2118436, RAF265 (Novartis), XL281, ARQ736, ZM336372, GW507, Debrafenib Mesylate, L779450, LGX818, TK632, LY3009120, PLX8394, Agerafenib, RAF709, a compound described in international PCT application publication, WO 2015/196072, WO 2007/002325, WO 2007/002433, WO 2009/111278, WO 2009/111279, WO 2009/111277, WO 2009/111280, or WO 2011/025927, or a compound described in U.S. Pat. No. 7,491,829 or U.S. Pat. No. 7,482,367. In a preferred embodiment, the RAF inhibitor is a pan-RAF inhibitor. In an exemplary embodiment, the RAF inhibitor is AZ628.

In certain embodiments, the ROCK inhibitor is one or more of Y-27632, fasudil (HA-1077), thiazovivin, AMA0076, AR-12286, AMA0076, AR-12286, AR-13324, ATS907, DE-104, INS-115644, INS-117548, K-115, PG324, Y-39983, RKI-983, SNJ-1656, ZINC00881524, GSK429286A, RKI1447, GSK269962, AR-13324, Y-33075, KD025, HA-1100, H-1152, a compound described in international PCT application publication, WO 2015/196072, WO 2014/068035, WO 2013/030216, WO 2013/030367, WO 2013/030366, WO 2013/030365, WO 2011/107608, WO 2012/146724, WO 2006/137368, or WO 2005/035506; or a compound described in U.S. patent application publication, US 2013/196437. In an exemplary embodiment, the ROCK inhibitor is Y-27632.

In certain embodiments, the FGFR1 inhibitor is one or more of PD166866, PD173074, cediranib, brivanib, TSU-68, BIBF1120, dovitinib, K123057, MK-2461, E7080, SU5402, BGJ398, E-3810, AZD4547, PLX052, SSR128129E, and a compound described in U.S. Pat. No. 8,709,718. In an exemplary embodiment, the FGFR1 inhibitor is PD166866.

In certain embodiments, the ERK inhibitor is one or more of (S)-I-(I-(4-chloro-3-fluorophenyl) -2-hydroxyethyl)-4-(2-((I-methyl-IH-pyrazol-5-yl) amino)pyrimidin-4-yl)pyridin-2(1H)-one (Ia, GDC-0994), 4-(3-((ethyldimethylsilyl) methyl) [I,2,4]triazolo[4,3-a]pyridin-7-yl)-N-(I-methyl-IH-pyrazol-5-yl) pyrimidin-2-amine (Ib), (S)-4-(3-(2-(4-chlorophenyl)-2-methoxyethyl)[I,2,4]triazolo[4,3-b]pyridazin-7-yl)-N-(I-methyl-IH-pyrazol-5-yl)pyrimidin-2-amine (Ic), (S)-N-(I-methyl-IH-pyrazol-5-yl) -4-(3-(2-methylbutyl)-[I,2,3]triazolo[I,5-a]pyridin-6-yl)pyrimidin-2-amine (Id), ulixertinib, RG7842, CC-90003, ASN-007, AMO-01, KO-947, AEZS-134, AEZS-131, AEZS-140, AEZS-136, AEZS-132, D-87503, KIN-2118, RB-I, RB-3, SCH-772984, MK-8353, SCH-900353, FR-180204, IDN-5491, hyperforin trimethoxybenzoate, ERK1-2067, ERK1-23211, ERK1-624, LY3214996, AZ6197, ASTX029, AZD0364, Magnolin, AG126 and LTT462. In an exemplary embodiment, the ERK inhibitor is GDC-0994.

In certain embodiments, the TNKS inhibitor is one or more of XAV939, MN-64, IWRI, G007-LK, WIKI4, JW55 and a pyrimidinone nicotinamide mimetic (e.g., AZ-6102). In an exemplary embodiment, the TNKS inhibitor is XAV939.

In certain embodiments, the PKC inhibitor is one or more of Gö6983 (3-[1-[3-(dimethylamino)propyl]-5-methoxy-1H-indole-3-yl]-4-(1H-indole-3-yl)-1H-pyrrole-2,5-dione; CAS registry number: 133053-19-7), GF109203X (3-(1-(3-dimethylamino)propyl) -1H-indole-3-yl)-4-(1H-indole-3-yl)-1H-pyrrole-2,5-dione, LY317615, AEB071, AM-2282, Ro 31-8220 Mesylatte, Dequalinium Chloride, LXS-196 and CAS registry number: 133052-90-1). In an exemplary embodiment, the PKC inhibitor is Gö6983.

In some embodiments, the above various inhibitors are included in a base media. Thus, the present disclosure provides a cell culture media for maintaining naïve pluripotent stem cells in the absence of MEK inhibitors. A "cell culture medium" (also referred to herein as a "culture medium" or "medium") is a medium for culturing cells containing nutrients that maintain cell viability and support proliferation. The cell culture medium may contain any of the following nutrients in appropriate amounts and combinations: salt(s), buffer(s), amino acids, glucose or other sugar(s), antibiotics, serum or serum replacement, and other components such as, but not limited to, peptide growth factors, cofactors, and trace elements. Cell culture media ordinarily used for particular cell types are known to those skilled in the art. For example, cell culture media of use for culturing and maintaining pluripotent cells are known in the art.

In some embodiments, the cell culture medium is chemically defined medium. In some embodiments, cell culture medium is serum-free medium, e.g., mTeSRI™ medium (StemCell Technologies, Vancouver, BC). In some embodiments, the culture medium comprises one or more supplements, such as, but not limited to N2 and B27. In some embodiments, the cell culture medium comprises a serum replacement composition. In some embodiments, the cell culture medium comprises low amount, such as less than 1% or less than 0.5%, of knock-out serum replacement medium. In some embodiments, the cell culture medium does not comprise a serum replacement composition. In some embodiments, the cell culture medium comprises an activator of STAT3 pathways, for example but not limited to leukemia inhibitory factor (LIF). In some embodiments, the cell culture comprises serum free recombinant human LIF.

In some embodiments, the cell culture medium comprises a base medium to which one or more supplements are added, such as: DMEM/F12, Neurobasal, N2 supplement, 10 mL B27 supplement, human LIF, glutamine, nonessential amino acids, β-mercaptoethanol, penicillin-streptomycin, and/or BSA (Sigma). In some embodiments, the cell culture medium is free or essentially free of components of non-human origin. In some embodiments, the cell culture medium is free or essentially free of components isolated from humans or non-human animals. In some embodiments, the cell culture medium uses recombinant human proteins (e.g., recombinant human albumin). In some embodiments, the base media is N2B27 media. In some embodiments, the base media is serum free.

As used herein, a "basal medium" is typically an unsupplemented medium (e.g., Eagle's minimal essential medium (EMEM); Dulbecco's modified Eagle's medium (DMEM)). As will be appreciated by those of skill in the art, a basal medium can comprises a variety of components such as one or more amino acids (e.g., non-essential amino acids, essential amino acids), salts (e.g., calcium chloride, potassium chloride, magnesium sulfate, sodium chloride, and monosodium phosphate), sugars (e.g., glucose), and vitamins (e.g., folic acid, nicotinamide, riboflavin, B12), iron and pH indicators (e.g., phenol red). The basal medium can further comprise proteins (e.g., albumin), hormones (e.g., insulin), glycoproteins (e.g., transferrin), minerals (e.g., selenium), serum (e.g., fetal bovine serum), antibiotics, antimycotics and glycosaminoglycans.

The concentration of the inhibitors used in the culture medium will depend on the amount of culture medium being generated. In some embodiments, 0.1 µM, 0.2 µM, 0.3 µM, 0.4 µM, 0.5 µM, 1 µM, 1.5 µM, 2.0 µM, 2.5 µM, 3.0 µM, 3.5 µM, 4.0 µM, 4.5 µM, 5.0 µM, 5.5 µM, 6.0 µM, 6.5 µM, 7.0 µM, 8.0 µM, 8.5 µM, 9.0 µM, 9.5 µM, 10.5 µM, 11.0 µM, 12.0 µM 13.0 µM, 14.0 µM, or 15.0 µM of one or more inhibitors are included in about 500 mL of culture medium. In some embodiments, about 1-10 µM of RAF inhibitor is used in about 500 ml of culture medium. In some embodiments, about 0.2-2 µM of FGFR1 inhibitor is used in about 500 ml of culture medium. In some embodiments, about 0.4-4 µM of PKC inhibitor is used in about 500 ml of culture medium. In some embodiments, about 2-20 µM of ROCK inhibitor is used in about 500 ml of culture medium. In some embodiments, about 0.4-4 µM of TNKS inhibitor is used in about 500 ml of culture medium. In some embodiments, 0.5-5 µM of ERK inhibitor is used in about 500 ml of culture medium.

In some embodiments, the inhibitors for use in a cell culture medium according to the disclosure comprises, consists essentially of, or consists of about 1-10 µM of RAF inhibitor, about 0.4-4 µM of TNKS inhibitor, about 0.4-4 µM of PKC inhibitor, and about 2-20 µM of ROCK inhibitor. In some embodiments, the inhibitors for use in a cell culture medium according to the disclosure comprises, consists essentially of, or consists of about 0.2-2 µM of FGFR1 inhibitor, about 0.4-4 µM of TNKS inhibitor, about 0.4-4 µM of PKC inhibitor, and about 2-20 µM of ROCK inhibitor. In some embodiments, the inhibitors for use in a cell culture medium according to the disclosure comprises, consists essentially of, or consists of about 0.5-5 µM of ERK inhibitor, about 0.4-4 µM of TNKS inhibitor, about 0.4-4 µM of PKC inhibitor, and about 2-20 µM of ROCK inhibitor. In some embodiments, the inhibitors for use in a cell culture medium according to the disclosure comprises, consists essentially of, or consists of about 1-10 µM of RAF inhibitor, about 0.2-2 µM of FGFR1 inhibitor, about 0.4-4 µM of TNKS inhibitor, about 0.4-4 µM of PKC inhibitor, and about 2-20 µM of ROCK inhibitor. In some embodiments, the inhibitors for use in a cell culture medium according to the disclosure comprises, consists essentially of, or consists of about 0.5-5 µM of ERK inhibitor, about 0.2-2 µM of FGFR1 inhibitor, about 0.4-4 µM of TNKS inhibitor, about 0.4-4 µM of PKC inhibitor, and about 2-20 µM of ROCK inhibitor. In some embodiments, the inhibitors for use in a cell culture medium according to the disclosure comprises, consists essentially of, or consists of about 0.5-5 µM of ERK inhibitor, about 1-10 µM of RAF inhibitor, about 0.4-4 µM of TNKS inhibitor, about 0.4-4 µM of PKC inhibitor, and about 2-20 µM of ROCK inhibitor. In each of the above embodiments, the cell culture medium may optionally include Activin A.

In another aspect, the present disclosure provides methods for primed-to-naïve resetting of at least one pluripotent stem cell. In one embodiment, the method for primed-to-naïve resetting generally comprises of culturing at least one pluripotent stem cell in the presence of at least one MEK inhibitor at least one TNKS inhibitor, at least one PKC inhibitor, at least one ERK inhibitor, at least one ROCK inhibitor, and optionally Activin A. Suitable TNKS Inhibitors, PKC inhibitors, ERK inhibitors, ROCK inhibitor and concentrations of the same are described above and useful for primed-to-naïve resetting.

In certain embodiments, the MEK inhibitor is one or more of PD0325901 (N-[(2R)-2,3-dihydroxypropoxy]-3,4-difluoro-2-[(2-fluoro-4-iodophenyl)amino]-benzamide; CAS registry number: 391210-10-9), U0126 (1,4-diamino-2,3-dicyano-1,4-bis[2-aminophenylthio]butadiene; CAS registry number: 109511-58-2), PD98059 (2-(2-amino-3-methoxyphenyl)-4H-1-benzopyran-4-one; CAS registry number: 167869-21-8), PD184352 (2-(2-chloro-4-iodo phenylamino)-N-cyclopropylmethoxy-3,4-difluorobenzamide; CAS registry number: 212631-79-3, a compound described in international PCT application publication, WO 2015/196072, WO 2010/138377, WO 2009/153554, WO 2009/093009, WO 2009/013462, WO 2009/093013, WO 2008/020206, WO 2008/078086, WO 2008/120004, WO 2008/125820, WO 2009/093008, WO 2009/074827, WO 2009/093009, WO 2010/108652, WO 2010/105110, WO 2010/105082, WO 2009/129246, WO 2009/018238, WO 2009/018233, WO 2008/089459, WO 2008/124085, WO 2008/076415, WO 2008/021389, WO 2010/051935, WO 2010/051933, WO 2009/129938, WO 2009/021887, WO 2008/101840, WO 2008/055236, WO 2010/003025, WO 2010/003022, WO 2007/096259, WO 2008/067481, WO 2008/024724, WO 2008/024725, or WO 2010/0145197; or a compound described in U.S. patent application publication, US 2008/0255133, US 2008/0058340, US 2009/0275606, or US 2009/0246198. In an exemplary embodiment, the MEK inhibitor is PD0325901.

In another aspect, the provides methods for primed-to-naïve resetting of at least one pluripotent stem cell, the method generally comprising culturing at least one pluripotent stem cell in the presence of at least one MEK inhibitor, at least one TNKS inhibitor, at least one PKC inhibitor, at least one ERK inhibitor, at least one ROCK inhibitor, Activin A, LIF, at least one glycogen synthase kinase (GSK-3) inhibitor, and at least one Src inhibitor. In some embodiments, the at least one pluripotent stem cell is cultured in the transient presence of the ROCK inhibitor. In certain embodiments, the at least one pluripotent stem cell is cultured in the presence of at least one MEK inhibitor, at least one TNKS inhibitor, at least one PKC inhibitor, at least one ERK inhibitor, at least one ROCK inhibitor, Activin A, LIF, at least one glycogen synthase kinase (GSK-3) inhibitor, and at least one Src inhibitor and then after some time the at least one pluripotent stem cell is cultured in the presence of at least one MEK inhibitor, at least one TNKS inhibitor, at least one PKC inhibitor, at least one ERK inhibitor, Activin A, LIF, at least one glycogen synthase kinase (GSK-3) inhibitor, and at least one Src inhibitor (i.e. without the ROCK inhibitor).

In some embodiments, the at least one pluripotent stem cell is cultured in the presence of at least one ROCK inhibitor from about 6 hours to about 30 hours. In certain embodiments, the at least one pluripotent stem cell is cultured in the presence of at least one ROCK inhibitor for about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, or about 30 hours. In an exemplary embodiment, the at least one pluripotent stem cell is cultured in the presence of at least one ROCK inhibitor for about 24 hours.

In some embodiments, the at least one pluripotent stem cell is cultured in the presence of at least one ROCK inhibitor and cultured in the absence of a ROCK inhibitor from about 12 hours to about 48 hours. In certain embodiments, the at least one pluripotent stem cell is cultured in the absence of ROCK inhibition for about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, or about 48 hours. In an exemplary embodiment, the at least one pluripotent stem cell is cultured in the presence of at least one ROCK inhibitor and cultured in the absence of a ROCK inhibitor for about 24 hours.

In another aspect the present disclosure provides methods for maintaining and/or passaging at least one pluripotent stem cell, the method generally comprises culturing at least one pluripotent stem cell in the presence of at least one MEK inhibitor, at least one TNKS inhibitor, at least one PKC inhibitor, at least one ROCK inhibitor, Activin A, LIF, at least one GSK-3 inhibitor, and at least one Src inhibitor, where the ROCK inhibitor is transiently present.

In certain embodiments, the GSK-3 inhibitor is one or more of CHIR98014, CHIR98023, BIO-acetoxime, BIO, LiCl, SB 216763, SB 415286, AR-A014418, 1-azakenpaull-one, bis-7-indolylmaleimide, kenpaullone, CT 99021, CT 20026, SB216763, SB 415286, TDZD-8, TIBPO (2-thio(3-iodobenzyl)-5-(1-pyridyl)-[I,3,4]-oxadiazole), IM12, CHIR99021 (6-[[2-[[4-(2,4-dichlorophenyl)-5-(5-methyl-1H-imidazole-2-yl)-2-pyrimidinyl]amino]ethyl]amino]-3-pyridinecarbonitrile; CAS registry number: 252917-06-9), BIO (6-bromoindirubin-3'-oxime; CAS registry number: 667463-62-9), Kenpaullone (9-bromo-7,12-dihydroindolo[3,2-d][1]benzazepin-6(5H)-one; CAS registry number: 142273-20-9), IM-16 (3-(4-fluorophenylethyl amino)-1-methyl-4-(2-methyl-1H-indole-3-yl)-1H-pyrrole-2,5-dione; CAS registry number: 1129669-05-1), a compound described in U.S. patent application publication, US 2013/0059385, US 2001/0034051, US 2002/0156087, US 2004/0092535, US 2004/0209878, US 2004/0138273, US 2004/0077707, US 2005/0054663, US 2006/0089369, a compound described in U.S. Pat. Nos. 6,057,117, 6,608,063, 6,417,185, 6,489,344, 6,153,618, a compound described in international PCT application publication, WO 2015/196072, WO/2003/049739, WO/2002/085909, WO/2003/011287, WO/2005/039485, and WO/2006/091737. In an exemplary embodiment, the GSK-3 inhibitor is IM12.

In certain embodiments, the Src inhibitor is one or more of WH-04, WH-4-023, SKI606 (bosutinib), dasatinib (SPYRCEL), saracatenib (AZD-0530), PP1, PP2, PD173955, AGL1872, PD162531, radicicol R2146, geldanamycin, a compound described in patent application publication, WO 2015/196072, US 2006/258686, US 2009/0227608, US 2010/0249152, and US 2013/0040972. In an exemplary embodiment, the Src inhibitor is WH-04.

In some embodiments, the above various inhibitors are included in a base media. Thus, the present disclosure provides cell culture media for inducing and/or maintaining naïve pluripotent stem cells.

In some embodiments, about 0.2-2 µM of MEK inhibitor is used in about 500 ml of culture medium. In some embodiments, the culture medium according to the disclosure comprises, consists essentially of, or consists of about 0.2-2 µM of MEK inhibitor, about 0.4-4 µM of TNKS inhibitor, about 0.4-4 µM of PKC inhibitor, about 0.5-5 µM of ERK inhibitor, about 2-20 µM of ROCK inhibitor, about 5-20 ng/mL Activin A, about 10-40 ng/mL LIF, about 0.2-1 µM GSK-3 inhibitor, and about 0.2-1 µM Src inhibitor. In some embodiments, the culture medium according to the disclosure comprises, consists essentially of, or consists of about 0.2-2 µM of MEK inhibitor, about 0.4-4 µM of TNKS inhibitor, about 0.4-4 µM of PKC inhibitor, about 0.5-5 µM of ERK inhibitor, about 5-20 ng/mL Activin A, about 10-40 ng/mL LIF, about 0.2-1 µM GSK-3 inhibitor, and about 0.2-1 µM Src inhibitor. In some embodiments, the culture medium according to the disclosure comprises, consists essentially of, or consists of about 0.2-2 µM of MEK inhibitor, about 0.4-4 µM of TNKS inhibitor, about 0.4-4 µM of PKC inhibitor, about 2-20 µM of ROCK inhibitor, about 5-20 ng/mL Activin A, about 10-40 ng/mL LIF, about 0.2-1 µM GSK-3 inhibitor, and about 0.2-1 µM Src inhibitor. In some embodiments, the culture medium according to the disclosure comprises, consists essentially of, or consists of about 0.2-2 µM of MEK inhibitor, about 0.4-4 µM of TNKS inhibitor, about 0.4-4 µM of PKC inhibitor, about 5-20 ng/mL Activin A, about 10-40 ng/mL LIF, about 0.2-1 µM GSK-3 inhibitor, and about 0.2-1 µM Src inhibitor.

In the each of the above embodiments, if a different kinase inhibitor that targets the same kinase is used, such kinase inhibitor may be used at a concentration that provides an approximately equivalent effect.

In some embodiments, the at least one pluripotent stem cell (e.g. human pluripotent stem cell (wherein hPS cells can comprise both human embryonic stem cells (hES) cells and human induced pluripotent stem cells (hiPS) cells) can be cultured until about 70% confluence at about 5% $O_2$, and about 5% $CO_2$.

In some embodiments, pluripotent stem cell culture may be grown on one layer of feeder cells. "Feeder cells" refer to a type of cell, which can be second species, when being co-cultured with another type of cell. Feeder cells are generally derived from embryo tissue or tire tissue fibroblast. Embryo is collected from the CF1 mouse of pregnancy 13 days, is transferred in 2 ml trypsase/EDTA, then careful chopping, 37 DEG C incubate 5 minutes. 10% FBS is added, so that fragment is precipitated, cell increases in 90% DMEM, 10% FBS and 2 mM glutamine. The feeder cells offer a growing environment for the ES cells. Certain form of ES cells can use, for example, primary mouse embryonic fibroblast or infinite multiplication mouse embryonic fibroblasts. In order to prepare feeder layer, irradiated cells may be used to support the ES cells (about 3000 rad γ-radiation will inhibit proliferation).

In some embodiments, the pluripotent stem cells culture may be grown without feeder cells, for example, in a cell culture vessel coated with at least one extracellular matrix protein (e.g., laminin or Matrigel).

The present disclosure reveals that MEK inhibitors can be efficiently replaced by inhibitors targeting either upstream (FGFR, RAF) or downstream (ERK) kinases. Furthermore, naïve hPSC self-renewal was optimally maintained by combining one of these FGF pathway inhibitors in combination with the tankyrase inhibitor XAV939, PKC inhibitor Gö6983, and ROCK inhibitor Y-27632 (XGY).

Transcriptional profiling revealed that naïve hPSCs maintained in the absence of MEK inhibitors acquired a pre-implantation epiblast state with elevated levels of ERK phosphorylation. This represents a developmental progression compared to naïve hPSCs in 5i/L/A, which correspond more closely to the inner cell mass, and suggests that the alternative naïve hPSCs may be more responsive to embryonic lineage cues. The alternative naïve hPSCs maintained without MEK inhibitors retained the potential to differentiate into trophoblast stem cells or re-enter the primed state of pluripotency. It was also observed that transfer from 5i/L/A to XGY-based naïve maintenance media may enhance the genomic stability of naïve hESCs, although subclonal aneuploidies were still observed in some of the alternative maintenance conditions.

Surprisingly, none of the alternative naïve maintenance conditions were capable of inducing naïve pluripotency in primed hPSCs. This led to the use of multiple FGF pathway inhibitors might facilitate primed-to-naïve resetting. Indeed, induction of naïve hPSCs was observed upon dual inhibition of MEK and ERK. This alternative naïve induction cocktail is referred to as PXGGY for PD0325901 (MEKi), XAV939 (TNKSi), Gö6983 (PKCi), GDC-0994 (ERKi), and Y-27362 (ROCKi). When combined with Activin A, this cocktail accelerated the activation of naïve-specific cell surface markers CD75 and SUSD2 in wild-type cells and more efficiently induced activation of a biallelic Xlinke fluorescent reporter system compared to the previously developed 5i/L/A cocktail.

The present disclosure also discloses several combinations of FGF pathway inhibitors that enable induction of naïve pluripotency in the absence of direct MEK inhibitors, including FGFRi+RAFi, FGFRi+ERKi, and RAFi+ERKi, in combination with XGY and Activin. This may provide a path to generate naïve hESCs in the absence of direct MEK inhibitors.

In some embodiments, the present disclosure provides a media for accelerated induction of naïve hPSCs from primed hPSCs: the PXGGY/A cocktail confers enhanced primed-to-naïve conversion efficiency, resulting in accelerated reprogramming kinetics as measured by flow cytometry for naïve-specific cell surface markers on day 10 and colony formation efficiency at passage 2 compared to the previously described 5i/L/A cocktail. This enables more widespread use of naïve stem cell technology by the research community.

In some embodiments, the present disclosure provides a media for maintaining naïve hPSCs in the absence of MEK inhibitors: the disclosure identified three cocktails of kinase inhibitors that can maintain naïve hPSCs in the absence of MEK inhibitors. These cocktails utilize individual FGF pathway inhibitors in combination with Tankyrase, PKC, and ROCK inhibitors (XGY) and are referred to as FXGY (containing the FGF receptor inhibitor PD166866), AXGY (containing the RAF inhibitor AZ628), and GXGY (containing the ERK inhibitor GDC-0994). Transcriptional profiling indicates that these alternative naïve hPSCs reside in a more advanced stage of pre-implantation epiblast development compared to 5i/L/A. In addition, naïve hPSCs maintained in AXGY responded more rapidly to media that induce capacitation into a formative state of pluripotency. Therefore, the alternative MEK inhibitor-independent naïve hPSCs may be more responsive to embryonic lineage cues.

In some embodiments, the present disclosure provides a media for inducing naïve hPSCs in the absence of MEK inhibitors: Since parent-specific methylation marks at imprinted loci were still erased using the PXGGY/A cocktail, we considered whether it might be possible to bypass the use of a direct MEK inhibitor during primed-to-naïve resetting by combining other FGF pathway inhibitors with Activin. Indeed, heterogeneous induction of some CD75/SUSD2 double positive cells was observed by treating primed hESCs with the FGFR inhibitor PD166866 in the presence of XGY and Activin. Furthermore, several combinations of FGF pathway inhibitors enabled more robust induction of naïve cells, including FGFRi+RAFi, FGFRi+ERKi, and RAFi+ERKi. These combinations were also able to induce biallelic expression of the X-linked MECP2 gene, although conversion kinetics were not as efficient as in PXGGY/A. This provides a path to generate naïve hESCs in the absence of direct MEK inhibitors.

The pluripotent stem cell can be maintained in culture for a time sufficient for maintenance, passage, or to change the pluripotency state of the cell to a more naïve state. In some embodiments, the at least one pluripotent stem cell is cultured for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, or at least 20 days. In some embodiments, the at least one pluripotent stem cell is cultured between 1-5 days, 1-10 days, 1-15 days, 1-20 days, 5-10 days, 5-15 days, 5-20 days, 10-15 days, 10-20 days, or 15-20 days. In some embodiments, the at least one pluripotent stem cell is cultured for at least about 5 days (e.g., about 10 days). In some embodiments, the culture medium is replenished as required during this time. In some embodiments, the cell is maintained in culture until the cell has at least one property which is similar to the corresponding property of mouse embryonic stem cells. In some embodiments, the at least one property which is similar to the corresponding property of mouse embryonic stem cells is the utilization of the distal OCT4 enhancer element. An important molecular signature of naïve pluripotency in the mouse system is the use of the distal enhancer (DE) of OCT4. Thus, in some embodiments, the cell is maintained in culture until the cell uses the distal Oct4 enhancer element for OCT4 expression. In some embodiments, the cell is maintained in culture until the cell uses the endogenous distal Oct4 enhancer element for OCT4 expression. In some embodiments, the cell is maintained in culture until the cell has enhanced utilization of the distal Oct4 enhancer element for OCT4 expression as compared to the cell prior to the culturing/maintenance period. In some embodiments, the cell is maintained in culture until the cell has enhanced utilization of the endogenous distal Oct4 enhancer element for OCT4 expression as compared to the cell prior to the culturing/maintenance period. The utilization of the distal OCT4 enhancer element can be tested using the OCT4-APE-GFP reporter system described in the Examples below.

In some embodiments, the at least one property which is similar to the corresponding property of mouse embryonic stem cells is colony morphology. Naïve pluripotent cells that correspond to the more immature "ground state" of pluripotency, exhibit a dome-like colony morphology. Thus, in certain embodiments, the cell is maintained in culture until it exhibits a dome-like colony morphology.

In some embodiments, the at least one property which is similar to the corresponding property of mouse embryonic stem cells is gene expression profile. The cell is maintained in culture until it has a global gene expression profile which clusters with naïve mouse ESCs as opposed to mouse EpiSCs and/or less naïve human ESCs. In some embodiments, the gene expression profile includes markers of ground state pluripotency, such as, but not limited to, NANOG, OCT4, DPPA5, DPP A3 (also known as STELLA), KLF4, KLF5, TFCP2L1, and/or REX1.

In some embodiments, at least 80% or at least 90% of the pluripotent stem cells of a colony, cell line, or cell culture express one or more marker(s), e.g., a set of markers, indicative of pluripotency, e.g., a ground state of pluripotency. In some embodiments at least 91%, at least 92%, at least 93%, at least 94%, at least 95%, at least 96%, at least 97%, at least 98%, at least 99%, or more of the cells of a colony, cell line, or cell culture express the marker(s).

Once generated, maintained and/or expanded the pluripotent stem cells or cells differentiated therefrom can be cryopreserved in accordance with the methods described below or known in the art.

In one embodiment, a pluripotent stem cell population can be divided and frozen in one or more bags (or units). In another embodiment, two or more hematopoietic progenitor cell populations can be pooled, divided into separate aliquots, and each aliquot is frozen. In a preferred embodiment, a maximum of approximately 4 billion nucleated cells is frozen in a single bag. In a preferred embodiment, the hematopoietic progenitor cells are fresh, i.e., they have not been previously frozen prior to expansion or cryopreservation. The terms "frozen/freezing" and "cryopreserved/cryopreserving" are used interchangeably in the present application. Cryopreservation can be by any method in known in the art that freezes cells in viable form. The freezing of cells is ordinarily destructive. On cooling, water within the cell freezes. Injury then occurs by osmotic effects on the cell membrane, cell dehydration, solute concentration, and ice crystal formation. As ice forms outside the cell, available water is removed from solution and withdrawn from the cell, causing osmotic dehydration and raised solute concentration which eventually destroys the cell. For a discussion, see Mazur, P., 1977, Cryobiology 14:251-272.

These injurious effects can be circumvented by (a) use of a cryoprotective agent, (b) control of the freezing rate, and (c) storage at a temperature sufficiently low to minimize degradative reactions.

Cryoprotective agents which can be used include but are not limited to dimethyl sulfoxide (DMSO) (Lovelock and Bishop, 1959, Nature 183:1394-1395; Ashwood-Smith, 1961, Nature 190:1204-1205), glycerol, polyvinylpyrrolidine (Rinfret, 1960, Ann, N.Y. Acad. Sci. 85:576), polyethylene glycol (Sloviter and Ravdin, 1962, Nature 196:548), albumin, dextran, sucrose, ethylene glycol, i-erythritol, D-ribitol, D-mannitol (Rowe et al., 1962, Fed. Proc. 21:157), D-sorbitol, i-inositol, D-lactose, choline chloride (Bender et al., 1960, J. Appl. Physiol. 15:520), amino acids (Phan The Tran and Bender, 1960, Exp. Cell Res. 20:651), methanol, acetamide, glycerol monoacetate (Lovelock, 1954, Biochem. J. 56:265), and inorganic salts (Phan The Tran and Bender, 1960, Proc. Soc. Exp. Biol. Med. 104:388; Phan The Tran and Bender, 1961, in Radiobiology, Proceedings of the Third Australian Conference on Radiobiology, Ilbery ed., Butterworth, London, p. 59). In a preferred embodiment, DMSO is used, a liquid which is nontoxic to cells in low concentration. Being a small molecule, DMSO freely permeates the cell and protects intracellular organelles by combining with water to modify its freezability and prevent damage from ice formation. Addition of plasma (e.g., to a concentration of 20-25%) can augment the protective effect of DMSO. After addition of DMSO, cells should be kept at 0° C. until freezing, since DMSO concentrations of about 1% are toxic at temperatures above 4° C.

A controlled slow cooling rate can be critical. Different cryoprotective agents (Rapatz et al., 1968, Cryobiology 5(1):18-25) and different cell types have different optimal cooling rates (see e.g., Rowe and Rinfret, 1962, Blood 20:636; Rowe, 1966, Cryobiology 3(1):12-18; Lewis, et al., 1967, Transfusion 7(1):17-32; and Mazur, 1970, Science 168:939-949 for effects of cooling velocity on survival of marrow-stem cells and on their transplantation potential). The heat of fusion phase where water turns to ice should be minimal. The cooling procedure can be carried out by use of e.g., a programmable freezing device or a methanol bath procedure.

Programmable freezing apparatuses allow determination of optimal cooling rates and facilitate standard reproducible cooling. Programmable controlled-rate freezers such as Cryomed or Planar permit tuning of the freezing regimen to the desired cooling rate curve. For example, for marrow cells in 10% DMSO and 20% plasma, the optimal rate is 1° to 3° C./minute from 0° C. to −80° C. In a preferred embodiment, this cooling rate can be used for CB cells. The container holding the cells must be stable at cryogenic temperatures and allow for rapid heat transfer for effective control of both freezing and thawing. Sealed plastic vials (e.g., Nunc, Wheaton cryules) or glass ampules can be used for multiple small amounts (1-2 ml), while larger volumes (100-200 ml) can be frozen in polyolefin bags (e.g., Delmed) held between metal plates for better heat transfer during cooling. Bags of bone marrow cells have been successfully frozen by placing them in −80° C. freezers which, fortuitously, gives a cooling rate of approximately 3° C./minute).

In an alternative embodiment, the methanol bath method of cooling can be used. The methanol bath method is well-suited to routine cryopreservation of multiple small items on a large scale. The method does not require manual control of the freezing rate nor a recorder to monitor the rate. In a preferred embodiment, DMSO-treated cells are pre-cooled on ice and transferred to a tray containing chilled methanol which is placed, in turn, in a mechanical refrigerator (e.g., Harris or Revco) at −80° C. Thermocouple measurements of the methanol bath and the samples indicate the desired cooling rate of 1° to 3° C./minute. After at least two hours, the specimens have reached a temperature of −80° C. and can be placed directly into liquid nitrogen (−196° C.) for permanent storage.

After thorough freezing, the pluripotent stem cells can be rapidly transferred to a long-term cryogenic storage vessel. In a preferred embodiment, samples can be cryogenically stored in liquid nitrogen (−196° C.) or its vapor (−165° C.). Such storage is greatly facilitated by the availability of highly efficient liquid nitrogen refrigerators, which resemble large Thermos containers with an extremely low vacuum and internal super insulation, such that heat leakage and nitrogen losses are kept to an absolute minimum.

Suitable racking systems are commercially available and can be used for cataloguing, storage, and retrieval of individual specimens.

Following cryopreservation, frozen pluripotent stem cells can be thawed in accordance with the methods described below or known in the art.

Frozen cells are preferably thawed quickly (e.g., in a water bath maintained at 37°-41° C.) and chilled immediately upon thawing. In a specific embodiment, the vial containing the frozen cells can be immersed up to its neck in a warm water bath; gentle rotation will ensure mixing of the cell suspension as it thaws and increase heat transfer from the warm water to the internal ice mass. As soon as the ice has completely melted, the vial can be immediately placed in ice.

In an embodiment of the disclosure, the hematopoietic progenitor cell sample as thawed, or a portion thereof, can be infused for providing hematopoietic function in a human patient in need thereof. Several procedures, relating to processing of the thawed cells are available, and can be employed if deemed desirable.

It may be desirable to treat the cells in order to prevent cellular clumping upon thawing. To prevent clumping, various procedures can be used, including but not limited to, the addition before and/or after freezing of DNase (Spitzer et al., 1980, Cancer 45:3075-3085), low molecular weight dextran and citrate, hydroxyethyl starch (Stiff et al., 1983, Cryobiology 20:17-24), etc.

The cryoprotective agent, if toxic in humans, should be removed prior to therapeutic use of the thawed hematopoietic progenitor cells. In an embodiment employing DMSO as the cryopreservative, it is preferable to omit this step in order to avoid cell loss, since DMSO has no serious toxicity.

However, where removal of the cryoprotective agent is desired, the removal is preferably accomplished upon thawing.

One way in which to remove the cryoprotective agent is by dilution to an insignificant concentration. This can be accomplished by addition of medium, followed by, if necessary, one or more cycles of centrifugation to pellet cells, removal of the supernatant, and resuspension of the cells. For example, intracellular DMSO in the thawed cells can be reduced to a level (less than 1%) that will not adversely affect the recovered cells. This is preferably done slowly to minimize potentially damaging osmotic gradients that occur during DMSO removal.

After removal of the cryoprotective agent, cell count (e.g., by use of a hemocytometer) and viability testing (e.g., by trypan blue exclusion; Kuchler, 1977, Biochemical Methods in Cell Culture and Virology, Dowden, Hutchinson & Ross, Stroudsburg, Pa., pp. 18-19; 1964, Methods in Medical Research, Eisen et al., eds., Vol. 10, Year Book Medical Publishers, Inc., Chicago, pp. 39-47) can be done to confirm cell survival. Accordingly, they can be used for (1) induction of differentiation into desired various cells, (2) screening of candidate compounds for pharmaceutical agents using the differentiation-induced cells; (3) generation of tissue for regeneration medicine from the differentiation-induced cells, (4) transplantation of the generated tissue into a patient; (5) an organ regeneration method by transplantation of naïve-state iPS cells into blastocysts, and the like.

In the present disclsoure, cells capable of induction of differentiation of the naïve pluripotent stem cells are not particularly limited, and examples thereof include cardiomyotic cell, a nerve cell, insulin-production cell, glomerulus endothelial cell, mesangium cell, Bowman's epithelial cell, and blood vessel endothelial cell.

In the present disclsoure, a method for differentiation-inducing the naïve pluripotent stem cells is not particularly limited, and examples of a method for differentiation-inducing into the nerve cell include a SDIA (Stromal cell-Derived Inducing Activity) method (Proceedings of the National Academy of Sciences of the United States of America, Vol. 99, No. 3, 1580-1585, 2002).

In the present disclsoure, cells that have been differentiation-induced using naïve pluripotent stem cells can be used for screening drug candidate compounds for various diseases. For example, by adding the drug candidate compounds singly or in combination with other drugs into the differentiation-induced cells, the morphology or functional change of the cells, increase and decrease of various factors, gene expression profiling, and the like, are detected so as to carry out evaluation. Herein, the cells are preferably cells having the same phenotype as that of disease to be treated, and more preferably cells differentiation-induced from the naïve pluripotent stem cells produced from somatic cells derived from a patient having a disease.

In the present disclosure, tissue can be generated from differentiation-induced cells using naïve pluripotent stem cells, and the generated tissue can be used in the field of the regeneration medicine. For example, damaged nerve tissue can be normalized by replacing the damaged nerve tissue by normal tissue derived from nerve tissue of present invention. This makes it possible to cure diseases derived from damaged nerve cells. Examples of such diseases include Parkinson's disease, Alzheimer's disease, retinal pigmentary degeneration, amyotrophic lateral sclerosis, optic neuromyelitis, optic neuritis, acute disseminated encephalomyelitis, allergic encephalomyelitis, spinal cord damage, transverse myelitis, spinocerebellar degeneration, chronic inflammatory demyelinating encephalopathy (CIDP), Guillain-Barre syndrome, multiple sclerosis, epilepsy, Parkinson's syndrome, Down syndrome, schizophrenic disorder, neurodystonia, Huntington's disease, age-related macular degeneration, and inner ear deafness.

In the present invention, as a transplanting method of the generated tissue into a patient, although obvious to a person skilled in the art, for example, when nerve cells are transplanted, transplantation can be carried out according to the method described in Nature Neuroscience, Vol. 2, No. 12, page 1137-1140, 1999.

In a specific embodiment, the stem cell population administered to a human patient in need thereof can be a pool of two or more samples derived from a single human. As used herein the terms "patient" and "subject" are used interchangeably.

The disclosure provides methods of treatment by administration to a patient of a pharmaceutical (therapeutic) composition comprising a therapeutically effective amount of recombinant or non-recombinant pluripotent stem cells produced by the methods of the present invention as described herein above.

The present disclosure provides pharmaceutical compositions. Such compositions comprise a therapeutically effective amount of the pluripotent stem cells or cells derived therefrom, and a pharmaceutically acceptable carrier or excipient. Such a carrier can be but is not limited to saline, buffered saline, dextrose, water, glycerol, ethanol, and combinations thereof. The carrier and composition preferably are sterile. Suitable pharmaceutical carriers are described in Remington: The Science and Practice of Pharmacy, 21st Edition, David B. Troy, ed., Lippicott Williams & Wilkins (2005), which is incorporated by reference herein in its entirety, and specifically for the material related to pharmaceutical carriers and compositions. The pharmaceutical compositions described herein can be formulated in any manner known in the art.

The formulation should suit the mode of administration. Pluripotent stem cells can be resuspended in a pharmaceutically acceptable medium suitable for administration to a mammalian host. In preferred embodiments, the pharmaceutical composition is acceptable for therapeutic use in humans. The composition, if desired, can also contain pH buffering agents.

The pharmaceutical compositions described herein can be administered via any route known to one skilled in the art to be effective. In a preferred embodiment, the composition is formulated in accordance with routine procedures as a pharmaceutical composition adapted fir intravenous administration to a patient (e.g., a human). Typically, compositions for intravenous administration are solutions in sterile isotonic aqueous buffer. Where necessary, the composition may also include a solubilizing agent and a local anesthetic such as lidocaine to ease pain at the site of the injection.

In specific embodiments, the compositions described herein are formulated for administration to a patient with one or more additional therapeutic active ingredients.

In some embodiments a pluripotent cell described herein is used to prepare a composition for cell therapy to be administered to a vertebrate subject, e.g., a non-human animal, or a human. In some embodiments, a pluripotent cell derived or cultured according to the systems and methods described herein is used to prepare a composition for cell therapy to be administered to a vertebrate subject, e.g., a non-human animal, or a human. In some embodiments, the composition comprises autologous cells. In other embodiments, the composition comprises non-autologous cells. In some embodiments, the cells are genetically matched to an individual.

The naïve pluripotent stem cells may be used to treat a number of life-threatening diseases and disorders. Examples include, but are not limited to, cancers (such as, but not limited to, acute leukemia, chronic leukemia, high-risk solid tumors, Hodgkin & Non-Hodgkin Lymphoma, myelodysplasia syndromes), blood disorders (such as, but not limited to, aplastic anemia, beta thalassemia, Diamond-Blackfan Anemia, Fanconi Anemia, Sickle Cell Disease), immune disorders (such as, but not limited to, chronic granulomatous disease, hystiocytic disorders, leukocyte adhesion deficiency, severe combined immunodeficiency diseases, Wiskott-Aldrich Syndrome), and metabolic disorders (such as, but not limited to, Krabbe Disease, Hurler Syndrome, Metachromatic Leukodystrophy, and Sanfilippo Syndrome). The naïve pluripotent stem cells produced by the methods described herein are administered to a subject having or suspected of having a disease or disorder that can be treated using stem cell therapy. Several approaches may be used for the introduction of the naïve pluripotent vertebrate stem cells stem cells into the subject, including but not limited to, catheter-mediated delivery I.V. (e.g., endovascular catheter), direct injection into a target site, intravenous injection, intraperitoneal injection, parenteral injection, subcutaneous injection, intramuscular injection, and/or intracardiac injection.

The compositions and methods of the disclosure may be applied to derive or culture naïve pluripotent cells from non-human animals including but not limited to, dogs, cats, horses, sheep, goats, cows, and/or rodents (such as rats, rabbits, hamsters, guinea pigs). The disclosure may be applied to derive or culture naïve pluripotent cells from primates, e.g., non-human primates, or humans. In many embodiments, the vertebrate is a mammal. In some embodiments the mammal is a bovine, ovine, caprine, equine, canine, or feline. It is also envisioned that compositions and methods of the invention may be used to derive naïve pluripotent cells, e.g., ES cells or iPS cells from non-mammalian vertebrates, e.g., zebrafish or other non-mammalian organisms of interest such as birds. In some embodiments, if the species is one from which ES or iPS cells have not heretofore been derived, techniques and culture conditions can be adapted from standard techniques used in other species, e.g., related species.

Systems, compositions, and methods of the invention can be applied in the derivation or culture of naïve pluripotent cells derived from cells obtained from any of a variety of sources. For example, cells obtained from the inner cell mass (ICM) or epiblast can be used to derive naïve ES cells. In some embodiments, the systems, compositions, and methods are applied to derive naïve pluripotent stem cells from blastomeres, e.g., blastomeres isolated from a morula or from a 4-8 cell stage embryo. In some embodiments, the compositions and methods are applied to derive naïve pluripotent stem cells from germ cells. In some embodiments the compositions and methods are used to derive naïve pluripotent cells using parthenogenesis or SCNT. In some embodiments the methods are applied to derive or culture naïve induced pluripotent stem (iPS) cells. Methods for generating iPS cells are well-known in the art (see, for example, WO2013159103, WO 2013177133, and U.S. Pat. No. 8,748,179). iPSCs are typically derived by introducing a specific set of pluripotency-associated genes, or "reprogramming factors", into a given cell type. The original set of reprogramming factors are the genes Oct4 (Pou5f1), Sox2, cMyc, and Klf4. While this combination is most conventional in producing iPSCs, each of the factors can be functionally replaced by related transcription factors, miRNAs, small molecules, or even non-related genes such as lineage specifiers. In some embodiments, somatic cells used to generate iPS cells include, but are not limited to, fibroblasts, keratinocytes, immune system cells, and epithelial cells. In some embodiments, iPS cells are generated without genomic modification. In some embodiments, iPS cells are free of exogenously introduced DNA. For example, they may be generated using synthetic modified mRNA, small molecules, or a combination thereof. For example, iPS cells may be generated using the methods described in Mandal, P K & Rossi, D J, Nature Protocols 8, 568-582 (2013). In some embodiments, iPS cells are generated using episomal expression of one or more of the reprogramming factors. After the iPS cells are generated, the episome(s) may be lost resulting in cells free of exogenously introduced DNA.

The invention contemplates a variety of uses for the pluripotent cells, cell lines derived, cultured, or generated as described herein. In general, pluripotent cells may be used for any purpose contemplated in the art for use of pluripotent cells, e.g., ES or iPS cells. See, e.g., international PCT applications, no. PCT/US2013/050077 (WO 2014/011881) and PCT/US2001/006912 (WO 2001/066697).

In some embodiments a pluripotent cell derived or cultured according to the invention is used to produce one or more differentiated cells. Such cells are considered to be an aspect of the disclosure. The cells could be, e.g., multipotent stem cells or fully differentiated cells. The cells may be, e.g., hematopoietic cells (e.g., of the myeloid or erythroid lineage), neural cells (e.g., neural precursors, neurons or glial cells), myoblasts, myocytes, cardiomyocytes, melanoblasts, keratinocytes, chondroblasts, chondrocytes, osteoblasts, osteoclasts, pancreatic beta cells, retinal cells, endothelial cells, etc. Protocols known in the art for differentiating cells into cells of a desired type may be used (see, for example, US 20130273651). In some embodiments a pluripotent cell may be differentiated to a cell type of interest ex vivo, e.g., before being administered to a subject. For example, a pluripotent cell may be differentiated to produce cells of a cell type that is affected by a disease or that may be useful in treating a disease for which the subject is in need of treatment. In some embodiments cells are used to generate a tissue or organ in vitro or to supplement a tissue or organ in vivo.

The disclosure also provides methods of producing non-human vertebrates, e.g., non-human mammals, which can be genetically modified or non-genetically modified, using the pluripotent cells of the disclosure. Such non-human vertebrates are aspects of the disclosure. In some embodiments the non-human vertebrates are mice. In some embodiments, non-human mammals are produced using methods known in the art for producing non-human mammals from ES or iPS cells (see, for example, WO 2010124290). For example, ES or iPS cells are introduced into a blastocyst of the same species which is transferred to a suitable foster mother (e.g., a pseudopregnant female of the same species) under conditions suitable for production of live offspring. If a diploid blastocyst is used, chimeric offspring may be produced, which are typically derived in part from the ES cell or iPS cell and in part from the blastocyst into which the cell was introduced. Chimeric offspring may be interbred to generate homozygous animals if the chimeric offspring contain ES-derived contribution to the germ line as known in the art. In some embodiments, the mice are produced using methods that do not require production of chimera or chimeric offspring. In some embodiments, pluripotent ES cells are introduced into tetraploid blastocysts of the same vertebrate species under conditions that result in production of an embryo (at least one/one or more embryos) and the resulting embryo(s) transferred into an appropriate foster mother, such as a pseudopregnant female of the same vertebrate species. The resulting female is maintained under conditions that result in development of live offspring, thereby producing a non-human mammal derived from the introduced ES cells. See, e.g., U.S. Pat. No. 6,784,336. In some embodiments, the mouse is produced by a method that involves laser-assisted injection or piezo-injection of ES cells of the invention into four- or eight-cell embryos. In some embodiments the mouse is produced without need to generate a chimera, e.g., using methods described in international PCT application, no. PCT/EP2003/002180 (WO 2003/073843). Another embodiment of the present invention is a method of producing a non-human mammalian strain, such as a mouse strain, e.g., a genetically engineered mouse strain, that is derived from a given (single) iPS or ES cell clone of the present disclosure without outcrossing with a wild type partner. See, e.g., U.S. Pat. No. 6,784,336. In some embodiments the mice are genetically modified, e.g., they are derived from an ES or iPS cell that is genetically modified. The invention contemplates interbreeding non-human vertebrates, e.g., mice, derived from the ES cells or iPS cells with mice of any strain of interest, the resulting strains being considered other aspects of the invention.

A naïve pluripotent cell can be derived from a cell, e.g., a somatic cell, obtained from an individual of interest. The individual can be, e.g., a human suffering from a disease or condition. In some embodiments the individual is immunocompatible with an individual suffering from a disease or condition. In some embodiments the disease is a neurodegenerative disease, e.g., Parkinson's disease, Alzheimer's disease, or amyotrophic lateral sclerosis. In some embodiments the individual suffers from diabetes. In some embodiments the individual suffers from heart failure or a muscle disorder or an enzyme deficiency, sickle cell anemia, hemophilia, a glycogen storage disorder, or cystic fibrosis. In some embodiments the disease is a heritable disease. In some embodiments the disease is a monogenic disorder. In some embodiments the disease has an autosomal dominant inheritance pattern. In some embodiments the disease has an autosomal recessive inheritance pattern. In some embodiments the disease is sporadic, i.e., there is no evident pattern of inheritance. In some embodiments the individual has suffered an injury, e.g., traumatic brain injury, spinal cord injury. In some embodiments the individual is in need of cell therapy.

In some embodiments a naïve pluripotent cell, e.g., a naïve pluripotent human cell, is derived from a cell (e.g., a somatic cell) obtained from an individual who harbors a mutation or genetic variation that is known to cause or suspected of causing a disease (or an immunocompatible donor). The mutation or genetic variation is corrected ex vivo. Resulting cells or cells derived therefrom are administered to the subject.

In some embodiments, a naïve pluripotent cell, e.g., a naïve pluripotent human cell, may be used to generate a model of a disease, e.g., an animal model or a cellular model of a disease, e.g., any of the diseases mentioned herein or other diseases of interest. In some embodiments the naïve pluripotent cell is derived from a cell, e.g., a somatic cell, obtained from an individual who has the disease. In some embodiments the naïve pluripotent cell is genetically engineered to harbor a mutation or genetic variation that is known to cause or suspected of causing the disease. In some embodiments the naïve pluripotent cell may be differentiated to a cell of a cell type that is affected by the disease.

In some embodiments, a naïve pluripotent cell is not genetically modified. In some embodiments, the naïve pluripotent cell is devoid of DNA or genetic alterations (e.g., insertions, substitutions, deletions) introduced by the hand of man. In some embodiments, a naïve pluripotent cell may be genetically modified after it is derived. Any of a variety of different methods may be employed to genetically modify a naïve pluripotent cell or a cell derived therefrom, e.g., a differentiated cell. Examples of such methods include, but are not limited to, homologous recombination and transfection (see, for example, WO 2013042731, and U.S. Pat. No. 8,637,311). In some embodiments, genome editing technologies such as, but not limited to zinc fingers, TALENs, CRISPR/Cas systems are used to genetically modify the naïve pluripotent cell.

Another aspect of the present disclosure provides a kit for generating a cell culture medium according to the disclosure. In some the kit includes instructions for making the cell culture medium including inhibitor concentrations and/or storage instructions, inhibitors and basal media as discussed above.

When introducing elements of the present disclosure or the preferred aspects(s) thereof, the articles "a," "an," "the," and "said" are intended to mean that there are one or more of the elements. The terms "comprising," "including," and "having" are intended to be inclusive and mean that there may be additional elements other than the listed elements.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," $5^{th}$ Ed., Smith, M. B. and March, J., eds. John Wiley & Sons, New York: 2001, the entire contents of which are hereby incorporated by reference.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as Molecular Cloning: A Laboratory Manual, second edition (Sambrook, et al., 1989) Cold Spring Harbor Press; Oligonucleotide Synthesis (M. J. Gait, ed. 1984); Methods in Molecular Biology, Humana Press; Cell Biology: A Laboratory Notebook (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); DNA Cloning: A practical Approach, Volumes I and II (D. N. Glover ed. 1985); Nucleic Acid Hybridization (B. D. Hames & S. J. Higgins eds.(1985»; Transcription and Translation (B. D. Hames & S. J. Higgins, eds. (1984»; Animal Cell Culture (R. I. Freshney, ed. (1986»; Immobilized Cells and Enzymes (IRL Press, (1986»; and B. Perbal, A practical Guide To Molecular Cloning (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Probing the Signaling Requirements for naïve Human Pluripotency by High-throughput Chemical Screening A major objective in stem cell research is to devise in vitro culture conditions for pluripotent stem cells (PSCs) that recapitulate specific stages of embryonic development. The use of MEK and GSK3 inhibitors and leukemia inhibitory factor (2i/LIF) captures mouse embryonic stem cells (ESCs) in a "naïve" state of pluripotency that closely corresponds to the pre-implantation epiblast at embryonic day (E) 4.5. This naïve state of pluripotency contrasts with the "primed" pluripotent state observed in mouse epiblast stem cells (EpiSCs), which aligns more closely with the anterior primitive streak of the late-gastrula stage embryo. Overlapping biological and molecular features between human PSCs (hPSCs) and mouse EpiSCs lend support to the notion that hPSCs adopt a primed pluripotent identity when derived under conventional conditions. Indeed, transcriptome profiling of primate embryos confirmed that conventional hPSCs most closely correlate with the late post-implantation epiblast. Nevertheless, recent work indicates that a subpopulation of conventional hPSCs with high self-renewal capacity displays properties more aligned with the early post-implantation epiblast. Conventional hPSCs also exhibit some primate-specific features that are not observed in either mouse ESCs or EpiSCs, such as expression of N-cadherin at colony boundaries.

Over the past decade, a number of groups have attempted to induce features of naïve pluripotency in hPSCs using chemical and genetic approaches. Based on comparisons to single cell RNA sequencing (scRNA-seq) data from human and non-human primate embryos, naïve cells derived in two specific culture conditions display particularly strong transcriptional signatures of the pre-implantation embryo: t2i/L/Gö, which consists of titrated 2i/LIF and a PKC inhibitor, and 5i/L/A, which consists of MEK, GSK3, BRAF, SRC, and ROCK inhibitors together with LIF and activin A. Naïve hPSCs have provided a cellular model system to investigate human-specific mechanisms of X chromosome regulation and the role of transposable elements (TEs) that are associated with early embryogenesis. In addition, recent findings indicate that these cells also harbor the ability to acquire extraembryonic fates and give rise to human blastocyst-like structures.

Despite the progress cited above, important questions remain about the nature of human pluripotent states and the utility of naïve hPSCs in regenerative medicine. Naïve hPSCs derived in t2i/L/Gö or 5i/L/A exhibit a global loss of imprinting and extended culture in 5i/L/A leads to genomic instability. This has been attributed to global DNA hypomethylation resulting from the use of a MEK1/2 inhibitor, PD0325901, which is a near-universal component of naïve stem cell protocols described to date. While a SRC inhibitor could replace the MEK inhibitor in mouse ESCs, it was unable to do so in naïve hPSCs. In addition, titration of MEK inhibition was reported to enhance the genomic stability of naïve hPSCs in 5i/L/A but was not tolerated in t2i/L/Gö, suggesting that MEK inhibition is essential for the naïve state of human pluripotency. The present example, performed high-throughput chemical screening to discover alternative compounds that can maintain naïve human pluripotency in the absence of MEK1/2 inhibitors. GSK3 inhibition was also omitted as naïve hPSCs cultured in the absence of a GSK3 inhibitor maintained a naïve-specific transcriptome. The present example provides distinct signaling requirements for induction and maintenance of naïve human pluripotency and provides a basis for refinement of naïve culture regimes.

Methods

Cell lines and culture conditions: Primed hESCs (H9, WIBR3, WIBR3 OCT4-ΔPE-GFP, WIBR3 MECP2-GFP/tdTomato) were cultured in mTeSR Plus (STEMCELL Technologies, 100-0276) on Matrigel (Corning, 354277) coated wells and passaged using ReLeSR (STEMCELL Technologies, 05872) or dissociated with Dispase (STEMCELL Technologies, 07923) and passaged by cutting colonies into small, uniform squares with Stem Pro EZPassage Stem Cell Passaging Tool (GIBCO, 23181010) every 4 to 6 days. Primed hESCs were fed with fresh media every second day and were cultured in 5% $CO_2$ and 20% $O_2$ at 37° C. Naïve hESCs were cultured in 5% $CO_2$ and 5% $O_2$ at 37° C. in 5i/L/A or alternative culture conditions. 5i/L/A media were prepared by combining N2B27 and the following small molecules and cytokines as previously described: 1 µM PD0325901 (Stemgent, 04-0006), 1 µM IM-12 (Enzo, BML-WN102), 0.5 µM SB590885 (Tocris, 2650), 1 µM WH-4-023 (A Chemtek, H620061), 10 µM Y-27632 (Peprotech, 1293823), 20 ng/mL recombinant human LIF (PeproTech, 300-05) and 10 ng/mL Activin A (Peprotech, 120-14). 500 mL N2B27 was generated by combining: 240 mL DMEM/F12 (GIBCO, 11320), 240 mL Neurobasal (GIBCO, 21103), 5 mL N2 100× supplement (GIBCO, 17502), 10 mL B27 50× supplement (GIBCO, 17504), 1× GlutaMAX, 1× MEM NEAA (GIBCO, 11140), 0.1 mM β-mercaptoethanol (Millipore Sigma, 8.05740), 1% penicillin-streptomycin, and 50 µg/ml BSA Fraction V (GIBCO, 15260). All tissue culture experiments were performed in 6-well plates unless stated otherwise. Media were filtered using a 0.22 µm filter and cell lines were regularly tested for mycoplasma contamination. Detailed information on conditions used for defining alternative naïve induction and maintenance media can be found in the Method details below and in Tables 1-6.

TABLE 1

Figure 2A:
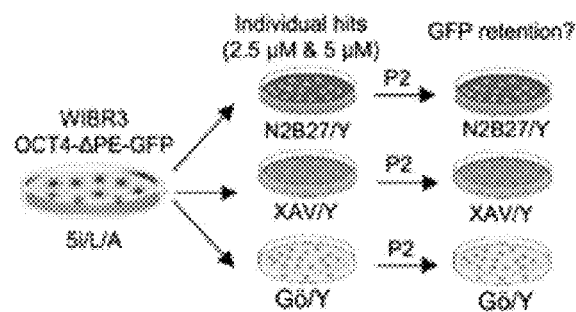
FIG. 2A-2H show defining the activity of selected hit compounds during extended maintenance assays for naïve human pluripotency.
Figure 2B:
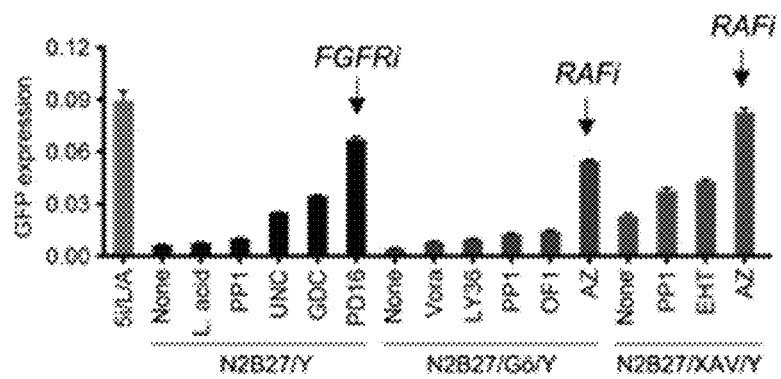

Media compositions 1 - Validation of screening hits during extended
naïve hESC culture in separate base media (Related to FIG. 2A-B)

| Base media N2B27+ | Compounds | | | | | |
|---|---|---|---|---|---|---|
| Y-27632 (10 μM Y-27632) | Laccaic Acid A | GDC-0994 | PD166866 | 1-Naphtyhl PP1 | Semapimod | UNC0638 |
| | Concentration 2.5 μM 5 μM | Concentration 2.5 μM 5 μM | Concentration 2.5 μM 5 μM | Concentration 2.5 μM 5 μM | Concentration 2.5 μM 5 μM | Concentration 2.5 μM 5 μM |
| XAV/Y (2 μM XAV939 and 10 μM Y-27632) | LDC000067 | Brequinar | AZ628 | 1-Naphtyhl PP1 | Semapimod | EHT 1864 |
| | Concentration 2.5 μM 5 μM | Concentration 2.5 μM 5 μM | Concentration 2.5 μM 5 μM | Concentration 2.5 μM 5 μM | Concentration 2.5 μM 5 μM | Concentration 2.5 μM 5 μM |
| Gö/Y (2 μM Gö6983 and 10 μM Y-27632) | OF-1 | Vorapaxar | AZ628 | 1-Naphtyhl PP1 | LY364947 | |
| | Concentration 2.5 μM 5 μM | Concentration 2.5 μM 5 μM | Concentration 2.5 μM 5 μM | Concentration 2.5 μM 5 μM | Concentration 2.5 μM 5 μM | |

TABLE 2

Media compositions 2 - Validation of screening hits during extended
naïve hESC culture in XAV/Gö/Y base media

| Base media | Compound | Concentration |
|---|---|---|
| XAV/Gö/Y (2 μM XAV939, 2 μM Gö6983, and 10 μM Y-27632 in N2B27) | OF-1 | 2.5 μM |
| | LDC000067 | 2.5 μM |
| | Brequinar | 2.5 μM |
| | Laccaic Acid A | 2.5 μM |
| | GDC-0994 | 2.5 μM |
| | PD166866 | 2.5 μM |
| | UNC0638 | 2.5 μM |
| | Semapimod | 2.5 μM |
| | Vorapaxar | 2.5 μM |
| | EHT 1864 | 2.5 μM |
| | 1-Naphtyhl PP1 | 2.5 μM |
| | LY364947 | 2.5 μM |
| | ICI 118,551 hydrochloride | 2.5 μM |
| | BMX-IN-1 | 2.5 μM |
| | J113863 | 2.5 μM |
| | NSC 109555 ditosylate | 2.5 μM |
| | Erlotinib | 2.5 μM |
| | Sapitinib | 2.5 μM |
| | MPEP Hydrochloride | 2.5 μM |
| | GSK2033 | 2.5 μM |
| | GS-493 | 2.5 μM |

TABLE 3

Media compositions 3 - Alternative naïve maintenance
conditions (Related to FIG. 2 and FIG. 4)

| | Composition: N2B27+ | | | | | | |
|---|---|---|---|---|---|---|---|
| Media | WH4-023 | IM-12 | SB590885 | AZ628 | Y-27632 | LIF | ActA |
| a5i/L/A | 1 μM | 1 μM | 0.5 μM | 5 μM | 10 μM | 20 ng/ml | 10 ng/ml |

| | Composition: N2B27+ | | | | | | | |
|---|---|---|---|---|---|---|---|---|
| Media | PD0325901 (P) | PD166866 (F) | AZ628 (A) | GDC-0994 (G) | UNC0638 (U) | XAV939 (X) | Gö6983 (G) | Y-27632 (Y) |
| FXGY | | 1 μM | | | | 2 μM | 2 μM | 10 μM |
| AXGY | | | 5 μM | | | 2 μM | 2 μM | 10 μM |
| AXGYU | | | 5 μM | | 1 μM | 2 μM | 2 μM | 10 μM |
| PXGY | 1 μM | | | | | 2 μM | 2 μM | 10 μM |
| GXGY | | | | 5 μM | | 2 μM | 2 μM | 10 μM |

TABLE 4

Figure 5A:
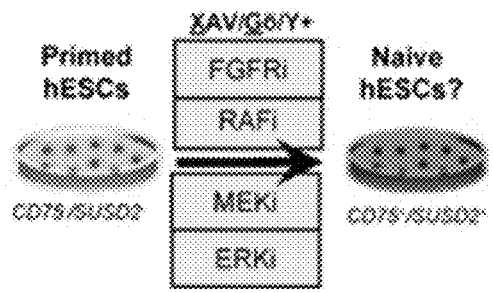
FIG. 5A-5K shows examining the signaling requirements for primed-to-naïve resetting.
Figure 5B:
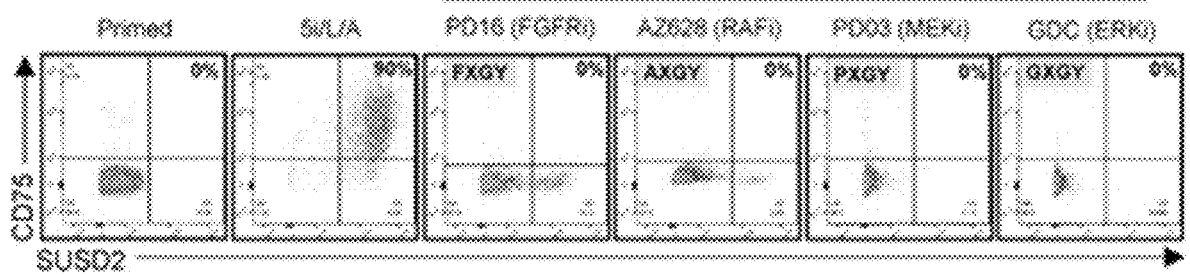
Figure 5C:
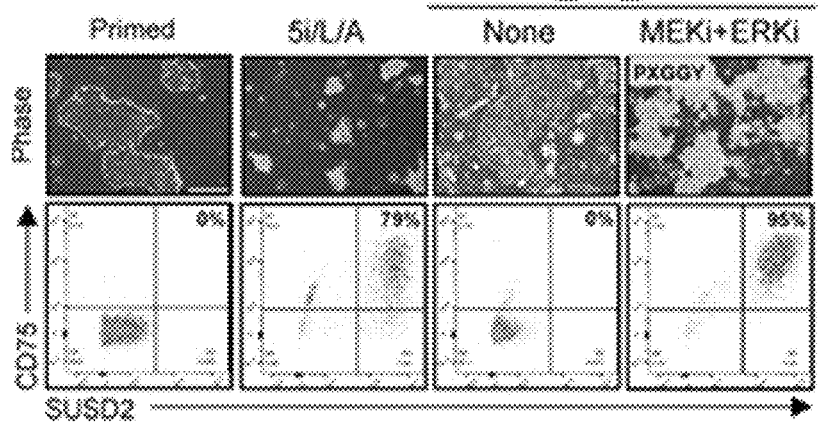

Media compositions 4 - Examining the potential of multiple FGF pathway inhibitors to achieve primed-to-naïve resetting (Related to FIG. 5C)

| Media Abbreviation | Media Detail | | XAV939 (X) | Gö6983 (G) | Y-27632 (Y) | PD166866 (F) | PD0325901 (P) | AZ628 (A) | GDC-0994 (G) |
|---|---|---|---|---|---|---|---|---|---|
| FXGPY | XAV/Gö/Y+ | PD16 (FGFR1i) + PD03 (MEKi) | 2 μM | 2 μM | 10 μM | 1 μM | 1 μM | | |
| AXGPY | | AZ628 (RAFi) + PD03 (MEKi) | 2 μM | 2 μM | 10 μM | | 1 μM | 5 μM | |
| PXGGY | | GDC (ERKi) + PD03 (MEKi) | 2 μM | 2 μM | 10 μM | | 1 μM | | 2.5 μM |
| AXGGY | | AZ628 (RAFi) + GDC (ERKi) | 2 μM | 2 μM | 10 μM | | | 5 μM | 2.5 μM |
| FXGGY | | PD16 (FGFRi) + GDC (ERKi) | 2 μM | 2 μM | 10 μM | 1 μM | | | 2.5 μM |

TABLE 5

Figure 5D:
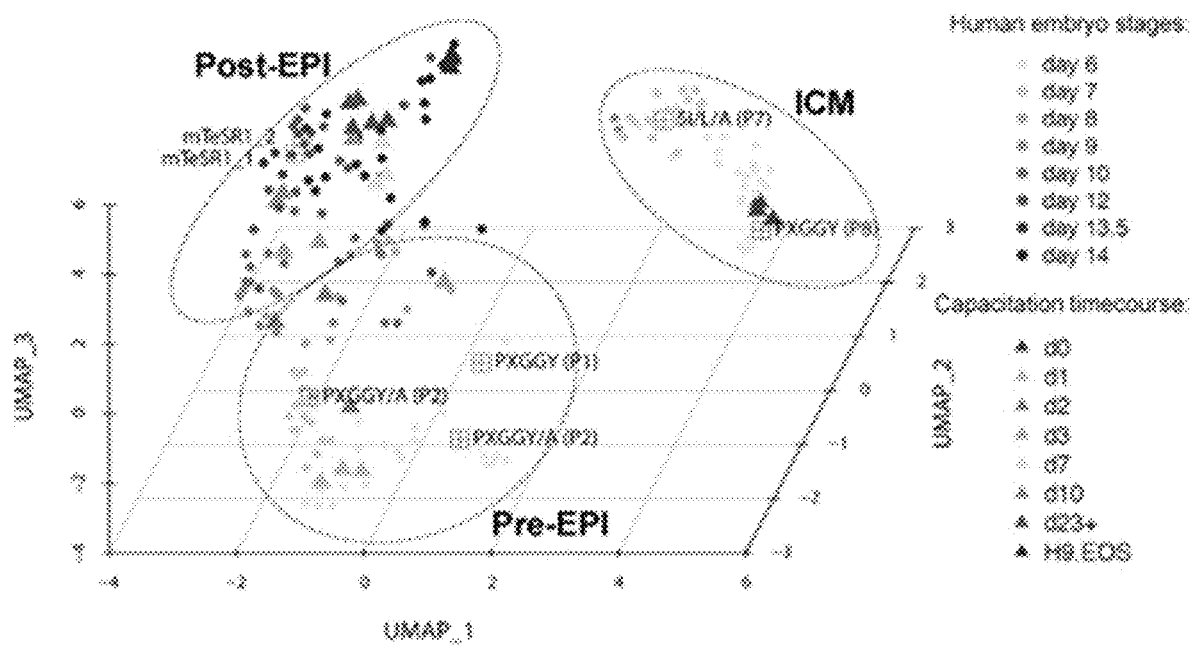
Figure 5E:
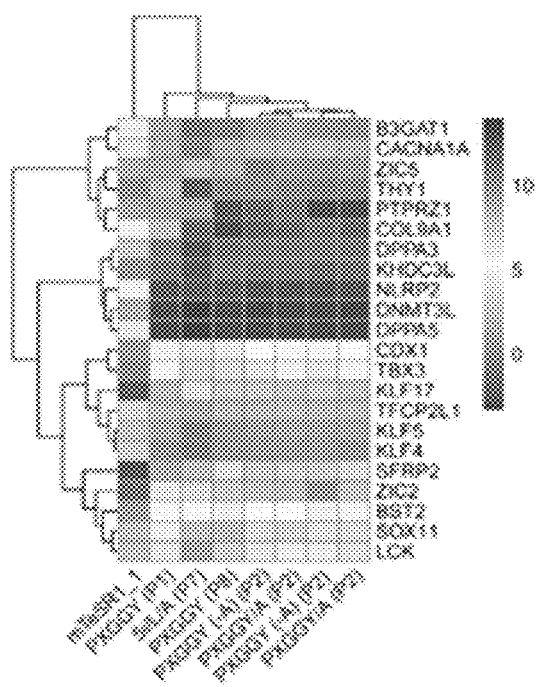
Figure 5F:
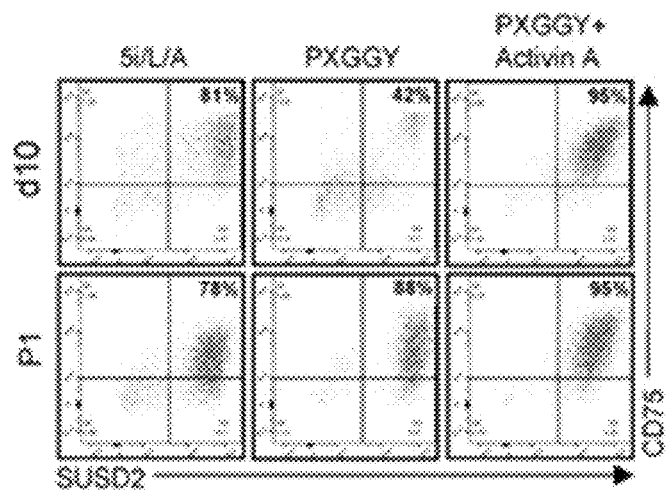
Figure 5G:
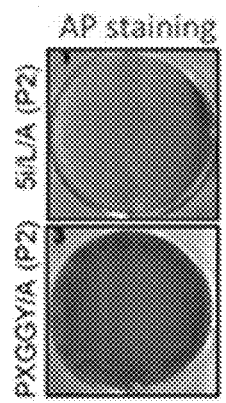
Figure 5H:
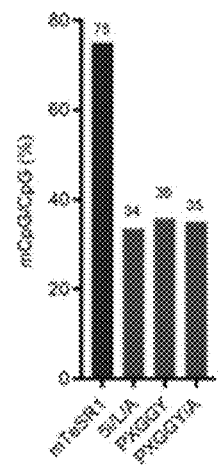
Figure 5I:
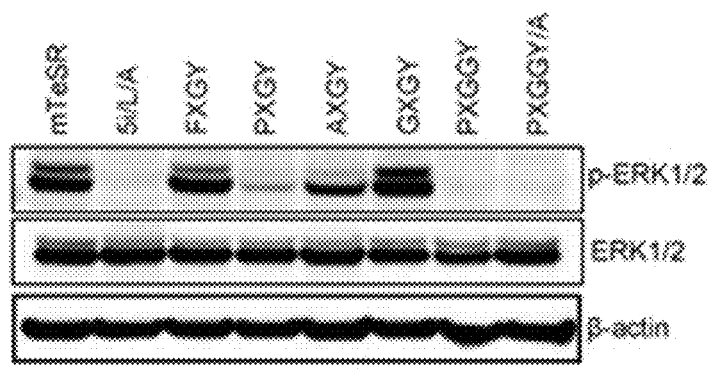
Figure 5J:
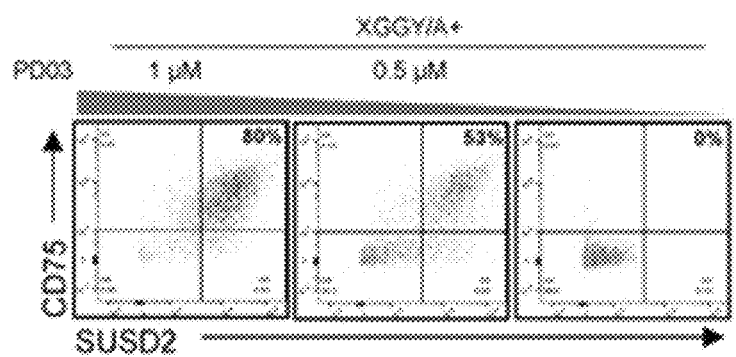
Figure 5K:
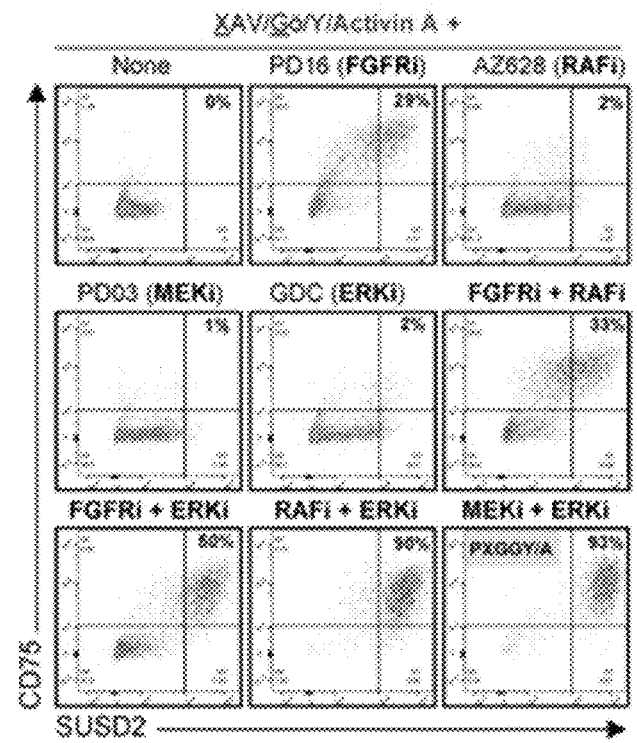

Media compositions 5 - Examining the potential of multiple FGF pathway inhibitors to achieve resetting in the presence of Activin (Related to FIG. 5K)

| Media Abbreviation | Media Detail | | XAV939 (X) | Gö6983 (G) | Y-27632 (Y) | ActA (/A) | PD166866 (F) | PD0325901 (P) | AZ628 (A) | GDC-0994 (G) |
|---|---|---|---|---|---|---|---|---|---|---|
| FXGY/A | XAV/Gö/Y + Activin A+ | PD16 (FGFR1i) | 2 μM | 2 μM | 10 μM | 10 ng/ml | 1 μM | | | |
| AXGY/A | | AZ628 (RAFi) | 2 μM | 2 μM | 10 μM | 10 ng/ml | | | 5 μM | |
| PXGY/A | | PD03 (MEKi) | 2 μM | 2 μM | 10 μM | 10 ng/ml | | 1 μM | | |
| GXGY/A | | GDC (ERKi) | 2 μM | 2 μM | 10 μM | 10 ng/ml | | | | 5 μM |
| PXGGY/A | | GDC + PD03 | 2 μM | 2 μM | 10 μM | 10 ng/ml | | 1 μM | | 2.5 μM |
| AXGGY/A | | AZ628 + GDC | 2 μM | 2 μM | 10 μM | 10 ng/ml | | | 5 μM | 2.5 μM |
| FXGAY/A | | PD16 + AZ628 | 2 μM | 2 μM | 10 μM | 10 ng/ml | 1 μM | | 5 μM | |
| FXGGY/A | | PD16 + GDC | 2 μM | 2 μM | 10 μM | 10 ng/ml | 1 μM | | | 2.5 μM |

TABLE 6

Media compositions 6: Enhanced primed-to-naïve resetting conditions (Related to FIG. 5)

Composition: N2B27+

| Media | PD03 (P) | GDC (G) | XAV (X) | Gö (G) | ROCKi (Y) | Activin A (/A) |
|---|---|---|---|---|---|---|
| PXGGY | 1 μM | 2.5 μM | 2 μM | 2 μM | 10 μM | |
| PXGGY/A | 1 μM | 2.5 μM | 2 μM | 2 μM | 10 μM | 10 ng/ml |

High-throughput chemical screening: For high-throughput screening, WIBR3 OCT4-ΔPE-GFP+naïve hESCs generated with inducible KLF2 and NANOG transgenes were used, as described previously. These cells were maintained in 1 μM PD0325901, 1 μM CHIR99021, and 2 μg/ml DOX (Sigma) (2i/DOX). For compound screening in presence of 2i/Y, 3,000 OCT4-ΔPE-GFP+naïve hESCs were seeded per well in vitronectin-coated 384 well plates in serum-free N2B27 media supplemented with 1 μM PD0325901, 1 μM CHIR99021, and 10 μM Y-27632. The next day individual compounds from the Novartis Mechanism of Action (MoA) library were applied at two concentrations (2.5 μM and 5 μM) in duplicate using an Echo 550 Acoustic Liquid Handler (Labcyte), and compounds were refreshed on day 4. Images were analyzed on day 5 post-DOX withdrawal using a Yokogawa Cell Voyager 7000 High-Content Imaging System in confocal mode using a 10x dry (NA=0.45) objective lens using four fields per well that provided for full well coverage. While the screen was performed at two concentrations (2.5 μM and 5 μM), the lower concentration yielded few additional hits. Hit compounds were validated in 384 well plates across an 8-point concentration range in duplicates. For high-throughput screening in absence of 2i, 384 well plates were pre-coated with mitotically inactivated mouse embryonic fibroblasts (MEFs) to improve viability. Pilot assays revealed that a maximal Z'-factor was obtained in absence of 2i by performing image acquisition on day 7 post-DOX withdrawal and using a seeding density of 800 OCT4-ΔPE-GFP+naïve hESCs per 384 well. Naïve hESCs were seeded in serum-free N2B27 media supplemented with 10 μM Y-27632 alone (N2B27/Y) or upon addition of 2 μM XAV939 (XAV/Y) or 2 μM Gö6983 (Gö/Y). The next day individual compounds from the Novartis MoA library were added at 5 μM concentration using the Echo 550 Acoustic Liquid Handler and compounds were refreshed on days 3 and 6. Images were acquired using the Yokogawa Cell Voyager 7000 on day 7 and analyzed as described above. Hit compounds were validated in 384 well plates across an 8-point concentration range in duplicate.

Defining alternative naïve maintenance media: To define the activity of selected hit compounds during extended naïve culture, naïve hESCs derived from the primed state and maintained in 5i/L/A were dissociated with Accutase (Thermo Fischer Scientific, A1110501) and $1.5 \times 10^5$ single cells were seeded in 5i/L/A media on MEF-coated plates. After 24 hours, 5i/L/A media were switched to experimental maintenance conditions to validate hits from the screen. After 4-6 days the cells were split in a 1:2 or 1:3 ratio and further maintained for 4-6 days before analysis by FACS, qRT-PCR, AP staining, and/or RNA-seq. 5i/L/A media in which the MEK inhibitor PD0325901 was replaced with 5 μM AZ628 are represented as alternative 5i/L/A (a5i/L/A). FXGY, AXGY, AXGYU, PXGY, and GXGY media were prepared in serum-free N2B27 media supplemented with 1 μM PD166866, 5 μM AZ628, 5 μM AZ628 and 1 μM UNC0638, 1 μM PD0325901, and 5 μM GDC-0994, respectively, together with 2 μM XAV939, 2 μM Gö6983, and 10 μM Y-27632. During these assays cells were fed with fresh media every second day and cultured in 5% $O_2$, 5% $CO_2$ at 37° C. Detailed information on conditions used for defining alternative naïve maintenance media can be found in Tables 1-6.

Endothelial-to-hematopoietic transition assay: For primed-to-naïve resetting experiments, primed hESCs were dissociated into single cells using TrypLE Express (GIBCO, 12604), washed in fibroblast medium [DMEM (Millipore Sigma, #SLM-021-B) supplemented with 10% FBS (HyClone, SH30396.03, 1× GlutaMAX (GIBCO, 35050), and 1% penicillin-streptomycin (GIBCO, 15140)] and $2 \times 10^5$ single primed hESCs were seeded on mitomycin C-inactivated mouse embryonic fibroblast (MEF) feeder cells coated 6 well plates in 3-4 mL mTeSR1 supplemented with 10 μM Y-27632. Two days later, medium was switched to either 5i/L/A or experimental induction media and maintained for 10-12 days. Cells at this stage were considered at passage zero. Cells were then split in a 1:2 or 1:3 ratio every 4-6 days as single cells using Accutase (Thermo Fischer Scientific, A1110501). PXGGY media were prepared in serum-free N2B27 media supplemented with 1 μM PD0325901, 2 μM XAV939, 2 μM Gö6938, 2.5 μM GDC-0994, and 10 μM Y-27632. PXGGY/A media were prepared in PXGGY supplemented with 10 ng/ml Activin A. During these assays cells were fed with fresh media every second day and cultured in 5% $O_2$, 5% $CO_2$ at 37° C. Detailed information on the conditions used for defining alternative naïve induction media can be found in Tables 1-6.

Flow cytometry: Primed hESCs were single-cell dissociated using TrypLE Express, while Accutase was used for naïve hESCs. Cells were resuspended in fibroblast medium and centrifuged. Cell pellets were washed in 5 mL ice-cold PBS. The cells were then resuspended in 100 mL fresh ice-cold FACS buffer (PBS supplemented with 5% FBS), and incubated with antibodies for 30 minutes on ice in the dark. The following antibodies were used: anti-SUSD2-PE (1:100), anti-CD75-eFluor 660 (1:100), anti-CD90-PE (1:100), anti-ITGA6-FITC (1:100) and EGFR-APC (1:25). Post-incubation the cells were washed once with 1 mL ice-cold PBS, resuspended in fresh 500 μl FACS buffer, and passed through a 0.35 μm cell strainer into round bottom FACS tubes (Corning, #352235). Flow cytometry was performed using a BD LSRFortessa X-20 and the data were analyzed using the FlowJo software.

Quantitative reverse transcriptase PCR (qRT-PCR): Total RNA was isolated using the E.Z.N.A. total RNA kit I and cDNA synthesis was performed from total RNA using the high-capacity cDNA reverse transcription kit (Applied Biosystems, U.S. Pat. No. 4,368,814). qRT-PCR was performed using PowerUp SYBR Green Master Mix (Applied Biosystems, A25743) on the StepOnePlus Real-Time PCR System (Applied Biosystems). Gene expression was normalized to RPLPO and analyzed using the ΔCt method. Error bars represent the standard deviation (SD) of the mean of technical replicates.

Alkaline phosphatase (AP) staining: AP staining was performed following the manufacturer's instructions using the Leukocyte Alkaline Phosphatase Kit (Sigma, 86R, 1KT). For AP staining cells were seeded at equal density in 6-well plates and passaged in the same ratio for all conditions. Post-staining cells were allowed to dry overnight in the dark and scanned using HP Color Laser Jet Managed printer/scanner (MFP E67650).

Imaging: The imaging of H9 and WIBR3 hESCs was performed in live conditions within culture media. For WIBR3 MECP2-GFP/tdTomato hESCs the medium was aspirated, cell were washed twice with PBS, and imaged in 1 mL of PBS. All images were captured at 10× magnification on a Leica DMi8 microscope.

Karyotyping For G-banded karyotyping naïve hESCs were cultured in 6-well plates in 5i/L/A or alternative maintenance media (FXGY, AXGY, PXGY and GXGY) or primed-to-naïve resetting medium (PXGGY) for the indicated passage numbers. Cells were then seeded in T25 flasks and karyotyped by the Cytogenetics and Molecular Pathology facility of Washington University in St. Louis using standard methods.

Immunoblotting: For western blot analysis of protein expression in primed hESCs, a semi-confluent well was treated with 4 mL of mTeSR1+ROCKi, 5i/L/A, or alternative naïve maintenance and induction media for 20 hours. Post-treatment, the cells were washed with 1 mL of cold PBS twice and solubilized in 300 μL of RIPA buffer (Cell Signaling, #9806) with phosphatase inhibitor (ThermoFischer Scientific, #A32957) on ice for ~20 min. For naïve hESCs, a single cell dissociation was prepared using Accutase and single cells were transferred to Gelatin-coated plates for 45 minutes at 37° C. This is a feeder-depletion step, which allows the MEFs to attach to the plate surface, while hESCs remain in the media. The media were then collected in 15 mL tubes and centrifuged. Cell pellets were washed twice with 2 mL cold PBS and solubilized in 300 μL RIPA buffer on ice for least 20 min. The lysates from both primed and naïve cells were collected after centrifugation. Protein concentration was measured by the Bradford assay (Biorad, #5000006). 20 μg of protein samples were loaded on an SDS-PAGE gel and transferred to a nitrocellulose membrane for immunoblotting. Afterward, the membrane was blocked with 5% nonfat milk (Bio-Rad, #170-6404) at room temperature for 1 hour in TBST (20 mM tris-HCl, pH 7.6, 137 mM NaCl, and 0.1% Tween 20), and incubated with a primary antibody [β-actin (1:2000), ERK1/2 (1:3000), p-ERK1/2 (1:1500), MEK1/2 (1:2500) and p-MEK1/2 (1:1500)] overnight at 4° C., followed by a secondary antibody (1:2000) conjugated with horseradish peroxidase for 45 min at RT. Protein bands on the membrane were detected by the ECL detection system (Biorad #1705060). Immunoblots were imaged and analyzed using the Invitrogen iBright Imaging CL1000 System.

RNA sequencing: Total RNA was isolated from 2 million naïve or primed cells using the E.Z.N.A. total RNA kit I. Library construction was performed using the SMARTer Directional cDNA Library Construction Kit (Clontech, 634933). Libraries were sequenced on an Illumina Hi-Seq3000 1X50 or NovaSeq S4 2×150 platform at the Genome Technology Access Center at Washington University School of Medicine in St. Louis.

Whole genome bisulfite sequencing Genomic: DNA was extracted from 2 million naïve or primed cells using the DNeasy Blood and Tissue Kit (QIAGEN, Valencia, CA). Whole Genome Bisulfite conversions were performed with 200 ng of gDNA using the EZ DNA Methylation-Gold, 50 rxn kit (Fisher, #50444294). WGBS Libraries were created using the Accel-NGS Methyl-Seq DNA Library Kit-24 rxns (Swift Biosciences, #30024) and Accel-NGS Methyl-Seq Dual Indexing Kit-96 rxns (Swift Biosciences, #38096). The libraries were pooled and sequenced on 0.240 of a NovaSeq S4 flow cell (300 XP; targeting 30× WGBS coverage/120 Gb per sample) at the Genome Technology Access Center at Washington University School of Medicine in St. Louis.

Re-priming of naïve hESCs: For re-priming, a 70%-80% confluent culture of naïve hESCs that were maintained in 5i/L/A or alternative conditions were harvested as single cells using Accutase and seeded in a 1:2 ratio on a Matrigel-coated plate in mTeSR1 media supplemented with ROCK inhibitor Y-27632 and cultured in 5% $CO_2$ and 20% $O_2$ at 37° C. Y-27632 was withdrawn on the second day. Colonies with a flat morphology resembling primed hESCs appeared within 6 days. These colonies were dissociated with TrypLE as single cells and analyzed by FACS for the primed-specific cell surface marker CD90.

Capacitation of naïve hESCs: Capacitation of naïve hESCs was performed as previously described (Rostovskaya et al., 2019). Approximately 0.5×106 TrypLE-dissociated naïve hESCs were seeded in 5i/L/A or alternative naïve conditions on one well of a Geltrex (Thermo Fisher, A1413201) coated 6-well plate. After 48 hours, naïve media were switched to capacitation media (N2B27 supplemented with 2 μM XAV939). The cells were fed fresh media every 1-2 days and passaged at 70%-80% confluency (about 4-5 days) using TrypLE (GIBCO, 12604054). 10 μM of Y-27632 was added for 24 hr following passaging. Cells were analyzed for the expression of naïve and primed-specific genes by qRT-PCR after 10 days. Capacitation was performed in 5% $CO_2$ and 5% $O_2$ at 37° C.

Derivation of hTSCs from naïve hESCs: hTSCs were derived from naïve hESCs as previously described. Briefly, naïve hESCs maintained in 5i/L/A or alternative naïve media were dissociated into single cells using TrypLE. 0.5-1.0×10$^6$ cells were seeded in a 6-well plate pre-coated with 5 μg/mL Collagen IV and switched to 2 mL hTSC medium (Okae et al., 2018) [DMEM/F12 supplemented with 0.1 mM 2-mercaptoethanol, 0.2% FBS, 0.5% Penicillin-Streptomycin, 0.3% BSA, 1% ITS-X (GIBCO, 51500), 1.5 μg/ml L-ascorbic acid (Wako, 013-12061), 50 ng/ml EGF (Rockland, 009-001 C26), 2 μM CHIR99021 (Stemgent, 04-0004), 0.5 μM A83-01 (BioVision, 1725), 1 μM SB431542 (BioVision, 1674), 0.8 mM VPA (Tocris, 2815), and 5 μM Y-27632]. Cells were cultured in 5% $CO_2$ and 20% $O_2$ at 37° C., media were changed every 2 days, and passaged upon reaching 80%-100% confluency at a ratio of 1:2 to 1:4 using TrypLE. Cells were analyzed by FACS for the hTSC-specific cell surface markers ITGA6 and EGFR after 5-7 passages.

Results

Figure 1A:
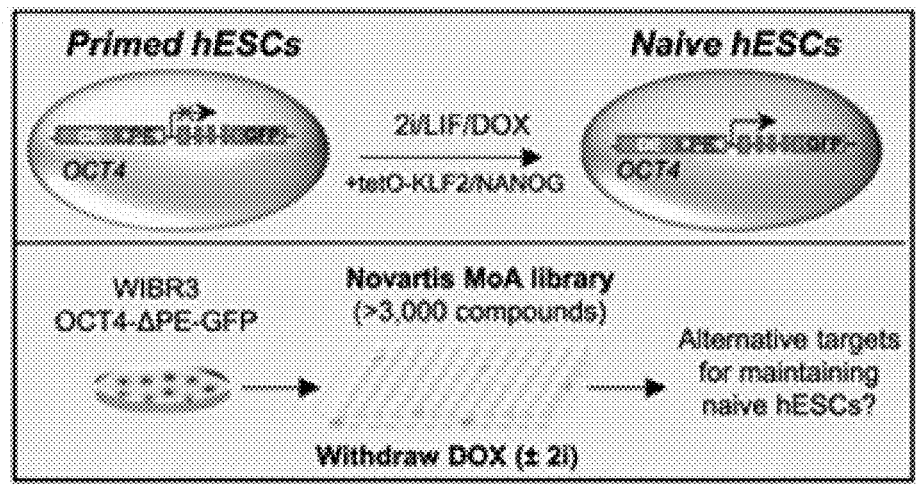

High-throughput screening identifies modulators of naïve human pluripotency in minimal conditions: Previous work, which resulted in the identification of the 5i/L/A cocktail, screened a library of 230 kinase inhibitors to identify compounds that can sustain naïve-specific reporter activity in combination with 2i/LIF. The present example considered whether alternative modulators of naïve human pluripotency may be identified by repeating this screen on a high-throughput scale and applying a dynamic chemogenetic library of ~3,000 chemical probes in which a well-defined target is known for each of the compounds (Novartis Mechanism of Action Box) either in the presence or absence of 2i. Naïve hESCs that were generated with doxycycline (Dox)-inducible transgenes driving exogenous KLF2 and NANOG transgenes were used. These cells contain an endogenous OCT4 reporter allele in which the primed-specific proximal enhancer has been deleted (OCT4-ΔPE-GFP). Upon withdrawal of DOX, GFP reporter activity was reduced and colony morphology was lost within 5 days, providing a convenient time window for high-throughput screening (FIG. 1A).

Figure 1B:
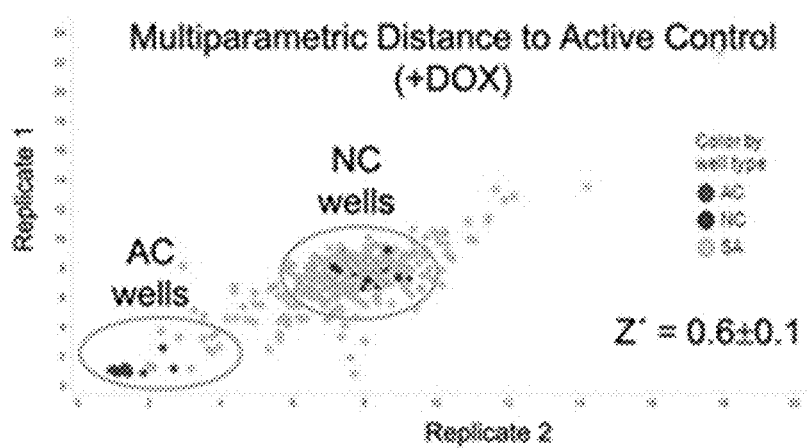

As a pilot experiment, 3,000 OCT4-ΔPE-GFP+-naïve hESCs were seeded per well in 384-well plates and removed DOX but continued to culture the cells in the presence of 2i and the Rho-associated kinase (ROCK) inhibitor Y-27632, which promotes viability after single cell dissociation (2i/Y). LIF was omitted since its removal from established naïve hESCs had little impact on naïve-specific enhancer activity and gene expression. Individual compounds were applied on days 1 and 4, and images were obtained on day 5. A multi-parametric data analysis (MPDA) algorithm was designed to analyze these images, computing a Mahalanobis distance score between each compound and the active (+DOX) and negative (−DOX) control wells based on features that included area, compactness, and fluorescence intensity of individual object regions (FIG. 1B). This enabled the ability to distinguish objects that were likely due to cell death and phenotypes that were disparate from the desired phenotype observed in the positive control wells. The screen showed good performance (Z'=0.6±0.1), and hits were called based on distance to the active control (+DOX) wells. This screen identified 33 validated hit compounds that could synergize with the 2i cocktail in maintaining naïve colony morphology and reporter activity upon removal of DOX-inducible transgenes. These hits included several target classes that have previously been implicated in control of naïve human pluripotency, such as PKC, BRAF, FGFR, VEGFR, and p38 MAPK, demonstrating the capability of the screen to identify chemical modulators of naïve human pluripotency.

It was investigated whether the screening platform could be adapted to discover alternative compounds that sustain naïve human pluripotency in the absence of 2i. OCT4-ΔPE-GFP+-naïve hESCs were again seeded in 384-well plates, but this time compounds were supplemented only with Y-27632 (N2B27/Y). Pilot assays revealed that a maximal Z' factor was obtained in absence of 2i by performing image acquisition on day 7 post-DOX withdrawal.

As expected, MEK1 inhibitors emerged as the top-ranked category during validation assays (28%). In addition, a robust increase in GFP activity was confirmed in presence of several tankyrase (TNKS) inhibitors, as well as inhibitors of ERK, DNMT1, FGFR1, and SRC (FIG. 1C and FIG. 1D, left panel). The TNKS inhibitor XAV939, which showed a particularly strong effect, inhibits WNT signaling and was shown to be beneficial for naïve human pluripotency in two studies prior to this screen. Compared to inhibition of MEK1, treatment with XAV939 yielded larger colonies but a slightly dimmer OCT4-ΔPE-GFP signal (FIG. 1D, left panel).

The Mechanism of Action library was then re-screened to identify compounds that could synergize with both XAV939 and Y-27632 (XAV/Y). MEK1 again appeared as the top target class, but other hit compounds were also identified and validated that could synergize with TNKS inhibition, including inhibitors of EGFR, PKC, RAF, and SRC (FIG. 1C and FIG. 1D, middle panel). PKC was an enriched target class in both our 2i/Y and XAV/Y screens (FIG. 1C), which is consistent with inclusion of the PKC inhibitor Gö6983 in the t2i/L/Gö formulation. The Mechanism of Action library was therefore also re-screened in the presence of the PKC inhibitor Gö6983 and Y-27632 (Gö/Y). This screen identified synergy between Gö6983 and inhibitors of RAF, TGFBR2, SRC, and other targets (FIG. 1C and FIG. 1D, right panel). Excluding MEK1/2 inhibitors, our high-throughput screens identified 35 hit compounds that showed activity in maintaining naïve human pluripotency in one or several of the three examined basal conditions (Y, Gö/Y and XAV/Y). These compounds included inhibitors of signal transduction cascades, G-protein-coupled receptors, chromatin modifiers, cell-cycle regulators, and other targets. In cases where multiple hit compounds converged on the same molecular target (RAF, SRC, TGFBR, and TNKS), the compound with greater activity was selected for follow-up experiments.

Defining the activity of selected hit compounds during extended naïve hPSC culture: 13 hit compounds were investigated that could be readily procured from commercial vendors (FIG. 1E) were capable of maintaining naïve human pluripotency over multiple passages in the absence of 2i. For this purpose, WIBR3 OCT4-ΔPE-GFP+-naïve hESCs that were generated in the absence of reprogramming transgenes were used using the 5i/L/A cocktail. Naïve hESCs were seeded in 6-well plates and transferred from 5i/L/A to the 17 different 2i-independent media formulations identified in our high-throughput screens (3/13 hits showed activity in multiple screens and were therefore tested in multiple basal media) (FIG. 1E). Compounds were tested at two different concentrations (2.5 and 5 µM), and cells were maintained for two passages (FIG. 2A). Imaging and quantitative reverse transcriptase PCR (qRT-PCR) analysis indicated that only 3 of these compounds showed significant activity in maintaining OCT4-ΔPE-GFP reporter activity after passaging: the ERK1/2 inhibitor GDC-0994 and the FGFR1 inhibitor PD166866 showed activity in the presence of ROCK inhibitor (Y) alone, while the pan-RAF inhibitor AZ628 showed activity in Gö/Y and XAV/Y (FIG. 2B).

Figure 2C:
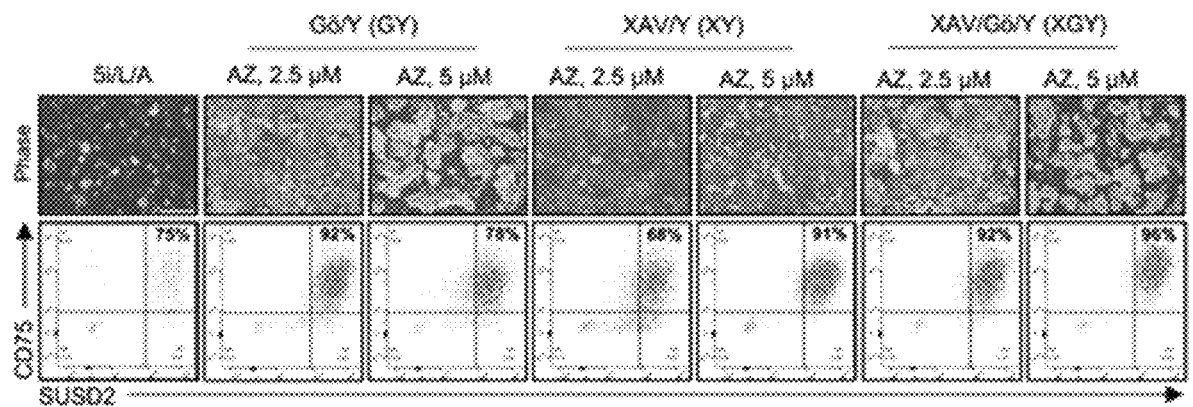
Figure 2D:
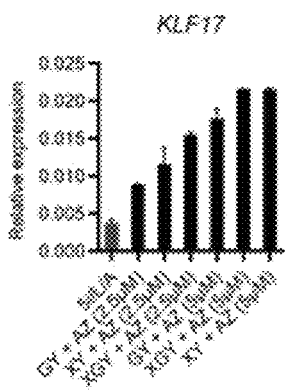

The pan-RAF inhibitor AZ628 was initially focused on, which supported robust expansion of OCT4-ΔPE-GFP+cells in the presence of either XAV or Gö. Next, it was asked whether naïve hESC self-renewal could be enhanced by combining AZ628, XAV, Gö, and Y-27632 together in a single cocktail (AXGY). Indeed, this combination enabled homogeneous expansion of naïve hESCs as measured by flow-cytometry analysis for the cell-surface markers CD75 and SUSD2, which are enriched in naïve compared to primed hESCs, and qRT-PCR analysis for the naïve-specific transcription factor KLF17, which is expressed in the human blastocyst (FIG. 2C and FIG. 2D). Next, it was investigated whether the addition of the other hit compounds to the AXGY cocktail could further boost the expansion, purity, and/or gene expression of naïve hESCs. Notably, the SRC family kinase inhibitor Naphtol-PP1, which scored in all three of our high-throughput screens, enhanced dome-shaped colony morphology. A similar effect was seen with the SRC inhibitor WH-4-023, which is included in the 5i/L/A cocktail. However, SRC inhibition had little impact on expression of naïve-specific cell-surface markers or transcript levels and was therefore not included for further analysis. The G9a/GLP inhibitor UNC0638 further stimulated KLF17 expression, although colony proliferation was slightly reduced compared to AXGY.

Figure 2E:
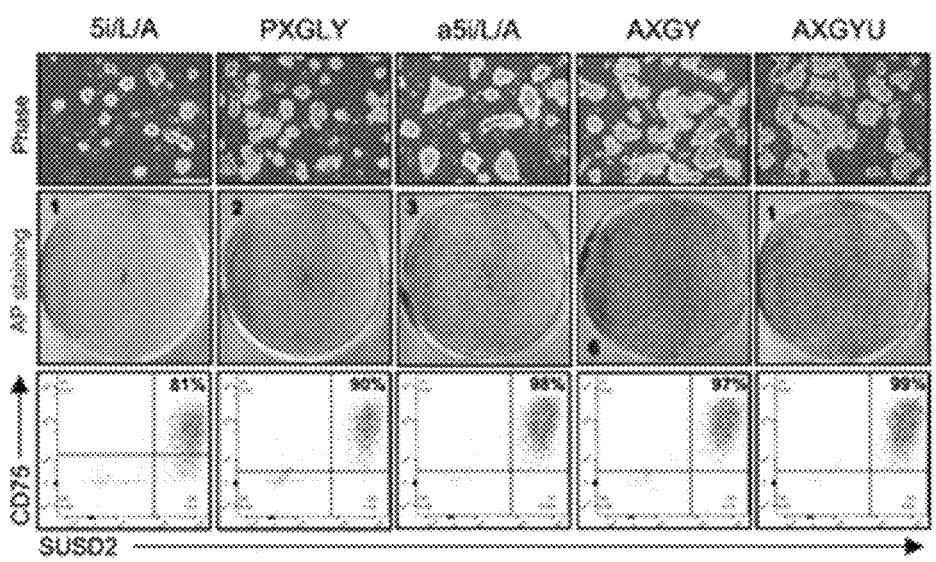
Figure 2F:
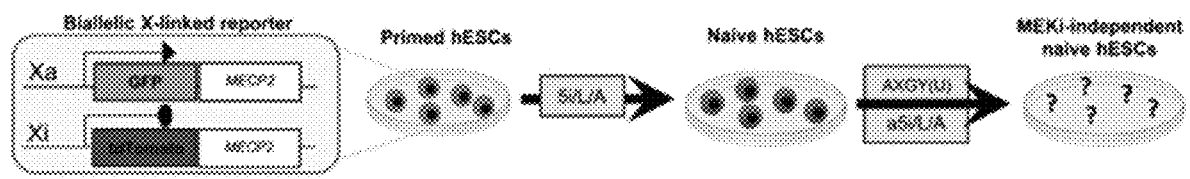
Figure 2G:
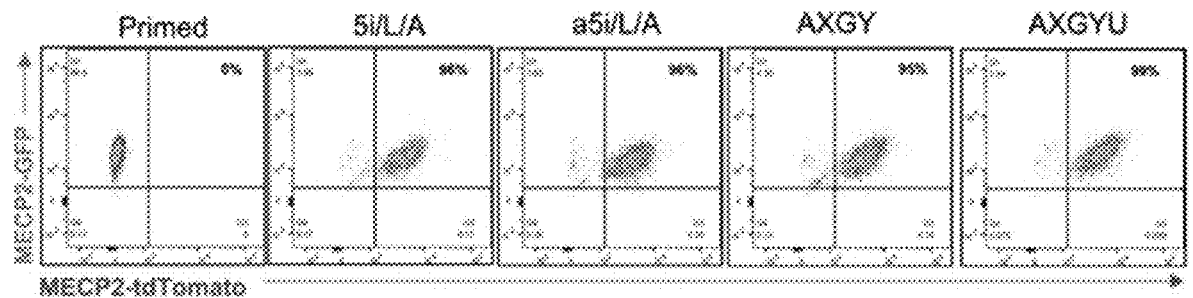

It was also tested whether AZ628 could substitute for the MEK inhibitor PD03 in the 5i/L/A cocktail. This culture formulation, which we designated as alternative 5i/L/A (a5i/L/A), maintained a high level of OCT4-ΔPE-GFP activity and enhanced the purity of CD75/SUSD2 double-positive cells compared to 5i/L/A in both wild-type H9 and WIBR3 cells (FIG. 2E). However, naïve hESCs maintained in AXGY displayed markedly enhanced colony formation efficiency compared to 5i/L/A or a5i/L/A (FIG. 2E). This suggests that the combination of TNKS and PKC inhibitors provides a signaling milieu that is more conducive for naïve cell expansion. Colony formation efficiency in AXGY was more comparable to PXGLY, which is a modified version of the t2i/L/Gö cocktail in which GSK3 inhibition is replaced by TNKS inhibition (FIG. 2E). Whether these alternative naïve conditions can maintain biallelic expression of a dual X-linked fluorescent reporter line was also examined, which is activated upon primed-to-naïve resetting in 5i/L/A (FIG. 2F). Indeed, a5i/L/A, AXGY, and AXGY supplemented with the G9a/GLP inhibitor UNC0638 (AXGYU) were all capable of maintaining MECP2-GFP/tdTomato double-positive cells over two passages, suggesting that both X chromosomes remain active under these alternative naïve conditions (FIG. 2G).

Figure 2H:
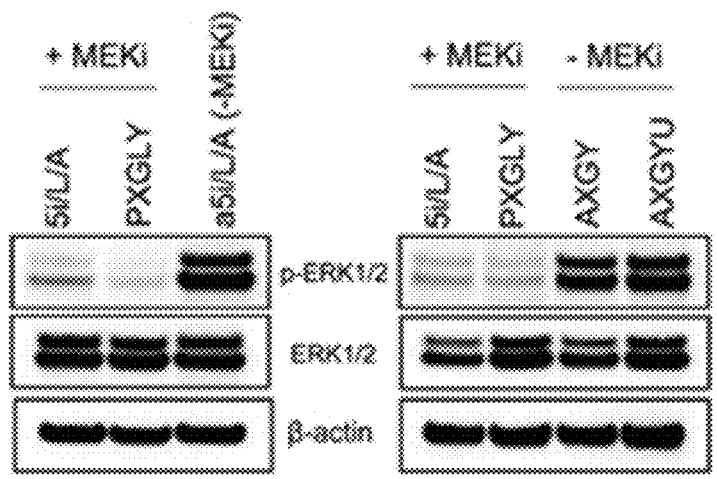

AZ628 is a pan-RAF inhibitor for BRAF and CRAF (RAF1). Since the RAF kinases are located upstream of MEK1/2 in the MAPK signaling cascade, it was expected that RAF inhibition should phenocopy MEK inhibition and suppress the downstream phosphorylation of ERK1/2. Surprisingly, switching naïve hESCs from 5i/L/A to the alternative naïve maintenance media resulted in stimulation of phosphorylated (p)-ERK levels (FIG. 2H). This result indicates that the complete suppression of ERK phosphorylation is dispensable for maintenance of several hallmarks of naïve human pluripotency, such as robust expression of KLF17, OCT4-ΔPE-GFP reporter activity, and biallelic MECP2 expression. It also suggests that the pan-RAF inhibitor AZ628 may stimulate naïve human pluripotency through mechanisms that are located upstream of ERK, such as blockade of other RAF or MEK targets. Alternatively, the effect of AZ628 could be mediated through inhibition of lower affinity kinase targets, which include Epha2, PDGFRA, p38 alpha, LCK, and RET.

Figure 3A:
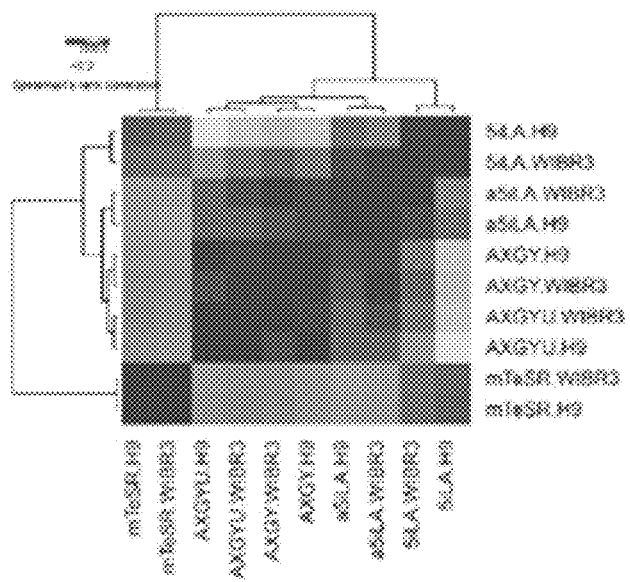
FIG. 3A-3H show molecular profiling of alternative naïve hESCs maintained in the absence of 2i.
Figure 3B:
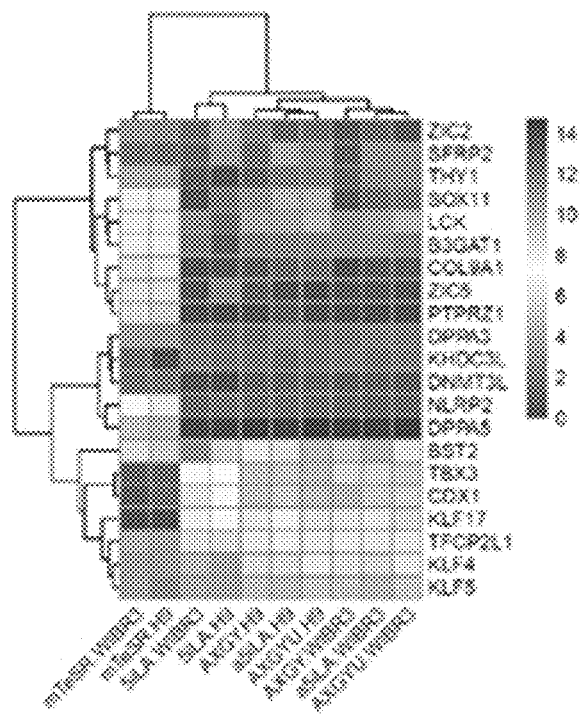
Figure 3C:
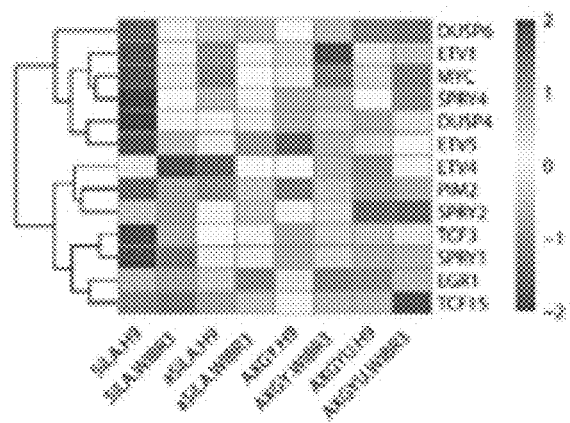

Naïve hESCs maintained with a pan-RAF inhibitor retain a pre-implantation identity: To define the transcriptional identity of naïve hESCs maintained with AZ628, RNA-seq analysis was performed on H9 and WIBR3-naïve hESCs that were derived in 5i/L/A and subsequently transferred to a5i/L/A, AXGY, or AXGYU. Hierarchical clustering based on significantly differentially expressed genes (DEGs) perfectly separated naïve and primed hESCs (FIG. 3A). Within the naïve branch, the alternative naïve media formed a separate cluster from the 5i/L/A samples. Overall, all naïve conditions exhibited highly similar expression of typical naïve-specific transcription factors, such as DPPA3, DPPA5, DNMT3L, NLRP2, and KHDC3L (FIG. 3B). Volcano-plot analyses indicated consistent upregulation of the ERK-responsive negative feedback regulator SPRY1 and the transcription factor GLI2 in the alternative naïve conditions, while the 5-methylcytosine hydroxylase TET2 and markers associated with extraembryonic lineages (e.g., GATA6, GCM15, HAND1, KRT18, TFAP2A) were upregulated in 5i/L/A. The alternative naïve hESCs that were maintained without MEK1/2 inhibitors also showed upregulation of the ERK-responsive genes ERG1, SPRY2, and TCF3 (FIG. 3C).

Figure 3D:
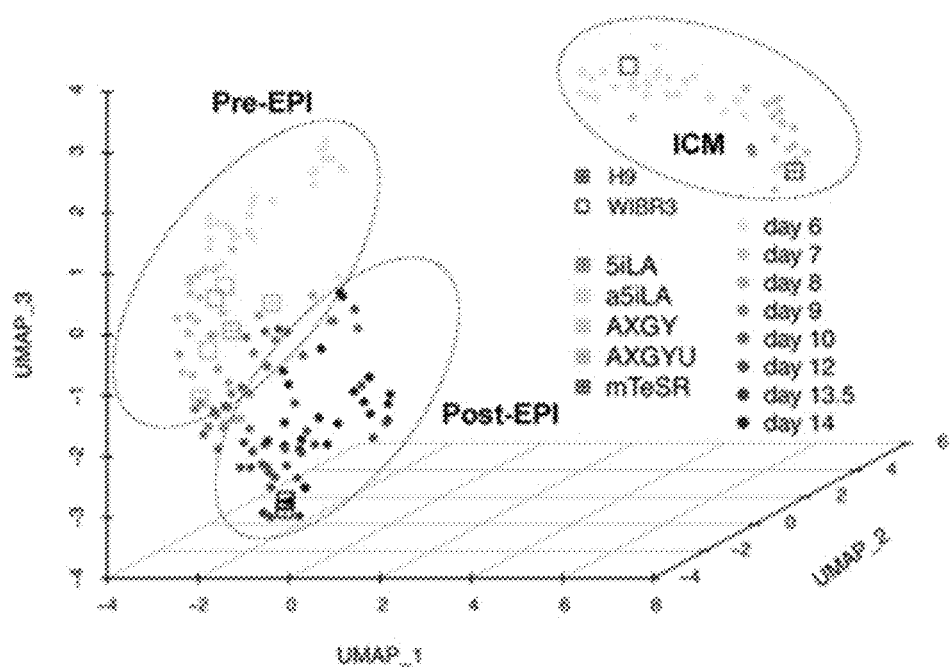

Comparison to scRNA-seq analysis of 3D-cultured human embryos segregated 5i/L/A and the alternative naïve conditions into two distinct clusters: while 5i/L/A samples were more closely aligned with the inner cell mass (ICM) at days 6-7 of human development, naïve hESCs maintained in AXGY, AXGYU, or a5i/L/A clustered more closely with pre-implantation epiblast (EPI) cells at days 7-8 of development (FIG. 3D). In contrast, primed hESCs in mTeSR media aligned more closely with post-implantation EPI cells at days 12-14 of development, which is consistent with a prior comparison to non-human primate embryos. These data indicate that naïve hESCs maintained with the pan-RAF inhibitor AZ628 reside in a more advanced stage of human EPI development yet retain expression of typical marker genes associated with naïve human pluripotency.

Figure 3E:
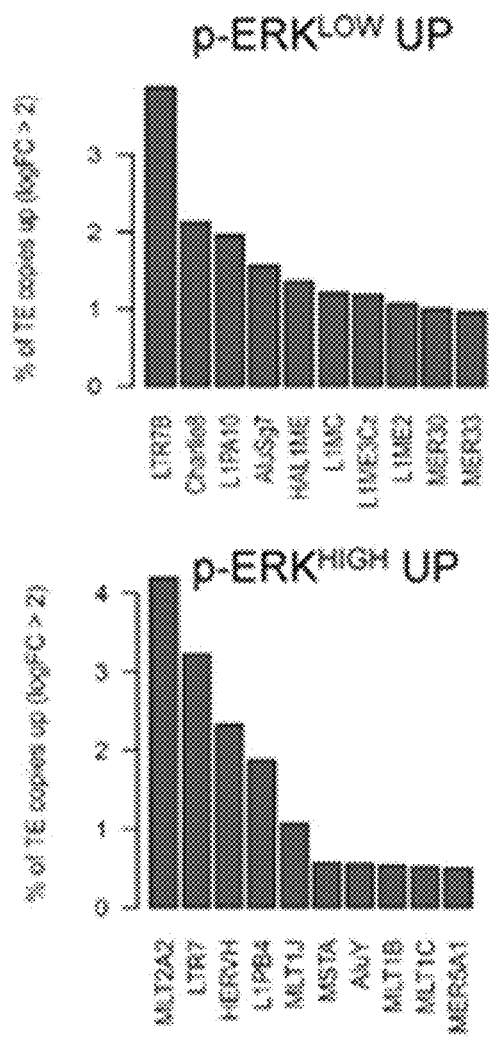
Figure 3F:
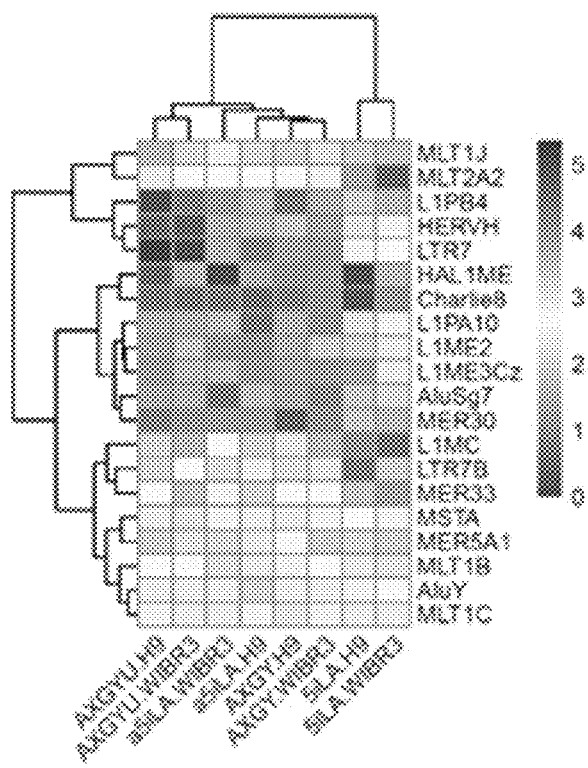
Figure 3G:
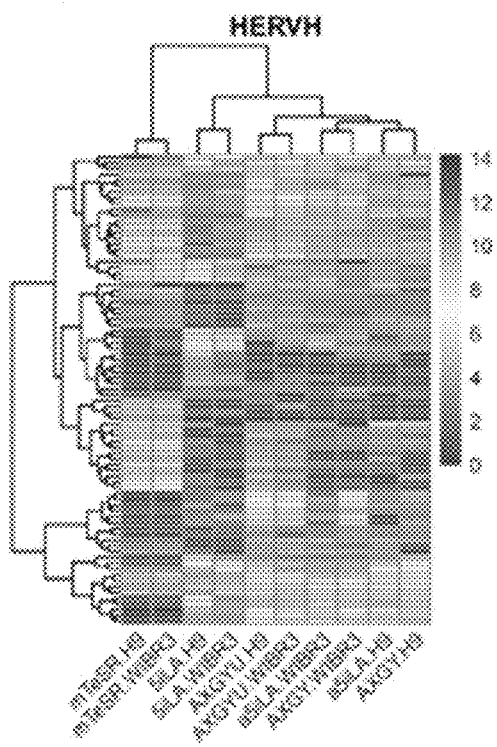

Since naïve and primed hESCs can be distinguished by expression of developmentally programmed TE families, the transposon transcription profile or "transposcriptome" was also examined under alternative naïve conditions. Naïve cells in 5i/L/A showed elevated expression of the LTR7B TE subfamily, while transfer to AXGY, AXGYU, or a5i/L/A resulted in a moderate increase in expression of LTR7 and HERVH integrants (FIG. 3E-3G), which were previously shown to be upregulated in primed hESCs. This effect was most pronounced upon addition of the G9a/GLP inhibitor UNC0638. However, the activation of LTR7 and HERVH elements was far more extensive and significant in primed hESCs, which indicates that LTR7/HERVH expression is dynamic across different stages of EPI development captured in vitro. In contrast, expression of naïve-enriched SVA-D and HERVK integrants was largely invariable between 5i/L/A and the alternative naïve conditions. These data provide a further confirmation that full suppression of ERK phosphorylation is dispensable for maintaining key hallmarks of naïve human pluripotency.

Figure 3H:
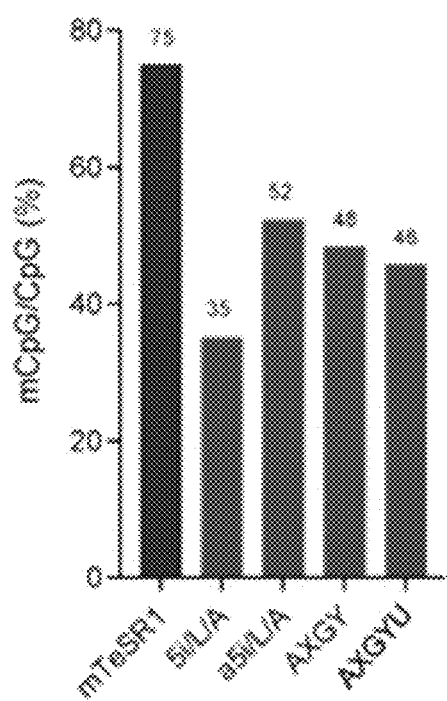

Globally reduced DNA methylation levels are an intrinsic feature of mammalian pre-implantation development that is recapitulated in naïve stem cell culture. Studies in the mouse system have suggested that MEK1/2 inhibition induces global hypomethylation via impairment of DNA methylation enzymes. DNA methylation levels were examined under alternative naïve conditions by whole-genome bisulfite sequencing (WGBS). Overall CpG DNA methylation levels increased from ~35% in 5i/L/A naïve hESCs to ~45% in AXGY(U) and >50% in a5i/L/A. These DNA methylation levels are slightly elevated compared to the level of DNA methylation reported in the human ICM (~42%) but remain significantly lower compared to the hypermethylated DNA signature in primed hESCs (~75%) (FIG. 3H). Despite the overall increase in DNA methylation, increased expression of HERVH integrants in alternative naïve conditions was correlated with locally reduced methylation levels. In addition, DNA methylation at imprinted DMRs was depleted under all examined conditions. This may be explained by the fact that these maintenance experiments were performed in naïve hESCs that were derived from the primed state in 5i/L/A, which is known to cause imprint erasure within four passages.

Figure 4A:
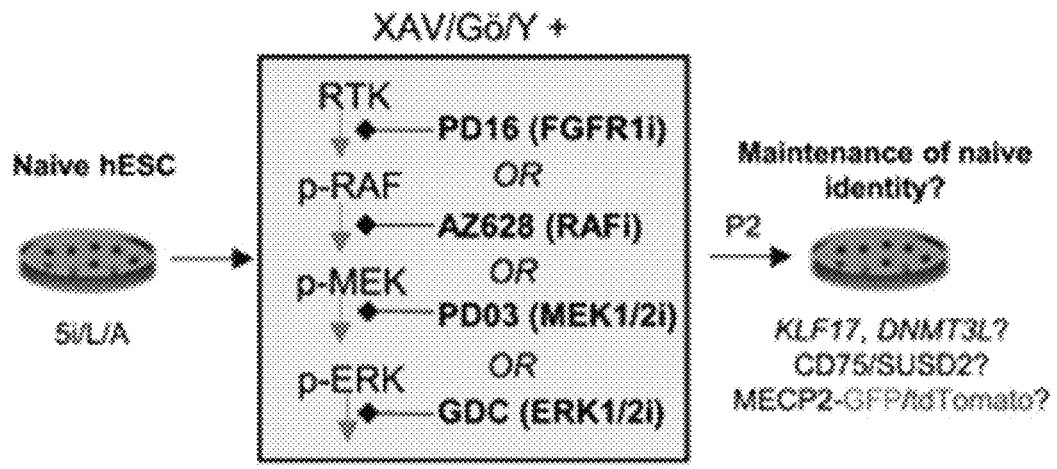
Figure 4B:
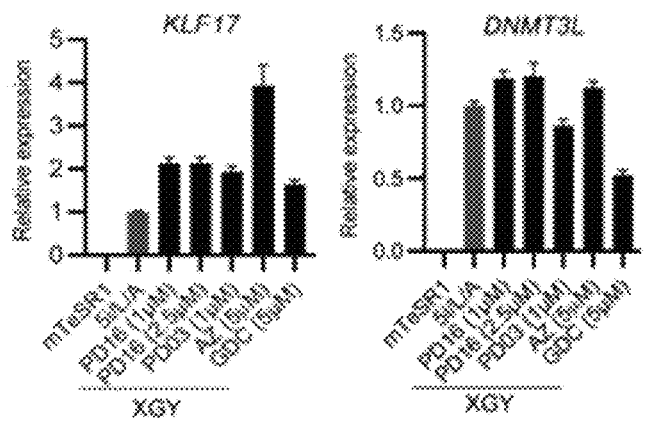
Figure 4C:
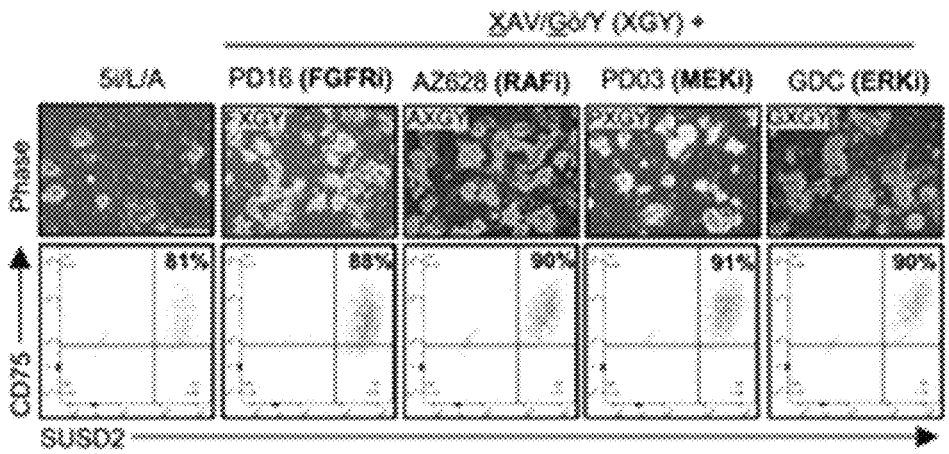
Figure 4D:
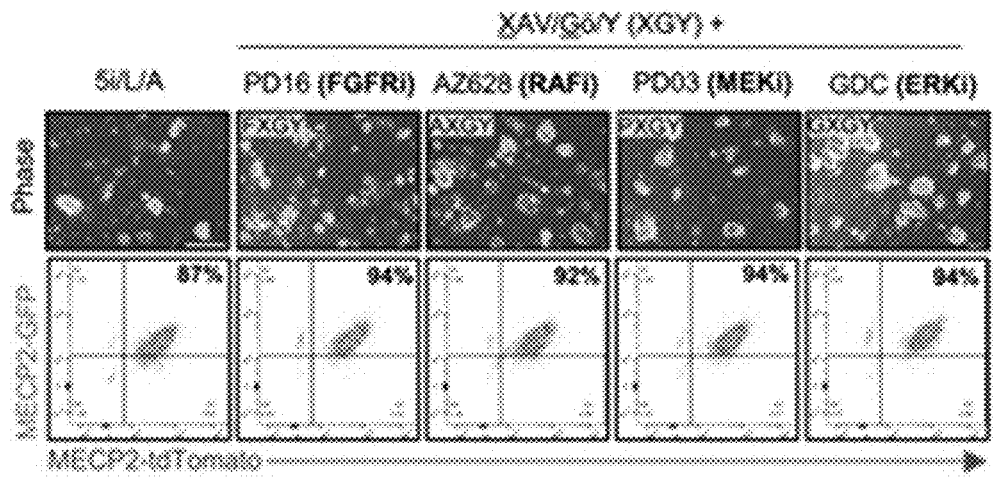

Inhibition of other enzymes in the FGFR-RAF-MEK-ERK pathway also sustains naïve human pluripotency: The above results indicate that the pan-RAF inhibitor AZ628 can maintain key molecular features of naïve human pluripotency in combination with TNKS, PKC, and ROCK inhibitors (XGY). Since AXGY promoted more robust expansion of naïve cells compared to 5i/L/A, it was asked whether any of the other hit compounds from our high-throughput screens could also sustain naïve human pluripotency under these conditions. Naïve hESCs were derived from the primed state in 5i/L/A and switched to serum-free media supplemented with XGY and the commercially available hit compounds. 9 additional compounds were also included that have a shared target annotation as the remaining hit compounds from our screens for which commercial vendors were unavailable. In addition to AZ628, the only compounds that robustly sustained CD75/SUSD2-positive cells over multiple passages were the FGFR inhibitor PD166866 and the ERK inhibitor GDC-0994. While the MAPK14 (p38) inhibitor Semapimod supported some double-positive cells, these cells displayed very limited proliferation. Thus, the only hit compounds that could efficiently replace MEK1/2 inhibitors during the long-term maintenance of naïve human pluripotency inhibit either upstream (FGFR, RAF) or downstream (ERK1/2) kinases (FIG. 4A). Titration experiments revealed that 1 µM of FGFR inhibitor was sufficient to maintain expression of naïve-specific transcripts, while the ERK inhibitor was more effective at 5 µM (FIG. 4B). Flow cytometry confirmed that these inhibitors not only maintained homogeneous CD75/SUSD2 expression but also biallelic X-linked MECP2 fluorescent reporter activity (FIG. 4C and FIG. 4D).

Figure 4E:
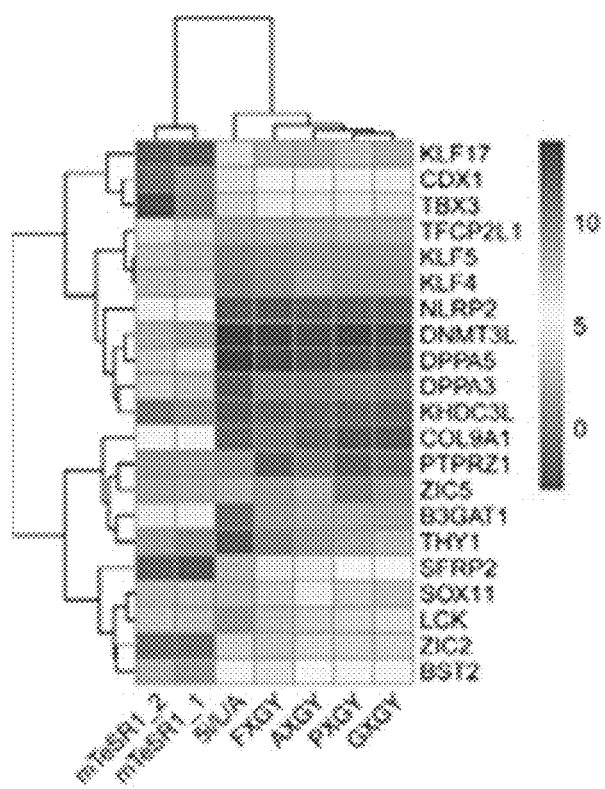
Figure 4F:
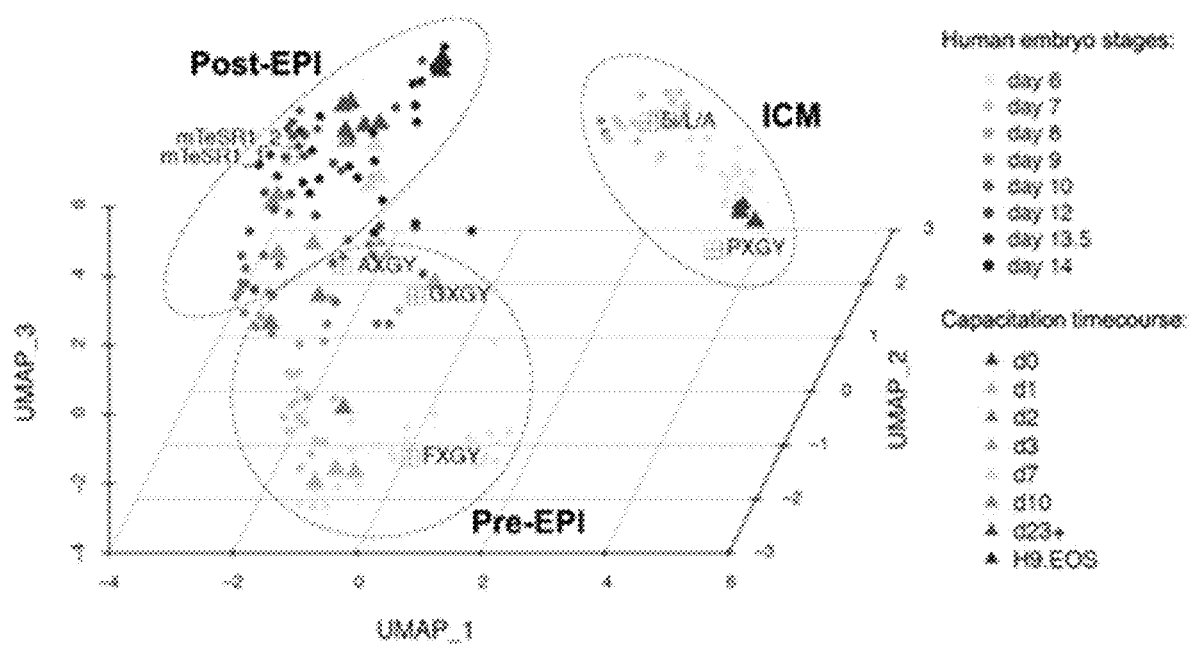
Figure 4G:
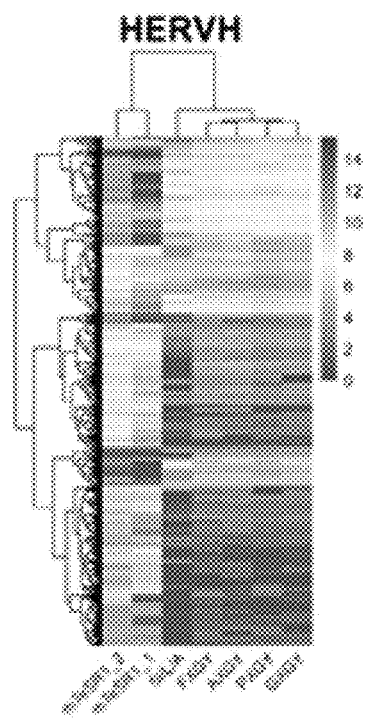

It was then sought to determine whether naïve hPSCs maintained with the FGFR inhibitor PD166866 (FXGY) or ERK inhibitor GDC-0994 (GXGY) reside in a similar state as those maintained in AXGY. Retention of canonical naïve markers in the alternative naïve maintenance conditions was corroborated by RNA-seq analysis, which also showed negligible expression of primed markers (FIG. 4E and FIG. 4F). Transfer from 5i/L/A to AXGY, FXGY, or GXGY captured the cells in a pre-implantation EPI identity, while continuous treatment with a MEK inhibitor (PXGY) drove them toward an ICM identity (FIG. 4F). Similar results were obtained by comparison to cynomolgus macaque embryo stages, although the GXGY condition clustered more closely with macaque ICM. AXGY, GXGY, and FXGY displayed a modest increase in HERVH integrants, while all naïve maintenance conditions showed strong activation of SVA-D integrants (FIG. 4G and FIG. 4H). Global DNA methylation was slightly elevated in all four XGY-based naïve media compared to 5i/L/A but remained substantially reduced compared to the primed state (FIG. 4I). Furthermore, western blotting revealed increased p-ERK levels in AXGY, GXGY, and FXGY relative to PXGY (FIG. 4J). Notably, GDC-0994 is known not to alter the phosphorylation of cellular ERK1/2. Thus, inhibition of FGFR, RAF, MEK, or ERK can sustain bona fide features of naïve human pluripotency despite variable levels of ERK phosphorylation. However, the only conditions that were capable of maintaining naïve hESCs in a human ICM-like state were those that included a direct MEK inhibitor (5i/L/A and PXGY).

While naïve hPSCs are not directly responsive to embryonic lineage inductive cues, they can be re-adapted to primed culture conditions (a process called "re-priming") or transitioned into a lineage-competent formative state upon treatment with the TNKS inhibitor XAV939. Naïve hESCs derived in 5i/L/A and switched to three alternative maintenance media (AXGY, GXGY, or FXGY) acquired a primed morphology and activated the primed-specific cell-surface marker CD90 upon treatment with mTeSR1 media within two passages. Furthermore, they downregulated naïve-specific transcripts and activated formative markers during a 10-day capacitation experiment. Consistent with their more advanced identity relative to human EPI development and a previously published capacitation time course (FIG. 4F), naïve hESCs maintained in AXGY showed more robust induction of formative markers compared to 5i/L/A. Hence, naïve hESCs maintained in the absence of a direct MEK inhibitor remain competent to re-enter the primed pluripotent state.

Since long-term culture in 5i/L/A has been associated with genomic instability, karyotyping was performed on naïve cells that were derived in 5i/L/A and switched to alternative naïve maintenance conditions. Naïve hESCs that were continuously maintained in 5i/L/A contained various chromosomal rearrangements by passage 10. In contrast, a normal karyotype was maintained in naïve hESCs that were switched from 5i/L/A to AXGY or FXGY while a small subset of abnormal cells was observed in either PXGY or GXGY. Hence, transfer to XGY-based naïve maintenance media may enhance the genomic stability of naïve hESCs, although subclonal aneuplodies were still observed in some of the alternative maintenance conditions. We also verified that these cells maintained homogeneous expression of CD75 and SUSD2, indicating that naïve hESCs can be maintained in the absence of a direct MEK inhibitor during extended culture.

Dual MEK and ERK inhibition promotes efficient primed-to-naïve resetting in combination with activin A: Finally, it was examined whether the alternative naïve maintenance formulations identified by our screens are also capable of inducing naïve pluripotency in primed hESCs (FIG. 5A). H9 primed hESCs were seeded on MEFs and treated with 5i/L/A or alternative media and the expression of naïve-specific cell-surface markers was examined by flow cytometry. Remarkably, CD75/SUSD2 double-positive cells were observed only upon treatment with 5i/L/A (FIG. 5B). This suggests that the use of a MEK inhibitor in the 5i/L/A cocktail is critical for inducing naïve pluripotency, but neither MEK nor ERK inhibition is sufficient to induce CD75/SUSD2 double-positive cells in combination with TNKS, PKC, and ROCK inhibitors (XGY). This led to investigate whether the use of multiple FGF pathway inhibitors might facilitate primed-to-naïve resetting together with XGY. While some CD75/SUSD2 double-positive cells were observed upon dual inhibition of RAF and either MEK or ERK, these conditions were cytotoxic (data not shown). In contrast, more robust induction of double-positive cells was observed upon dual inhibition of MEK and ERK (FIG. 5C). This is referred to as naïve induction cocktail as PXGGY for PD0325901 (MEKi), XAV939 (TNKSi), Gö6983 (PKCi), GDC-0994 (ERKi), and Y-27632 (ROCKi).

Naïve hESCs derived in PXGGY were further characterized. While these cells lacked the defined colony morphology observed in 5i/L/A, they acquired a pre-implantation EPI identity within one passage and further passaging resulted in transition toward an ICM-like state (FIG. 5D and FIG. 5E). They also maintained expression of naïve-specific cell-surface markers during extended passaging and displayed a normal karyotype at P14. It was also confirmed that PXGGY induced biallelic MECP2 reporter activity. However, the efficiency of CD75/SUSD2 double-positive cells within the first 10 days of conversion remained low, leading us to examine whether provision of additional cytokines might facilitate the primed-to-naïve transition. An intriguing candidate is recombinant activin A, which was included in the 5i/L/A cocktail in order to enhance cell survival during primed-to-naïve resetting. Indeed, addition of activin A to PXGGY (PXGGY/A) enhanced naïve conversion efficiency, resulting in accelerated reprogramming kinetics as measured by flow cytometry on day 10 and colony formation efficiency at P2 (FIG. 5F and FIG. 5G). Naïve hESCs derived in PXGGY/A acquired a pre-EPI identity within two passages (FIG. 5D) and activin A could be withdrawn (PXGGY-A) without adversely affecting the expression of key naïve markers (FIG. 5E). Naïve hESCs derived in PXGGY/A underwent a similar global reduction in DNA methylation and imprint erasure as those derived in 5i/L/A, which is likely attributable to the inclusion of a direct MEK inhibitor (FIG. 5H).

Recent studies have shown that naïve hPSCs have an enhanced potential for extraembryonic differentiation and can give rise to human trophoblast stem cells (hTSCs). Naïve hESCs that were derived in PXGGY/A and maintained without activin A for two passages acquired a typical hTSC-like morphology and displayed activation of the hTSC-specific cell-surface markers EGFR and ITGA6 upon treatment with hTSC media. They also upregulated the primed-specific cell-surface marker CD90 upon re-priming in mTeSR1 media. Hence, naïve hESCs derived in PXGGY/A respond in comparable manner to trophoblast and re-priming conditions as those derived in 5i/L/A. We also confirmed that naïve hESCs derived in PXGGY/A could be switched to the three alternative MEKi-independent maintenance media (AXGY, GXGY, and FXGY), while sustaining the expression of naïve-specific cell-surface markers and their trophoblast potential.

Treatment of primed hESCs with the naïve induction cocktails 5i/L/A, PXGGY, or PXGGY/A strongly reduced p-ERK levels within 24 h, while p-ERK levels were maintained or only partially reduced upon treatment with alternative naïve maintenance media that failed to induce CD75/SUSD2 double-positive cells (FIG. 5I). These results suggest that the use of a direct MEK inhibitor is necessary, but not sufficient, to achieve full suppression of pERKin primed hESCs and facilitate the transition to naïve pluripotency. Consistent with this interpretation, titration or removal of the MEK inhibitor rapidly compromised reprogramming efficiency using the PXGGY/A cocktail (FIG. 5J). However, whether it might be possible to bypass the use of a direct MEK inhibitor during primed-to-naïve resetting was considered by combining other FGF pathway inhibitors with activin A. Indeed, heterogeneous induction of some CD75/SUSD2 double-positive cells was observed by treating primed hESCs with the FGFR inhibitor PD166866 in the presence of XGY and activin A (FIG. 5K). Furthermore, several combinations of FGF pathway inhibitors enabled more robust induction of naïve cells, including FGFRi+RAFi, FGFRi+ERKi, and RAFi+ERKi (FIG. 5K). These combinations were also able to induce MECP2-GFP/tdTomato double-positive cells, although conversion kinetics were not as efficient as in PXGGY/A. Hence, the use of a direct MEK inhibitor does not appear to be absolutely required for primed-to-naïve resetting but can be circumvented by combining other FGF pathway inhibitors in an optimized signaling environment (i.e., containing TNKS, PKC, ROCK inhibitors, and recombinant activin A).

Discussion

The past decade has witnessed substantial interest in the isolation of naïve hPSCs that correspond to pluripotent cells in the human pre-implantation embryo. Significant progress has been made toward capturing bona fide naïve hPSCs by primed-to-naïve resetting, deriving naïve hESCs directly from isolated ICM cells, and reprogramming somatic cells to pluripotency under naïve conditions. However, a detailed understanding of the signaling requirements for inducing and maintaining naïve human pluripotency has remained elusive. In an effort to expand the known repertoire of factors regulating naïve human pluripotency, high-throughput chemical screening using a library of ~3,000 well-annotated compounds was performed to identify alternative compounds that can maintain naïve hESCs in the absence of MEK and GSK3 inhibitors that are commonly included in naïve stem cell protocols.

Figure 6:
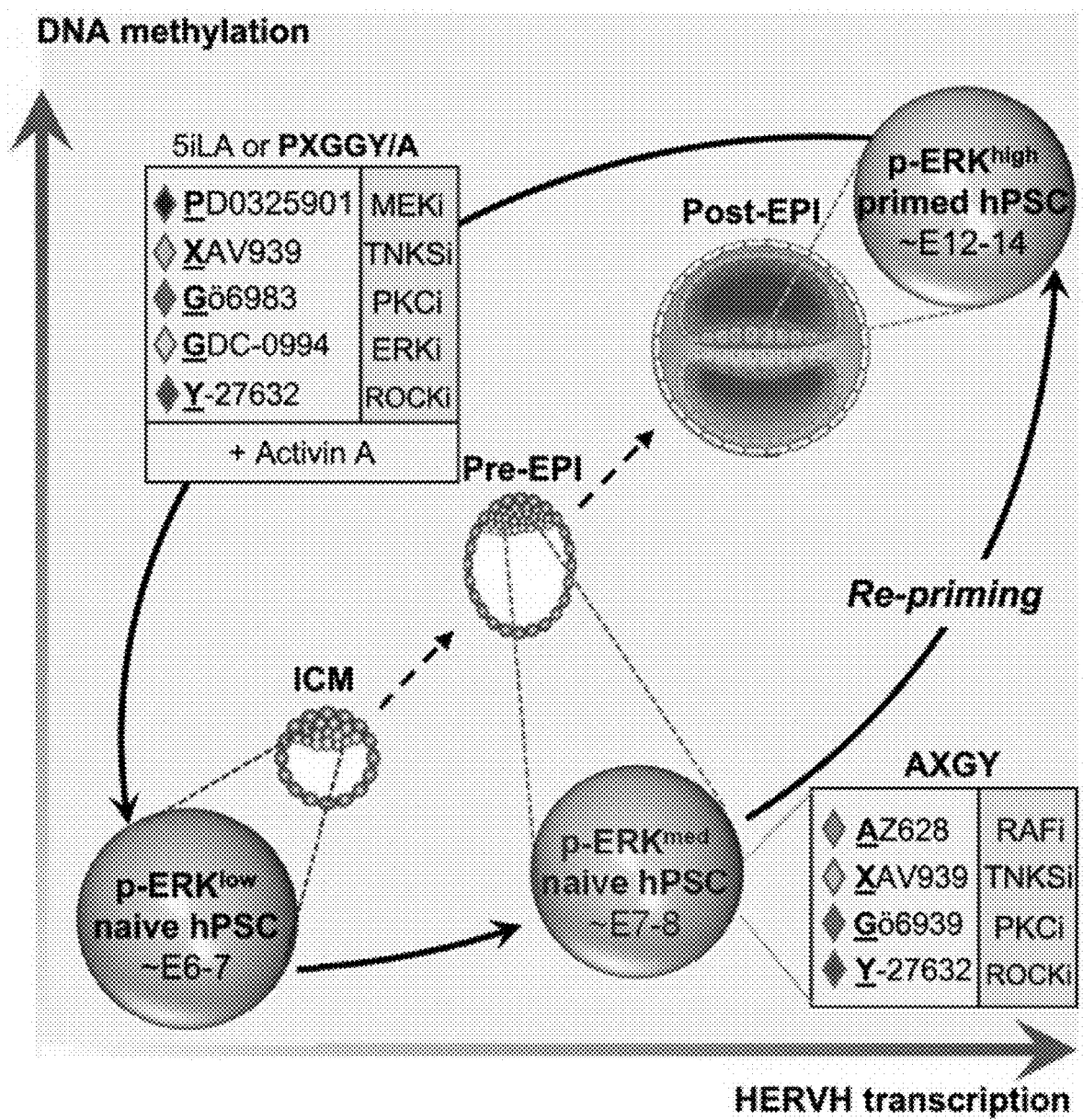
FIG. 6 shows distinct signaling requirements for inducing and maintaining naïve human pluripotency. Model summarizing the main findings from this study: dual MEK and ERK inhibition promotes efficient primed-to-naïve resetting in combination with TNKS, PKC, ROCK inhibitors, and activin A (PXGGY/A). These p-ERKLOW naïve hESCs resemble previously described 5i/L/A naïve hESCs and exhibit a human ICM-like identity based on comparison to 3D-cultured human embryos. They can transition into a pre-implantation EPI state with elevated levels of ERK phosphorylation in the presence of RAF, TNKS, PKC, and ROCK inhibitors (AXGY). These cells retain expression of typical naïve markers but also display increased levels of global DNA methylation and HERVH transcription. Global DNA methylation and HERVH transcription are further increased in the primed pluripotent state, which corresponds to the post-implantation epiblast at E12-14.
Figure 7:
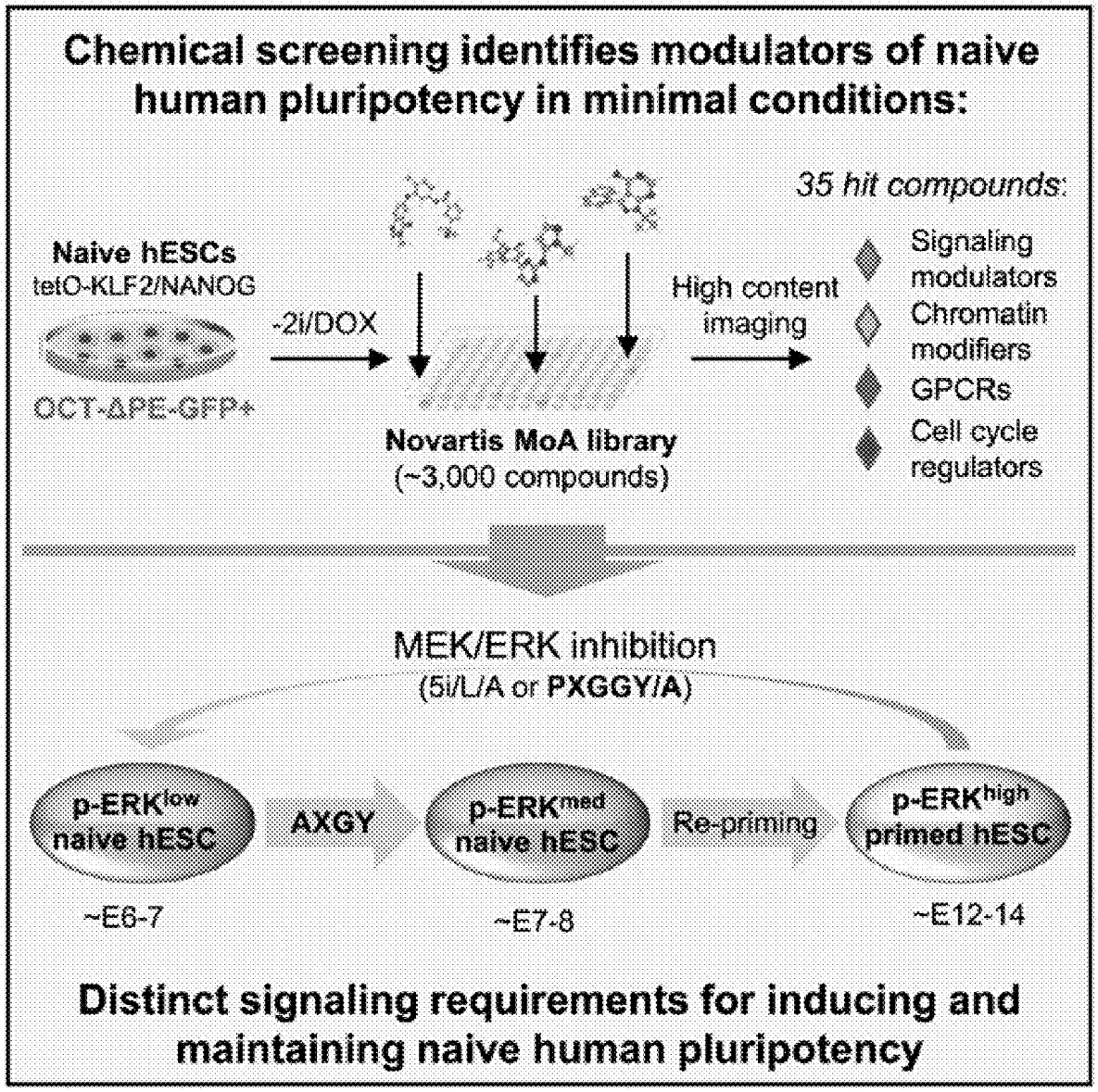
FIG. 7 shows a high-throughput chemical screen to identify essential signaling requirements for naïve human pluripotency in minimal conditions. They report that naïve hESCs can be maintained by blocking distinct nodes in the FGF signaling pathway and that dual MEK/ERK inhibition promotes efficient primed-to-naïve resetting in combination with activin A.

The present results demonstrate that MEK inhibitors can be replaced by inhibitors of both upstream (FGFR1, RAF) and downstream (ERK) kinases during the maintenance of naïve human pluripotency. The most robust expansion of naïve hESCs was attained in combination with TNKS, PKC, and ROCK inhibitors (XGY), in agreement with recent work from the Smith laboratory. Naïve hESCs maintained by FGFR, RAF, or ERK inhibitors displayed multiple hallmarks of naïve human pluripotency, including OCT4-ΔPE-GFP activity, biallelic X-linked reporter activity, and expression of key naïve pluripotency genes. Surprisingly, ERK phosphorylation was stimulated in naïve hESCs maintained with the RAF inhibitor AZ628 (AXGY) or FGFR inhibitor PD166866 (FXGY). Interestingly, however, modulation of these different nodes in the FGF pathway isolated naïve hESCs along progressive stages of early development: while the inclusion of a direct MEK inhibitor in 5i/L/A or PXGY captured naïve cells in a human ICM-like state, naïve cells maintained in the absence of MEK inhibitors progressed to a pre-implantation EPI identity and displayed increased expression of HERVH integrants (FIG. 6).

The alternative naïve maintenance formulations were unable to induce naïve pluripotency in primed hESCs, suggesting that complete MEK/ERK inhibition achieved by the 5i/L/A cocktail is critical for primed-to-naïve resetting. Dual inhibition of MEK and ERK in the presence of PKC, TNKS, and ROCK inhibitors provided an alternative naïve induction cocktail, which is referred to as PXGGY. When combined with activin A, this cocktail accelerated the activation of naïve-specific cell-surface markers and biallelic X-linked reporter activity compared to 5i/L/A. However, naïve hESCs generated with PXGGY/A still incurred imprint erasure, likely due to the inclusion of a direct MEK inhibitor. In the presence of XGY and activin A naïve cell induction could also be achieved by several other combinations of FGF pathway inhibitors, including FGFRi+RAFi, FGFRi+ERKi, and RAFi+ERKi, but reprogramming kinetics were reduced compared to PXGGY/A. This may provide a path to generate naïve hESCs in the absence of direct MEK inhibition, although it remains to be determined whether these cells meet stringent criteria for naïve pluripotency.

This work raises several questions for future investigation. First, it remains unclear how ERK phosphorylation is stimulated in the presence of upstream FGF pathway inhibitors. A potential mechanism involves the loss of negative feedback regulation, which could be explored by perturbing the expression of members of the DUSP and Sprouty families. These results also raise the possibility that upstream FGF pathway inhibitors may stimulate naïve human pluripotency through mechanisms that are located upstream of ERK, for example by blocking other RAF or MEK targets. A more complete understanding of the underlying biochemical mechanisms will likely require examination of the global phosphoproteome in naïve hESCs maintained with different FGF pathway inhibitors. Second, the alternative naïve maintenance conditions resulted in a progression in pre-implantation epiblast identity and increased HERVH expression compared to MEK inhibitor-containing naïve media. This suggests that the alternative naïve hESCs may be more responsive to embryonic lineage cues, while their enhanced proliferation may be beneficial for efforts to improve the contribution of naïve hESCs to interspecies chimeras or human blastocyst-like structures. Third, it will be important to evaluate which combination of naïve induction and maintenance conditions best preserves the long-term genomic integrity of naïve hESCs, while simultaneously mitigating the erosion of parent-specific DNA methylation marks at imprinted loci.

Figure 9A:
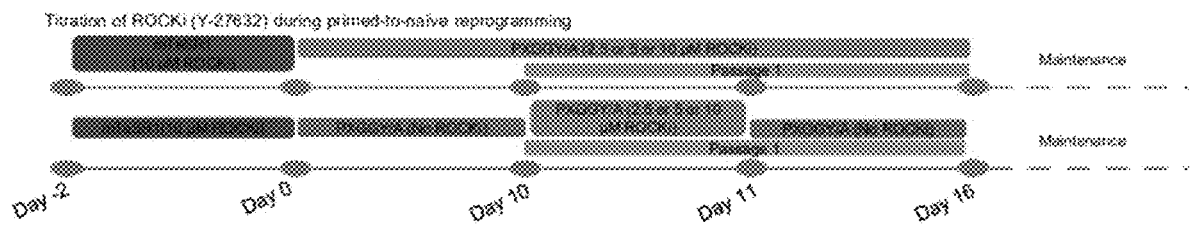
FIG. 9A-9J show the effect of ROCKi, IM12, and WH-04 on primed-to-naïve reprogramming using PXGGY/A.
Figure 9B:
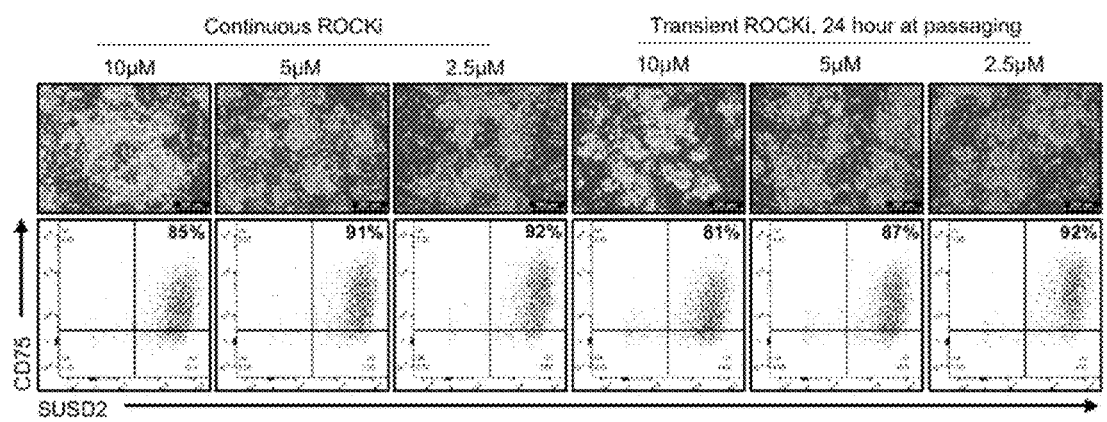

Example 2: Improving the Morphology and Homogeneity of naïve hESCs Derived Using PXGGY/A Example 1 establishes the PXGGY/A cocktail enables efficient primed-to-naïve reprogramming, homogenous induction of naïve-specific cell surface markers CD75 and SUSD2, and homogenous X-chromosome reactivation. However, the resulting naïve hESCs displayed a heterogeneous morphology compared to naïve cells generated using a 5i/L/A cocktail. To address this, the impact of ROCK inhibitor Y-27632 titration was first assessed when used continuously or transiently for only 24 hours at the time of passaging during primed-to-naïve reprogramming (FIG. 9A and FIG. 9B). The transient application of 10 µM ROCKi improves the morphology of reprogrammed naïve hESCs without any significant reduction in the CD75+/SUSD2+ cell proportion (FIG. 9B). The PXGG$_y$/A composition from hereon will be denoted as PXGGY/A to specify transient use of ROCKi.

Figure 9C:
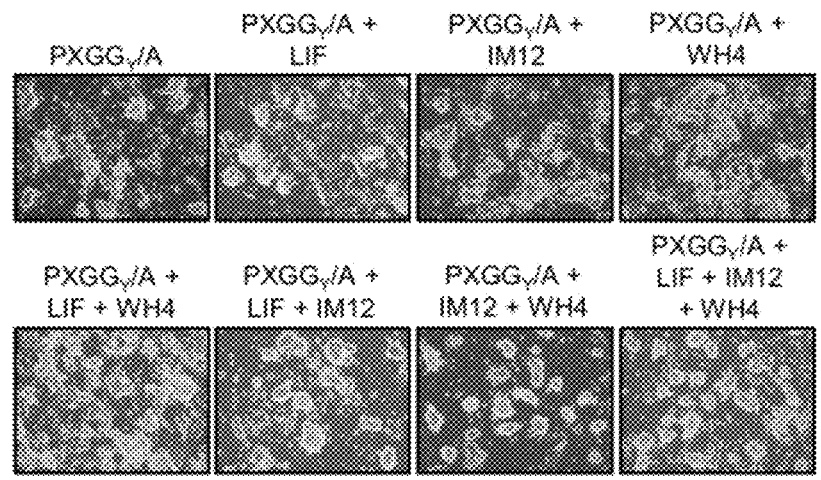
Figure 9D:
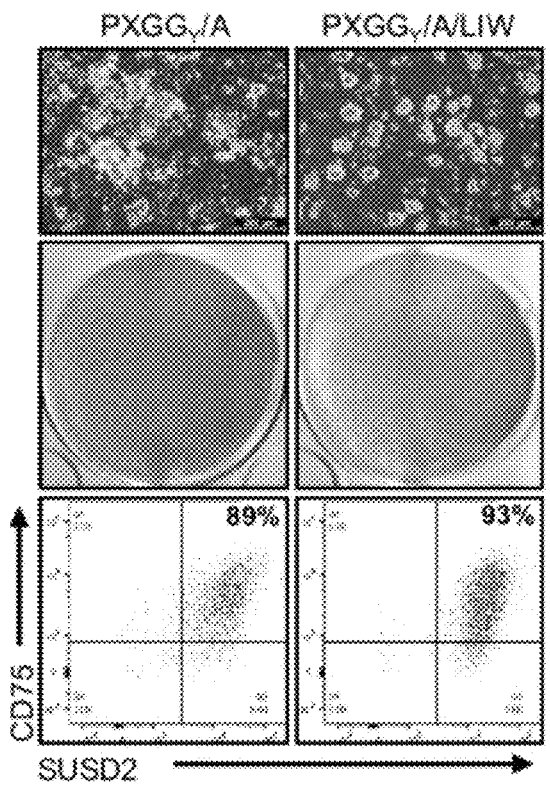
Figure 9E:
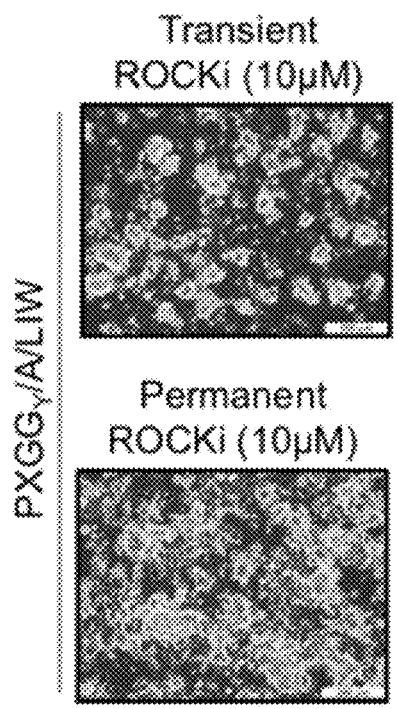

However, the morphology of naïve hESCs reprogrammed using this condition still appeared flat compared to the characteristic dome-shaped colony morphology associated with naïve pluripotency. Therefore, the impact of additional cytokines and inhibitors in the 5i/L/A cocktail were tested, including leukemia inhibitory factory (LIF), the GSK3-β inhibitor IM12, and the SRC inhibitor WH-04 (FIG. 9C). The individual addition of 20 ng/mL LIF, 0.5 μM IM12, or 0.5 μM WH-04 to the PXGG$_Y$/A cocktail did not result in a major improvement in the morphological appearance of naïve hESCs. However, when combined together naïve hESCs displayed a substantially improved colony morphology (FIG. 9C). This new primed-to-naïve reprogramming cocktail composition is referred to as PXGGy/A/LIW (LIF, IM12 and WH-04). While the addition of LIW caused a modest reduction in colony numbers, both the morphology and homogeneity of the CD75+/SUSD2+ cell population were improved (FIG. 9D). The impact of continuous vs. transient ROCKi in the presence of LIW was also reassessed, and again confirmed that transient ROCKi improves naïve colony morphology (FIG. 9E).

Figure 9F:
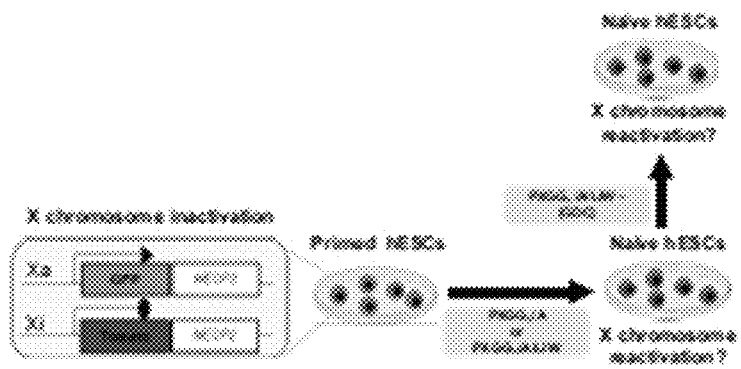
Figure 9G:
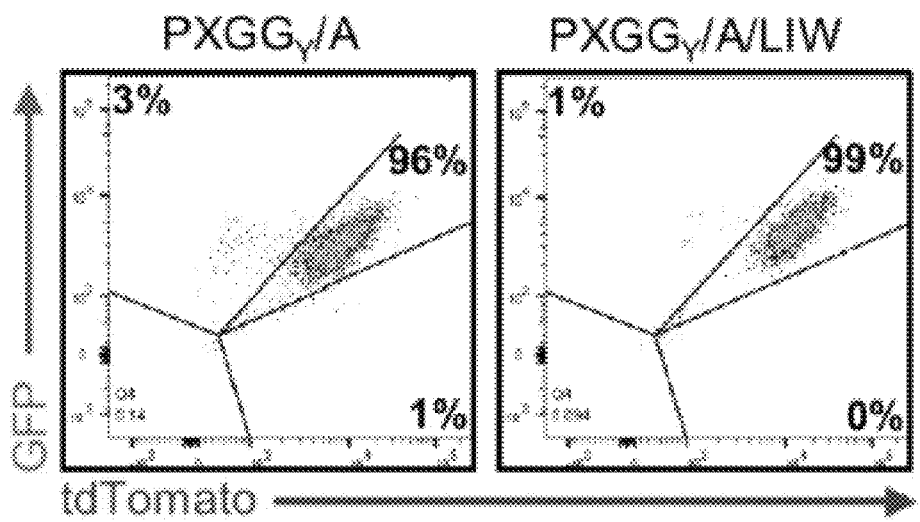
Figure 9H:
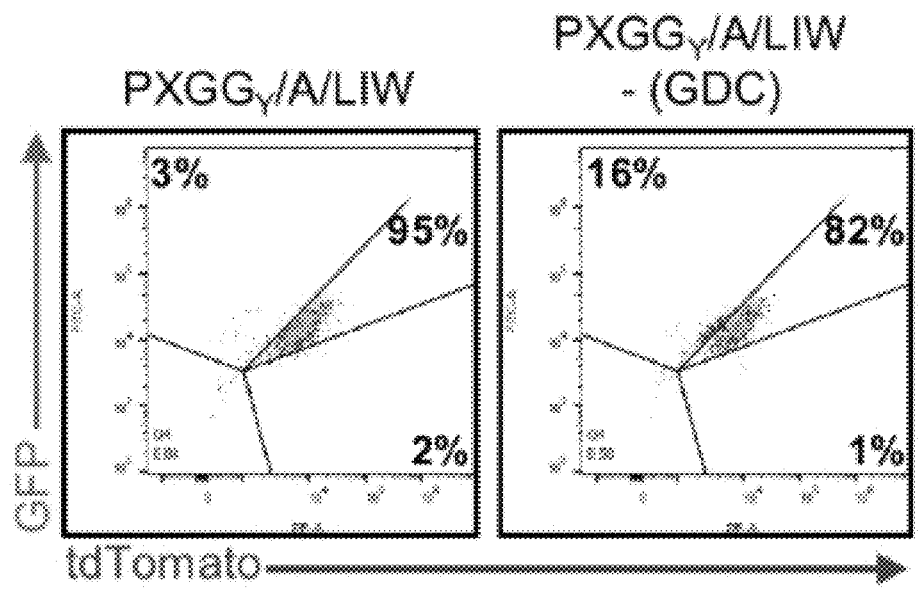
Figure 9I:
Figure 9J:
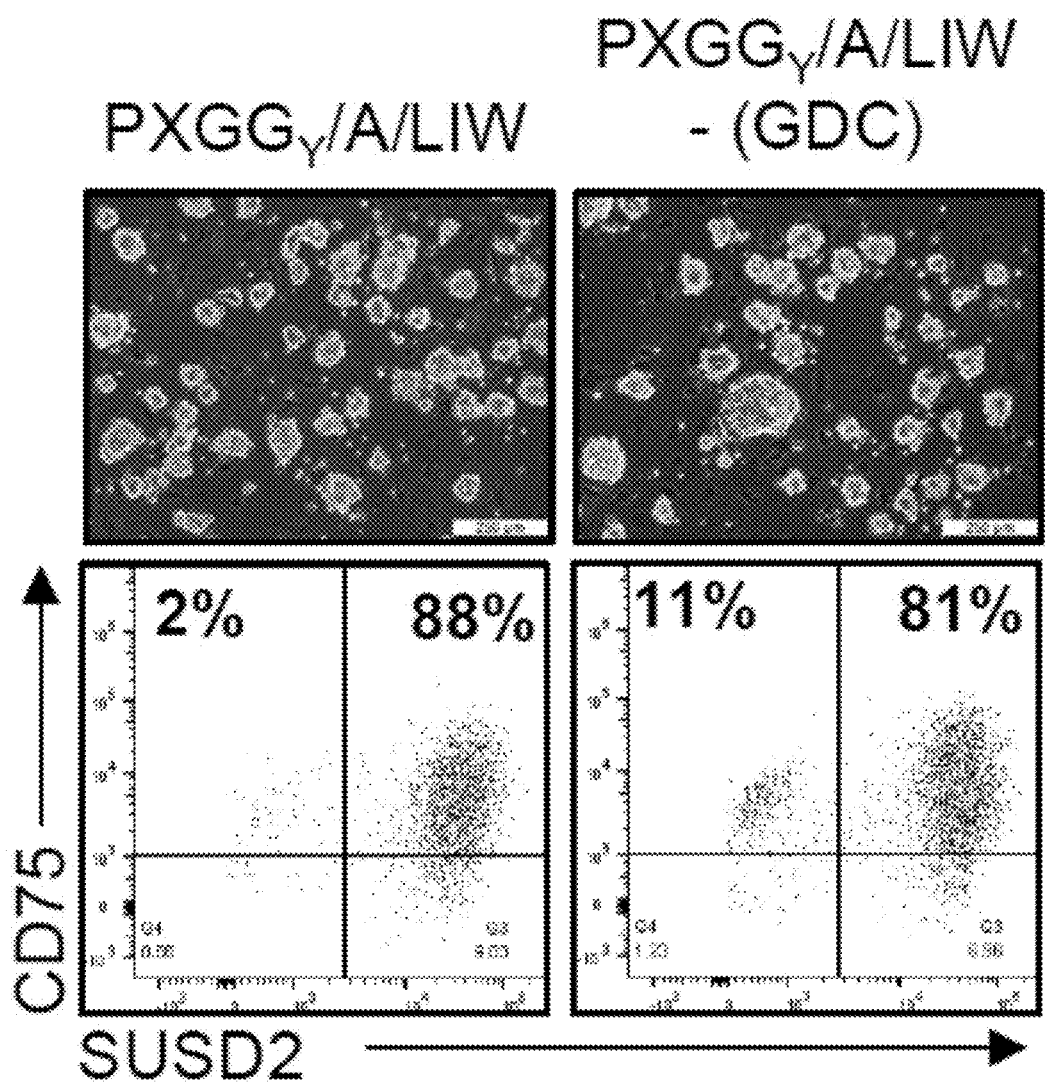

The WIBR3 MECP2-GFP/tdTomato dual reporter hESC line was then used to assess the extent of X-chromosome reactivation (XCR) in naïve hESCs reprogrammed using PXGG$_Y$/A in the presence or absence of LIW (FIG. 9F). Both cocktails resulted in homogeneous induction of biallelic MECP2 reporter activity, but the purity of the double positive population was further enhanced in the presence of LIW (FIG. 9G). It was also asked whether continuous dual inhibition of MEK and ERK was required for maintenance of the resulting naïve hESCs, since it was previously reported that either of these inhibitors is sufficient to maintain naïve human pluripotency on its own in Example 1. Withdrawal of the ERK inhibitor GDC-0994 from the PXGG$_Y$/A/LIW cocktail one passage after derivation from the primed state was broadly compatible with maintenance of biallelic MECP2 reporter activity (FIG. 9F and FIG. 9H) and CD75/SUSD2 expression (FIG. 9I-9J), but the purity of the naïve population as assessed by both parameters was slightly reduced in the absence of GDC-0994. Hence, the PXGG$_Y$/A/LIW cocktail confers the most efficient and homogeneous route for primed-to-naïve resetting thus far. Furthermore, this data suggest that this cocktail is optimal for maintenance of pure naïve hESCs, although the ERK inhibitor can be removed with a modest increase in heterogeneity.

Exciting potential applications of this protocol for enhanced primed-to-naïve resetting include the generation of human trophoblast stem cells and 3D trophoblast organoids to model placental development and disease, the creation of 3D blastocyst-like structures (a.k.a. "blastoids") to model human embryonic development and implantation failure, enhanced contribution to interspecies chimeras for disease modeling or organ transplantation, and improved methods for transgene-free chemical reprogramming of human somatic cells.

TABLE 7

Media composition 7: Enhanced primed-to-naive resetting and maintenance media with improved morphology Related to FIG. 9

| | Composition: N2B27+ | | | | | | | | | |
|---|---|---|---|---|---|---|---|---|---|---|
| Media | PD03 (P) | XAV (X) | Go (G) | GDC (G) | Transient ROCKi ($_Y$) | ActA (A) | LIF (L) | IM12 (I) | WH-04 (W) | Application |
| PXGG$_Y$/ A/LIW | 1 μM | 2 μM | 2 μM | 2.5 μM | 10 μM | 10 ng/mL | 20 ng/mL | 0.5 μM | 0.5 μM | Primed-to-naïve resetting of hPSCs |
| PXG$_Y$/ A/LIW | 1 μM | 2 μM | 2 μM | | 10 μM | 10 ng/mL | 20 ng/mL | 0.5 μM | 0.5 μM | Maintenance of naïve hPSCs |

Note:
ROCKi is used transiently for 24 hours at the time of passaging the cells

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

Equivalents

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein, a "population" of cells refers to a group of at least 2 cells, e.g. 2 cells, 3 cells, 4 cells, 10 cells, 100 cells, 1000 cells, 10,000 cells, 100,000 cells or any value in between, or more cells. Optionally, a population of cells can be cells which have a common origin, e.g. they can be descended from the same parental cell, they can be clonal, they can be isolated from or descended from cells isolated from the same tissue, or they can be isolated from or descended from cells isolated from the same tissue sample. Preferably, the population of hematopoietic progenitor cells is substantially purified. As used herein, the term "substantially purified" means a population of cells substantially homogeneous for a particular marker or combination of markers. By substantially homogeneous is meant at least 80%, at least 85%, at least 90%, at least 95%, at least 96%, at least 97%, at least 98%, at least 99% or more homogeneous for a particular marker or combination of markers.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The term "about" or "approximately" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

The terms "composition" and "formulation" are used interchangeably.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs); and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is a non-human animal. In certain embodiments, the animal is a fish or reptile.

The term "administer," "administering," or "administration" refers to implanting, absorbing, ingesting, injecting, inhaling, or otherwise introducing a compound or cell described herein or generated as described herein, or a composition thereof, in or on a subject.

The terms "treatment," "treat," and "treating" refer to reversing, alleviating, delaying the onset of, or inhibiting the progress of a disease. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen and/or in light of detecting that the subject has a genotype associated with the disease). Treatment may also be continued after symptoms have resolved, for example, to delay or prevent recurrence.

The terms "condition," "disease," and "disorder" are used interchangeably.

A "kinase" is a type of enzyme that transfers phosphate groups from high energy donor molecules, such as ATP, to specific substrates, referred to as phosphorylation. Kinases are part of the larger family of phosphotransferases. One of the largest groups of kinases are protein kinases, which act on and modify the activity of specific proteins. Kinases are used extensively to transmit signals and control complex processes in cells. Various other kinases act on small molecules such as lipids, carbohydrates, amino acids, and nucleotides, either for signaling or to prime them for metabolic pathways. Kinases are often named after their substrates. More than 500 different protein kinases have been identified in humans. These exemplary human protein kinases include, but are not limited to, AAK1, ABL, ACK, ACTR2, ACTR2B, AKT1, AKT2, AKT3, ALK, ALK1, ALK2, ALK4, ALK7, AMPKal, AMPKa2, ANKRD3, ANPa, ANPb, ARAF, ARAFps, ARG, AurA, AurApsl, AurAps2, AurB, AurBpsl, AurC, AXL, BARK1, BARK2, BIKE, BLK, BMPR1A, BMPRIApsl, BMPRIAps2, BMPR1B, BMPR2, BMX, BRAF, BRAFps, BRK, BRSK1, BRSK2, BTK, BUB1, BUBR1, CaMKIa, CaMKIb, CaMKId, CaMKIg, CaMK2a, CaMK2b, CaMK2d, CaMK2g, CaMK4, CaMKKI, CaMKK2, caMLCK, CASK, CCK4, CCRK, CDC2, CDC7, CDK10, CDK11, CDK2, CDK3, CDK4, CDK4ps, CDK5, CDK5ps, CDK6, CDK7, CDK7ps, CDK8, CDK8ps, CDK9, CDKL1, CDKL2, CDKL3, CDKL4, CDKL5, CGDps, CHED, CHK1, CHK2, CHK2psl, CHK2ps2, CKIa, CKIa2, CKIapsl, CKIaps2, CKIaps3, CKId, CKIe, CKIgI, CKIg2, CKIg2ps, CKIg3, CK2al, CK2al-rs, CK2a2, CLIK1, CLIK1L, CLK1, CLK2, CLK2ps, CLK3, CLK3ps, CLK4, COT, CRIK, CRK7, CSK, CTK, CYGD, CYGF, DAPK1, DAPK2, DAPK3, DCAMKL1, DCAMKL2, DCAMKL3, DDR1, DDR2, DLK, DMPKI, DMPK2, DRAKI, DRAK2, DYRKIA, DYRKIB, DYRK2, DYRK3, DYRK4, EGFR, EphAl, EphAlO, EphA2, EphA3, EphA4, EphA5, EphA6, EphA7, EphA8, EphBI, EphB2, EphB3, EphB4, EphB6, Erkl, Erk2, Erk3, Erk3psl, Erk3ps2, Erk3ps3, Erk3ps4, Erk4, Erk5, Erk7, FAK, FER, FERps, FES, FGFR1, FGFR2, FGFR3, FGFR4, FGR, FLT1, FLTIps, FLT3, FLT4, FMS, FRK, Fused, FYN, GAK, GCK, GCN2, GCN22, GPRK4, GPRK5, GPRK6, GPRK6ps, GPRK7, GSK3A, GSK3B, Haspin, HCK, HER2/ErbB2, HER3/ErbB3, HER4/ErbB4, HH498, HIPK1, HIPK2, HIPK3, HIPK4, HPK1, HRI, HRIps, HSER, HUNK, ICK, IGF1R, IKKa, IKKb, IKKe, ILK, INSR, IRAKI, IRAK2, IRAK3, IRAK4, IRE1, IRE2, IRR, ITK, JAK1, JAK2, JAK3, JNK1, JNK2, JNK3, KDR, KHS1, KHS2, KIS, KIT, KSGCps, KSR1, KSR2, LATS1, LATS2, LCK, LIMK1, LIMK2, LIMK2ps, LKB1, LMR1, LMR2, LMR3, LOK, LRRK1, LRRK2, LTK, LYN, LZK, MAK, MAP2K1, MAP2KIps, MAP2K2, MAP2K2ps, MAP2K3, MAP2K4, MAP2K5, MAP2K6, MAP2K7, MAP3K1, MAP3K2, MAP3K3, MAP3K4, MAP3K5, MAP3K6, MAP3K7, MAP3K8, MAPKAPK2, MAPKAPK3, MAPKAPK5, MAPKAPKpsI, MARK1, MARK2, MARK3, MARK4, MARKpsOI, MARKps02, MARKps03, MARKps04, MARKps05, MARKps07, MARKps08, MARKps09, MARKpsIO, MARKpsI 1, MARKpsI2, MARKpsI3, MARKpsI5, MARKpsI6, MARKpsI7, MARKpsI8, MARKpsI9, MARKps20, MARKps21, MARKps22, MARKps23, MARKps24, MARKps25, MARKps26, MARKps27, MARKps28, MARKps29, MARKps30, MAST1, MAST2, MAST3, MAST4, MASTL, MELK, MER, MET, MISR2, MLK1, MLK2, MLK3, MLK4, MLKL, MNK1, MNKIps, MNK2, MOK, MOS, MPSK1, MPSKIps, MRCKa, MRCKb, MRCKps, MSK1, MSK12, MSK2, MSK22, MSSK1, MST1, MST2, MST3, MST3ps, MST4, MUSK, MY03A, MY03B, MYT1, NDR1, NDR2, NEK1, NEK10, NEK11, NEK2, NEK2psl, NEK2ps2, NEK2ps3, NEK3, NEK4, NEK4ps, NEK5, NEK6, NEK7, NEK8, NEK9, NIK, NIM1, NLK, NRBP1, NRBP2, NuaKI, NuaK2, Obscn, Obscn2, OSR1, p38a, p38b, p38d, p38g, p70S6K, p70S6Kb, p70S6Kpsl, p70S6Kps2, PAKI, PAK2, PAK2ps, PAK3, PAK4, PAK5, PAK6, PASK, PBK, PCTAIREI, PCTAIRE2, PCTAIRE3, PDGFRa, PDGFRb, PDKI, PEK, PFTAIREI, PFTAIRE2, PHKg1, PHKglpsl, PHKglps2, PHKglps3, PHKg2, PIK3R4, PIM1, PIM2, PIM3, PINK1, PITSLRE, PKACa, PKACb, PKACg, PKCa, PKCb, PKCd, PKCe, PKCg, PKCh, PKCi, PKCips, PKCt, PKCz, PKD1, PKD2, PKD3, PKG1, PKG2, PKN1, PKN2, PKN3, PKR, PLK1, PLKlpsl, PLKIps2, PLK2, PLK3, PLK4, PRKX, PRKXps, PRKY, PRP4, PRP4ps, PRPK, PSKH1, PSKHIps, PSKH2, PYK2, QIK, QSK, RAF1, RAFIps, RET, RHOK, RIPK1, RIPK2, RIPK3, RNAseL, ROCK1, ROCK2, RON, ROR1, ROR2, ROS, RSK1, RSK12, RSK2, RSK22, RSK3, RSK32, RSK4, RSK42, RSKL1, RSKL2, RYK, RYKps, SAKps, SBK, SCYL1, SCYL2, SCYL2ps, SCYL3, SGK, SgK050ps, SgK069, SgK071, SgK085, SgKI IO, SgK196, SGK2, SgK223, SgK269, SgK288, SGK3, SgK307, SgK384ps, SgK396, SgK424, SgK493, SgK494, SgK495, SgK496, SIK (e.g., SIK1, SIK2), skMLCK, SLK, Slob, smMLCK, SNRK, SPEG, SPEG2, SRC, SRM, SRPK1, SRPK2, SRPK2ps, SSTK, STK33, STK33ps, STLK3, STLK5, STLK6, STLK6psl, STLK6-rs, SuRTK106, SYK, TAK1, TAOI, TA02, TA03, TBCK, TBK1, TEC, TESK1, TESK2, TGFbRI, TGFbR2, TIE1, TIE2, TLK1, TLKIps, TLK2, TLK2psl, TLK2ps2, TNK1, Trad, Trbl, Trb2, Trb3, Trio, TRKA, TRKB, TRKC, TSSK1, TSSK2, TSSK3, TSSK4, TSSKpsl, TSSKps2, TTBK1, TTBK2, TTK, TTN, TXK, TYK2, TYK22, TYR03, TYR03ps, ULK1, ULK2, ULK3, ULK4, VACAMKL, VRK1, VRK2, VRK3, VRK3ps, Weel, WeelB, WeelBps, Weelpsl, Weelps2, Wnkl, Wnk2, Wnk3, Wnk4, YANK1, YANK2, YANK3, YES, YESps, YSK1, ZAK, ZAP70, ZC1/HGK, ZC2/TNIK, ZC3/MINK, and ZC4/NRK.

The term "inhibition", "inhibiting", "inhibit," or "inhibitor" refer to the ability of a compound to reduce, slow, halt, or prevent activity of a particular biological process (e.g., kinase activity) in a cell relative to vehicle.

By "pluripotency" and pluripotent stem cells it is meant that such cells have the ability under appropriate conditions to differentiate into cells that are derivatives of all three embryonic germ layers (endoderm, mesoderm and ectoderm). A pluripotent cell line or cell culture is often characterized in that the cells can differentiate into a wide variety of cell types in vitro and in vivo. Cells that are able to form teratomas containing cells having characteristics of endoderm, mesoderm, and ectoderm when injected into SCID mice are considered pluripotent. In addition, cells that possess the ability to participate in the formation of chimeras (upon injection into a blastocyst of the same species that is transferred to a suitable foster mother of the same species) that survive to term are considered pluripotent. Pluripotent cell types as used in the present invention may be provided in the form of human embryonic stem cells, or human induced pluripotent cell (iPS cell), or may be derived from a human embryonic stem cell line.

The term "stem cell" refers to a vertebrate cell that has the ability both to self-renew, and to generate differentiated progeny. The ability to generate differentiated progeny may be described as pluripotent (see Morrison et al. (1997) Cell 88:287-298). "Embryonic stem cells" (ES cells) are pluripotent stem cells derived from the inner cell mass of a blastocyst, an early-stage preimplantation embryo. Pluripotency distinguishes embryonic stem cells from adult stem cells found in adults; while embryonic stem cells can generate all cell types in the body, adult stem cells are multipotent and can produce only a limited number of cell types.

"Induced pluripotent stem cells", abbreviated as iPS cells, are a type of pluripotent stem cell artificially derived from a non-pluripotent cell, typically an adult somatic cell, by inducing expression of certain genes (e.g., injection of an expression construct). Induced pluripotent stem cells are identical in many respects to natural pluripotent stem cells, such as embryonic stem (ES) cells (e.g., in their physical properties). They may be the same in their expressions of certain stem cell genes and proteins, chromatin methylation patterns, doubling time, embryoid body formation, teratoma formation, viable chimera formation, and potency and differentiability. The term "induced pluripotent stem cell" encompasses pluripotent cells, that, like embryonic stem (ES) cells, can be cultured over a long period of time while maintaining the ability to differentiate into all types of cells in an organism. However, unlike ES cells (which are typically derived from the inner cell mass of blastocysts), iPS cells are derived from differentiated somatic cells, that is, cells that have a narrower, more defined potential.

By "culturing" the cell means growing the cells in an artificial, in vitro environment. By "maintaining" means continuing to grow the cells in culture under suitable conditions until the pluripotency state of the cell is converted to a more naïve state.

"Cell line" refers to a population of largely or substantially identical cells, wherein the cells have often been derived from a single ancestor cell or from a defined and/or substantially identical population of ancestor cells. For example, a cell line may consist of descendants of a single cell. A cell line may have been or may be capable of being maintained in culture for an extended period (e.g., months, years, for an unlimited period of time). It will be appreciated that cells may acquire mutations and possibly epigenetic changes over time such that some individual cells of a cell line may differ with respect to each other. In some embodiments, at least 80%, 85%, 86%, 87%, 88%, 89%, 90%, 91%, 92%, 93%, 94%, 95%, 96%, 97%, 98%, or 99% of the cells of a cell line or cell culture are at least 95%, 96%, 97%, 98%, or 99% genetically identical. In some embodiments, at least 80%, 85%, 86%, 87%, 88%, 89%, 90%, 91%, 92%, 93%, 94%, 95%, 96%, 97%, 98%, or 99% A of the cells of a cell line or cell culture express the same set of cell surface markers. The set of markers could be markers indicative of ground state (naïve) pluripotency or cell-type specific markers.

A "clone" refers to a cell derived from a single cell without change. It will be understood that if cells of a clone are subjected to different culture conditions or if some of the cells are subjected to genetic modification, the resulting cells may be considered distinct clones.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method of maintaining or passaging at least one naïve human embryonic stem cell in the absence of a mitogen-activated protein kinase kinase (MEK) inhibitor, the method comprising:

culturing the at least one naïve human embryonic stem cell in the presence of Tankyrase (TNKS) inhibitor XAV939, Protein Kinase C (PKC) inhibitor Go6983, a Rho-Associated Protein kinase (ROCK) inhibitor comprising Y-27632, and Rapidly Accelerated Fibrosarcoma (RAF) kinase inhibitor AZ628.

* * * * *